(12) United States Patent
Howe et al.

(10) Patent No.: US 6,423,491 B1
(45) Date of Patent: Jul. 23, 2002

(54) METHOD OF DIAGNOSING JUVENILE POLYPOSIS (JP)

(75) Inventors: James R. Howe, Iowa City, IA (US); Lauri A. Aaltonen, Espoo (FI)

(73) Assignee: University of Iowa Research Foundation, Iowa City, IA (US)

(*) Notice: Subject to any disclaimer, the term of this patent is extended or adjusted under 35 U.S.C. 154(b) by 0 days.

(21) Appl. No.: 09/312,748

(22) Filed: May 13, 1999

Related U.S. Application Data
(60) Provisional application No. 60/085,312, filed on May 13, 1998.

(51) Int. Cl.$^7$ .......................... C12Q 1/00; C12Q 1/68; G01N 33/567; G01N 33/574; G01N 33/53

(52) U.S. Cl. .................... 435/6; 435/4; 435/7.1; 435/7.21; 435/7.23; 435/7.92; 435/7.95; 436/63; 436/64

(58) Field of Search ................... 435/4, 6, 7.1, 7.21, 435/7.23, 7.92, 7.95; 436/63, 64

(56) References Cited

U.S. PATENT DOCUMENTS
5,712,097 A  1/1998  Kern et al. ................ 435/6

OTHER PUBLICATIONS

Stedman, Thomas. Illustrated Stedman's Medical Dicationary, 24th Edition, 1992.*
Yershov et al. DNA analysis and diagnostics on oligonucleotide microchips. Proc. Natl. Acad. Sci. USA 93:4913–4918, 1996.*
Verbeek et al. DPC 4/SMAD 4 in non–pancreatic tumors with frequent LOH 18q21 and in hematological malignancies. International Journal of Oncology 10:257–260, 1997.*
Baptist and Sabatini, "Coexisting juvenile polyps and tubulovillous adenoma of colon with carcinoma in situ: report of a case," *Hum. Pathol.* 16:1061–1063, 1985.
Devereux et al., "Smad4 (homolog of human DPC4) and Smad2 (homolog of human JV18–1): candidates for murine lung tumor resistance and suppressor genes," *Carcinogenesis;* 18(9): 1751–1755. 1997.
Fazeli et al., "Phenotype of mice lacking functional deleted in colorectal cancer (Dcc) gene," *Nature* 386, 796–804, 1997.
Fearon and Vogelstein, "A genetic model for colorectal tumorigenesis," *Cell*, 61:759–767, 1990.
Fearon et al., "Identification of a chromosome 18q gene that is altered in colorectal cancers," *Science* 247, 49–56, 1990.
Goodman et al., "Recombinant adeno–associated virus–mediated gene transfer into hematopoietic progenitor cells," *Blood*, 84(5):1492–1500, 1994.
Goodman et al., "Pathogenesis of colonic polyps in multiple juvenile polyposis," *Cancer* 43, 1906–1913, 1979.

Grotsky et al., "Familial juvenile polyposis coli, a clinical and pathologic study of a large kindred," *Gastroenterology* 82:494–501, 1982.
Hemminki et al., "Localization of a susceptibility locus for Peutz–Jeghers syndrome to 19p using comparative genomic hybridization and targeted linkage analysis," *Nat. Genet.* 15:87–90, 1997.
Hemminki et al., "A serine/threonine kinase gene defective in Peutz–Jeghers syndrome," *Nature* 391:184–187, 1998.
Hollstein et al., "p53 mutations in human cancers," *Science*, 253:49–53, 1991.
Howe and Conlon, "The molecular genetics of pancreatic cancer," *Surgical Oncology*, 6(1):1–18, 1997.
Howe and Guillem, "The genetics of colorectal cancer," *Surgical Clinics of North America*, 77(1):175–195, 1997.
Howe et al., "A gene for familial juvenile polyposis maps to chromosome 18q21.1," *Am. J. Hum. Genet.* 62:1129–1136. 1998.
Howe et al., "Improved predictive test for MEN2, using flanking dinucleotide repeats and RFLPs," *Am. J. Hum. Genet.* 51, 1430–1442, 1992a.
Howe et al., "Factors predictive of survival in ampullary carcinoma," *Annals of Surgery*, 228(1):87–94, 1998.
Howe et al., K–ras mutation in adenomas and carcinomas of the ampulla of Vater,: Clinical *Cancer Research* 3, 129–133, 1997.
Howe et al., "DNA extraction from paraffin–embedded tissues using a salting–out procedure: a reliable method for PCR amplification of archival material," *Histol. Histopathol.* 12:595–601, 1997.
Howe et al., "Development of a sequence–tagged site for the centromere of chromosome 10: its use in cytogenetic and physical mapping," *Human Genetics* 91, 199–204, 1993.
Howe et al., "A new RFLP marker D12S54 maps between F8VWF and KRAS2 on human chromosome 12p," *Nucleic Acids Research*; 19(9):2512, 1991.
Howe et al., "A new RFLP marker D5S348 maps to 5p14.3—15.2, between D5S60 (CRI–R535) and HPRTP2," *Nucleic Acids Research*, 20(5):1168, 1992.
Howe et al., "Mutations in the SMAD4/DPC4 gene in juvenile polyposis," *Science* 280, 1086–1088, 1998.
Howe et al., "Presymptomatic identification of carriers of the multiple endocrine neoplasia type 2A gene using flanking DNA markers," *Surgery* 112:219–226, 1992b.

(List continued on next page.)

Primary Examiner—Anthony C. Caputa
Assistant Examiner—Alana M. Harris
(74) Attorney, Agent, or Firm—Fulbright & Jaworski, LLP

(57) ABSTRACT

Familial juvenile polyposis is an autosomal dominant disease characterized by a predisposition to hamartomatous polyps and gastrointestinal cancer. The present invention shows that JP families carry germline mutations in SMAD4/DPC4, a gene on chromosome 18q21.1. The mutant SMAD4 proteins are truncated at the carboxyl–terminus and lack sequences required for normal function. Methods and compositions for the detection and amelioration of FJP and gastrointestinal tumors are provided.

30 Claims, 5 Drawing Sheets

OTHER PUBLICATIONS

Hursh et al., "Cross regulation of decapentaplegic and ultrabithorax transcription in the embryonic visceral mesoderm of Drosophilia," *Development*, 117:1211–1222, 1993.

Jacoby et al., "Del(10) (q22.3q24.1) associated with juvenile polyposis," *American Journal of Medical Genetics* 70:361–364, 1997a.

Jacoby et al., "A juvenile polyposis tumor suppressor locus at 10q22 is deleted from nonepithelial cells in the lamina propria," *Gastroenterology* 112, 1398–1403, 1997b.

Jarvinen and Franssila, "Familial juvenile polyposis coli, increased risk of colorectal cancer," *Gut* 25, 792–800, 1984.

Jarvinen, "Juvenile gastrointestinal polyposis," *Problems in General Surgery* 10, 749–757, 1993.

Jass et al., "Juvenile polyposis–a precancerous condition," *Histopathology*, 13:619–630, 1988.

Jass, In: Utsunomiya J, Lynch HT (eds) "Hereditary colorectal cancer." *Springer, Tokyo*, pp 343–350, 1990.

Jones et al., "Juvenile polyp with intramucosal carcinoma," *Arch Pathol Lab Med* 111:200–201, 1987.

Lagna et al., "Partnership between DPC4 and SMAD proteins in TGF–β signalling pathways," *Nature*, 383:832, 1996.

Landis et al., "Cancer statistics," *CA–A Cancer Journal for Clinicians* 48, 6–30, 1998.

Leggett et al., "Exclusion of APC and MCC as the gene defect in one family with familial juvenile polyposis," *Gastroenterology* 105, 1313–1316, 1993.

Liaw et al., "Germline mutations of the PTEN gene in Cowden disease, an inherited breast and thyroid cancer syndrome," *Nat Genet* 16:64–67, 1997.

Liu et al., "Malignant change of juvenile polyp of colon," *Chin Med J (Engl)* 4(6):434–439, 1978.

Lynch et al., "Hereditary nonpolyposis colorectal cancer (Lynch syndromes I and II," *Cancer* 56, 939–951, 1985.

Lynch, "Inherited mutations in PTEN that are associated with breast cancer, Cowden disease, and juvenile polyposis," *Am J Hum Genet* 61:1254–1260, 1997.

MacGrogan et al., "Comparative mutational analysis of DPC4 (Smad4) in prostatic and colorectal carcinomas," *Oncogene*; 15(9): 1111–1114, 1997.

Marsh et al., "Exclusion of PTEN and 10q22–24 as the susceptibility locus for juvenile polyposis syndrome," *Cancer Research* 57, 5017–5021, 1997.

Marsh et al., "Germline mutations in PTEN are present in Bannayan–Zonana syndrome," *Nature Genet.*, 16:333, 1997.

Mehenni et al., "Peutz–Jeghers syndrome: confirmation of linkage to chromosome 19p13.3 and identification of a potential second locus, on 19q13.4," *Am J Hum Genet* 61:1327–1334, 1997.

Nelen et al., "Localization of the gene for Cowden disease to chromosome 10q22–23," *Nature Genetics* 13, 114–116, 1996.

Nishizuka et al., "Analysis of the DPC4 gene in gastric carcinoma," *Jpn J Cancer Res*; 88(4): 335–339, 1997.

Olschwang et al., PTEN germ–line mutations in juvenile polyposis coli, *Nat Genet* 18:12–14, 1998.

Ramaswamy et al., "Juvenile polyposis of the colon with atypical adenomatous changes and carcinoma in situ," *Diseases of the Colon and Rectum* 27, 393–398, 1984.

Riggins et al., "Normal PTEN gene in juvenile polyposis." *NOGO* 1:1 (http://pathology.jhu.edu/nogo/), 1997.

Rozen and Baratz, "Familial juvenile colonic polyposis with associated colon cancer," *Cancer* 49:1500–1503, 1982.

Rustgi, "Hereditary gastrointestinal polyposis and nonpolyposis syndromes," *New England Journal of Medicine* 331, 1694–1702, 1994.

Sachatello et al., "Generalized juvenile gastrointestinal polyposis," *Gastroenterology* 58(5):699–708, 1970.

Scott–Conner et al., "Familial juvenile polyposis: patterns of recurrence and implications for surgical management," *Journal of the American College of Surgeons* 181, 407–413, 1995.

Sekelsky, et al., "Genetic characterization and cloning of mothers against dpp, a gene required for decapentaplegic function in *Drosophila melanogaster*," *Genetics*, 139:1347, 1995.

Stemper et al., "Juvenile polyposis and gastrointestinal carcinoma," *Ann Intern Med* 83(5):639–646, 1975.

Thiagalingam et al., "Evaluation of candidate tumour suppressor genes on chromosome 18 in colorectal cancers," *Nature Genetics* 13, 343–346, 1996.

Thomas et al., "Genetic mapping of the hereditary mixed polyposis syndrome to chromosome 6q," *Am J Hum Genet* 58:770–776, 1996.

Veale et al., "Juvenile *polyposis coli*," *J Med Genet* 3:5–16, 1966.

Vogelstein et al., "Genetic alterations during colorectal–tumor development," *New England Journal of Medicine* 319(9):525–532, 1988.

Vogelstein, et al., "RAS gene mutations in childhood acute myeloid leukemia: a pediatric oncology group study," *Genes Chromosomes Cancer*, 2:159–162, 1990.

Walpole et al., "Juvenile polyposis: a case with early presentation and death attributable to adenocarcinoma of the pancreas," *Am J Med Genet* 32:1–8, 1989.

Watanabe et al., "Familial juvenile polyposis of the stomach," *Gastroenterology* 77:148–151, 1979.

Whitelaw et al., "Clinical and molecular features of the hereditary mixed polyposis syndrome," *Gastroenterology*, 112:327–334, 1997.

Wrana and Attisano, "MAD–related proteins in TGF–β signalling," *Trends Genet.*, 12:493–496, 1996.

Wrana and Pawson, "MAD about SMADs," *Nature*, 388:28–29, 1997.

Yoshida et al., "A case of generalized juvenile gastrointestinal polyposis associated with gastric carcinoma," *Endoscopy* 20, 33–35, 1988.

\* cited by examiner

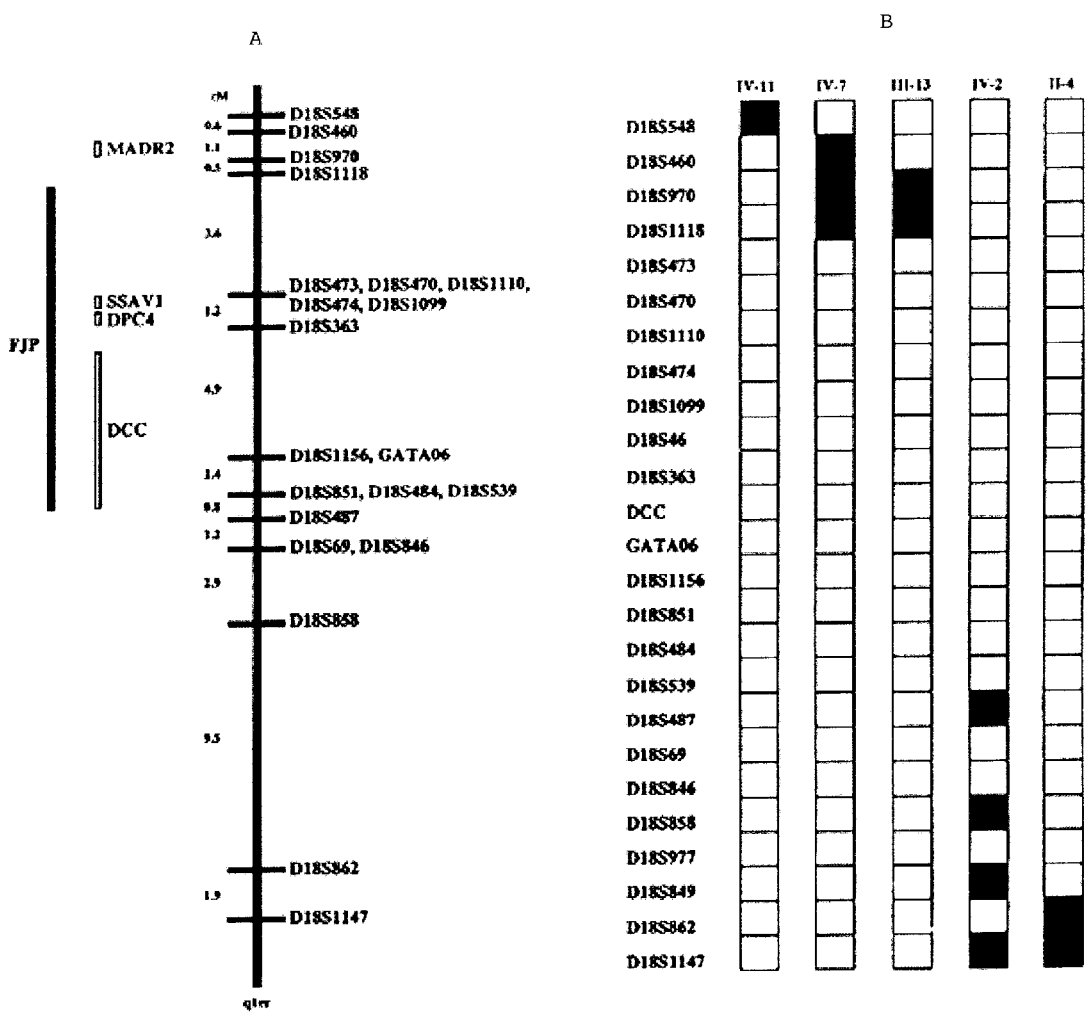
FIG. 2A-B

A
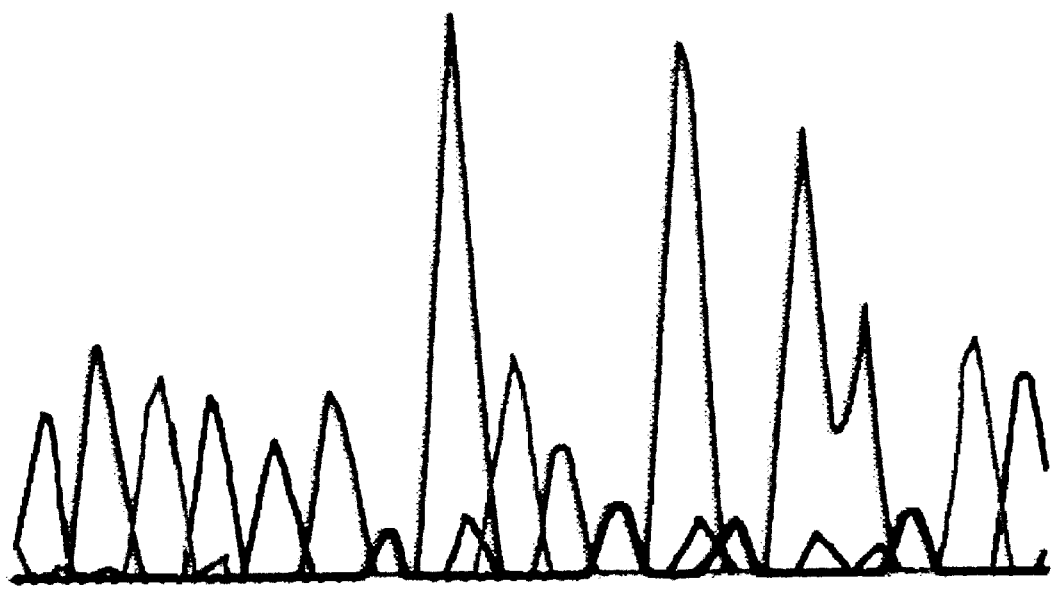
B
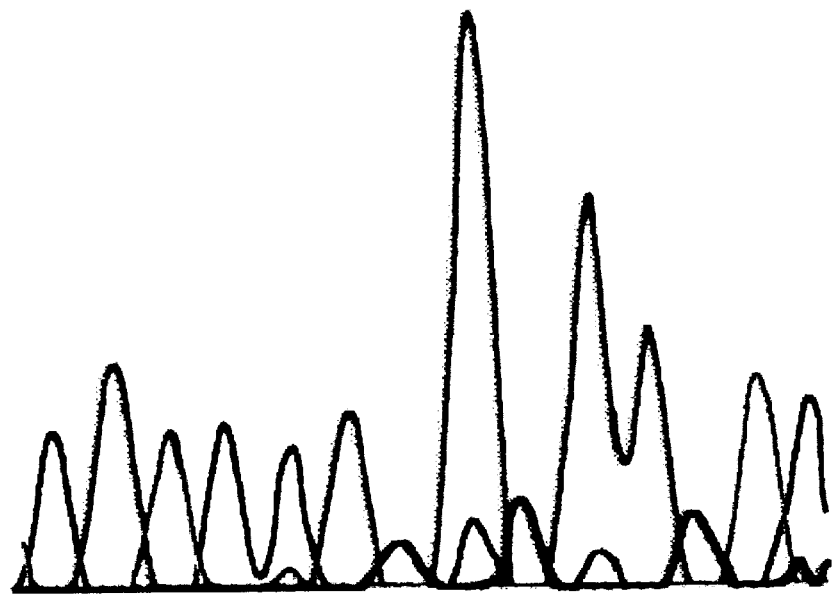
FIG. 3A-B

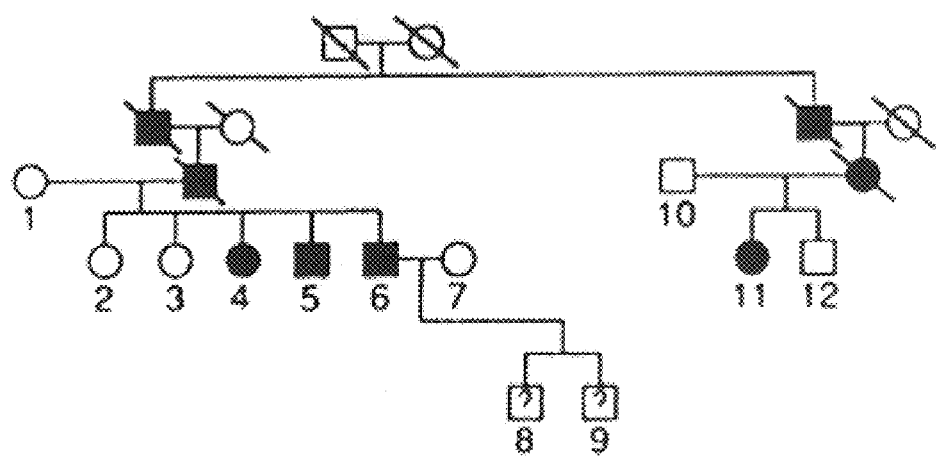
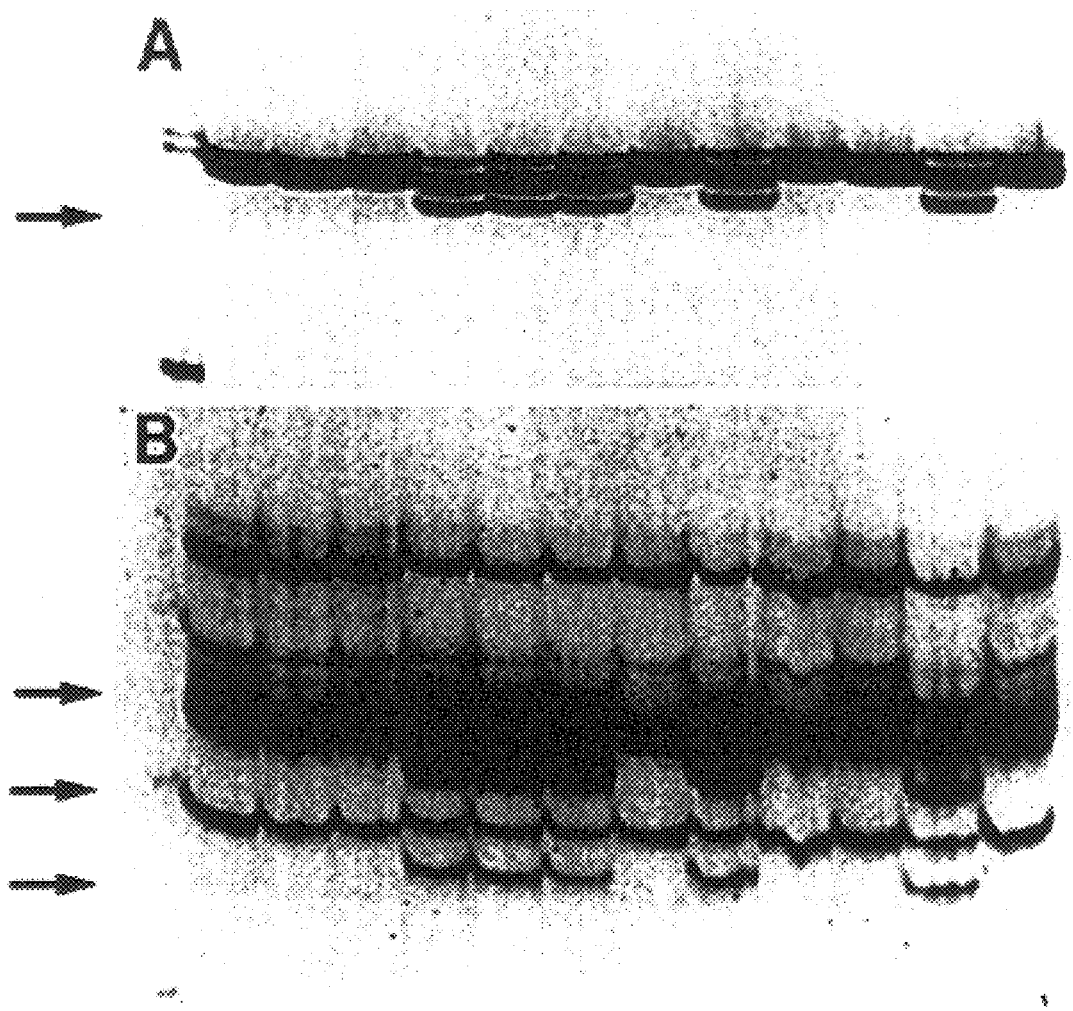
FIG. 4A-B

METHOD OF DIAGNOSING JUVENILE POLYPOSIS (JP)

This application claims priority to and specifically incorporates by reference. the content of U.S. Provisional Application Serial No. 60/085,312 filed May 13, 1998. The entire text of each of the above-referenced disclosure is specifically incorporated by reference herein without disclaimer.

BACKGROUND OF THE INVENTION

1. Field of the Invention

The present invention relates to the fields of oncology, genetics and molecular biology. More particular the invention relates to the identification of the gene responsible for familial juvenile polyposis. Defects in this gene are associated with a predisposition to gastrointestinal cancers.

2. Description of Related Art

Colorectal cancer is the second leading cause of cancer death in the United States. and was responsible for 57,407 deaths in 1994 (Landis et al., 1998). Approximately 5–10% of the nearly 131,600 new colorectal cancer cases each year will involve a clear heritable predisposition, of which the majority of cases involve hereditary non-polyposis colorectal cancer (HNPCC). About 1% of new colorectal cancers are related to inherited polyposis syndromes, which include familial adenomatous polyposis (FAP) and familial juvenile polyposis (FJP) (Rustgi, 1994).

Identification of the genes responsible for HNPCC and FAP have greatly increased our understanding of the molecular mechanisms contributing to the development of both familial and sporadic colorectal cancer. The intense studs of sporadic colorectal carcinogenesis over the last decade has shown that these tumors develop through the multi-step accumulation of different genetic mutations within colonic epithelial cells (Vogelstein et al., 1988). Genes known to be involved in this progression include APC and MCC on 5q21, KRAS2 on 12p12, p53 at 17p13, and several mismatch repair genes as seen in HNPCC (reviewed in Howe and Guillem, 1997).

Deletions on 18q21 also are quite common, occurring in approximately 75% of colorectal cancers (Vogelstein et al, 1988). Initial studies suggested that the tumor suppressor gene DCC (deleted in colorectal cancer)was the predisposing gene from this region (Fearon et al., 1990), but this has not been clearly established by further investigation.

Familial juvenile polyposis (JP) is an autosomal dominant condition characterized by multiple juvenile polyps of the gastrointestinal (GI) tract. Kindreds have been described in which there is involvement of the colon only juvenile polyposis *coli*, MIM 174900) (Veale et al., 1966; Grotsky et al, 1982; Rozen and Baratz 1982), the upper GI tract (Watanabe et al., 1979), and both upper and lower GI tracts (generalized polyposis) (Sachatello et al., 1970; Stemper et al., 1975; Jarvinen and Franssila 1984), although whether these are distinct clinical entities is not clear. Affected family members often present with blood per rectum or anemia in the 2d decade of life (Jass et al., 1988).

Microscopically, the polyps contain cystically dilated glands, abundant stroma. and an inflammatory infiltrate (Morson 1962). There have been many reports of patients with juvenile polyposis developing gastrointestinal malignancy, including colon cancer (Stemper et al, 1975; Liu et al., 1978; Goodman et al. 1979; Rozen and Baratz 1982;

Jarvinen and Franssila 1984; Ramaswamy et al, 1984; Baptist and Sabatini 1985; Jones et al, 1987; Bentley et al, 1989; Scott-Conner et al, 1995), stomach cancer (Stemper et al, 1975; Yoshida et al, 1988; Scott-Conner et al. 1995), and pancreatic cancer (Stemper et al., 1975; Walpole and Cullity 1989). Affected family members' risk of developing GI malignancy has been estimated to be from 9% (Jarvinen and Franssila 1984) to as high as 50% (Jass 1990). Development of adenocarcinoma has been hypothesized to begin with an adenomatous focus within a juvenile polyp, which later becomes dysplastic, and finally undergoes malignant transformation (Goodman et al., 1979; Jarvinen and Franssila 1984).

JP is a hamartomatous polyposis syndrome, as are Peutz-Jegher's Syndrome (PJS) and Cowden's disease (CD). Although the polyps in PJS are true hamartomata, some may undergo adenomatous change, and these family members are at increased risk for gastrointestinal malignancy. The PJS gene was mapped to chromosome 19p by comparative genomic hybridization and linkage (Hemminki et al., 1997; Mehenni et al., 1997), and germline mutations were identified in the serine threonine kinase gene LKBI (Hemminki et al., 1998). In CD, affected family members may develop multiple hamartomata of the skin, breast, thyroid, oral mucosa, or GI tract, and they are at risk for breast and thyroid malignancies. The gene for CD was localized to chromosome 10q22-23 by linkage (Nelen et al, 1996), and germline mutations in the PTEN gene have been found in affected family members (Liaw et al., 1997). A third entity, termed the "hereditary mixed-polyposis syndrome" (HMPS), differs from these syndromes in that affected family members have atypical juvenile polyps, colonic adenomas, and colorectal carcinomas. A gene for HMPS has been mapped to chromosome 6q by linkage (Thomas et al., 1996), and it remains uncertain whether HMPS is a distinct clinical syndrome or a variant of FJP (Whitelaw et al., 1997).

To date linkage studies in JP families have been limited, with one report excluding APC and MCC as the genes for FJP (Leggett et al., 1993). Other genetic studies, originally stimulated by the finding of an interstitial deletion at 10q22-24 in an infant with multiple colonic juvenile polyps and several congenital abnormalities (Jacoby et at., 1997b), have focused on the region of the PTEN gene. Evaluation for loss of heterozygosity in this region within juvenile polyps revealed somatic deletions within the lamina propria in 39 (83%) of 47 polyps derived from 13 unrelated patients with familial JP and 3 patients with sporadic juvenile polyps. These findings have been interpreted as evidence for a tumor-suppressor gene on 10q for FJP (termed "JPI") (Jacoby et al., 1997a), but a recent study of 14 FJP families found neither mutations in PTEN nor evidence of linkage to markers on 10q22-24 (Marsh et al, 1997). Analysis of an additional 11 cases of FJP also did not uncover mutations in the PTEN gene (Riggins et al., 1997). Lynch et al., (1977) reported one family thought to have both juvenile polyposis syndrome and CD as having a nonsense mutation in PTEN, and Olschwang et al., (1998) described three patients with juvenile polyposis as having PTEN mutations. Whether these four individuals should truly be considered as having juvenile polyposis rather than CD is not clear from these reports.

It is evident from the discussion presented above that FJP is a significant disease which has yet to be definitively linked to aberrations in a particular gene. The identification of such a gene will allow the determination the molecular basis of gastrointestinal polyposis predisposing to colorectal cancer, as well as presymptomatic diagnosis of family members at risk. Such a gene also may be involved in the genesis of sporadic colorectal cancers, and therefore its discovery could ultimately impact on the treatment of this large group of patients.

SUMMARY OF THE INVENTION

A particular objective of the present invention is to identify the JP gene in a large kindred with generalized juvenile polyposis and gastrointestinal cancer and to use the gene in various diagnostic and therapeutic applications.

Thus in a preferred embodiment, the present invention provides a method of diagnosing juvenile polyposis comprising the steps of obtaining a sample from a subject; and determining the loss or alteration of a functional SM4D4 gene in cells of the sample. In certain defined embodiments the sample may be selected from the group consisting of blood, buccal smear and amniocentesis sample. In still further embodiments, the sample may be a tissue or fluid sample. In preferred embodiments, the determining may comprise assaying for a nucleic acid from the sample. In still further embodiments, the determining may further comprise subjecting the sample to conditions suitable to amplify the nucleic acid.

In alternative preferred embodiments, the determining comprises contacting the sample with an antibody that binds immunologically to a SMAD4. In particularly preferred embodiments, the method further comprises subjecting proteins of the sample to ELISA. In particular aspects of the present invention, the method may comprise the step of comparing the expression of SMAD4 in the sample with the expression of SMAD4 in non-juvenile polyposis samples. In defined aspects of the invention, the comparison involves evaluating the level of SMAD4 expression. In other aspects the comparison involves evaluating the structure of the SMAD4 gene, protein or transcript. In more defined embodiments, the evaluating may comprise an assay selected from the group consisting of sequencing, wild-type oligonucleotide hybridization, mutant oligonucleotide hybridization, SSCP, PCR™, denaturing gradient gel electrophoresis and RNase protection. In other defined embodiments, the evaluating is wild-type or mutant oligonucleotide hybridization and the oligonucleotide is configured in an array on a chip or wafer.

In particularly defined embodiments, the juvenile polyposis sample comprises a mutation in the coding sequence of SMAD4. In other defined embodiments, the mutation produces a deletion mutant, an insertion mutant, a frameshift mutant, a nonsense mutant, a missense mutant or splice mutant. In particularly preferred embodiments, the mutation is a frameshift mutation. In still further defined embodiments, the mutation results in a premature termination of the SMAD4 gene product. In particularly preferred embodiments, the mutation may independently be in exon 9, exon 8, exon 5 or in a combination of exons of the DPC4 gene. In certain preferred embodiments, there is a frameshift that results from a deletion in codons 414 through to 416 of SMAD4. In other defined embodiments, the frameshift results in a STOP at codon 434 of wild-type SMAD4. In yet another alternative, the frameshift results from a deletion in codon 348. In still another alternative the frameshift results in a STOP at codon 350 of wild-type SMAD4. In further embodiments, the frameshift results from a deletion in codon 345. In yet another alternative, the frameshift results in a STOP at codon 382 to 383 of wild-type SMAD4. In another alternative, the frameshift results from an insertion in codon 229 through to 231. In defined embodiments, the frameshift may result in a STOP at codon 235 of wild-type SMAD4. In other embodiments, the mutation is a missense mutation, wherein the mutation is an A to C substitution at codon 352, converting a tyrosine to a serine. In other embodiments, the mutation is a nonsense mutation, wherein the mutation is a G to C substitution at codon 177, converting a serine to a stop codon.

Also contemplated by the present invention is a method for altering the phenotype of a cell in a subject having juvenile polyposis comprising the step of contacting the cell with SMAD4 under conditions permitting the uptake of the SMAD4 by the cell. In particularly preferred embodiments, the cell is derived from a gastrointestinal cell. In more particular embodiments, the phenotype is selected from the group consisting of proliferation, migration, contact inhibition, soft agar growth and cell cycling. In particularly defined aspects of the invention, the SMAD4 may be encapsulated in a liposome.

In yet another aspect of the present invention there is provided a method for altering the phenotype of a cell in a subject having juvenile polyposis comprising the step of contacting the cell with a nucleic acid (i) encoding SMAD4 and (ii) a promoter active in the cell, wherein the promoter is operably linked to the region encoding the SMAD4, under conditions permitting the uptake of the nucleic acid by the cell. In particular aspects the cell may be derived from a gastrointestinal cell. In other embodiments, the cell is a tumor cell. In certain defined embodiments, the nucleic acid may comprise a viral vector selected from the group consisting of retrovirus, adenovirus, adeno-associated virus, vaccinia virus and herpesvirus. In particular embodiment, the nucleic acid is encapsulated in a viral particle.

Also contemplated is a method for treating juvenile polyposis comprising the step of contacting a cell within a subject with SMAD4 under conditions permitting the uptake of the SMAD4 by the cell. In particular preferred embodiments, the subject is a human.

In yet another embodiment, the present invention contemplates a method for treating juvenile polyposis in a subject comprising the step of contacting a cell within the subject with a nucleic acid (i) encoding SMAD4 and (ii) a promoter active in the cell, wherein the promoter is operably linked to the region encoding the SMAD4, under conditions permitting the uptake of the nucleic acid by the cell. In particular aspects of the present invention the cell may be derived from a tissue selected from the group consisting of skin, muscle, fascia, brain, prostate, breast, endometrium, lung, head & neck, pancreas, small intestine, blood cells, liver, testes, ovaries, colon, rectum, skin, stomach, esophagus, spleen, lymph nodes, bone marrow and kidney.

In other embodiments, it is contemplated that detecting SMAD4 expression levels can be utilized prognostically in identifying colorectal cancer.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2A and FIG. 2B. Schematic representation of STRPs and genes from 18q21 (FIG. 2A) and recombination analysis of key affected individuals (FIG. 2B). STRPs are listed in their map order, based on the Center for Medical Genetics map; markers D18S977 and D18S849 lie between D18S858 and D18S862 (Whitehead Institute for Biomedical Research/MIT Center for Genome Research); and D18S46 lies between DPC4 and D18S363 (Hahn et al., 1996a). The locations of MADR2, SSAV1, DPC4, and DCC are representations derived from physical mapping data (Eppert et al., 1996); the lengths of the corresponding bars shown for the map at left do not necessarily reflect the size of each gene. To the right, informative recombination events in affected individuals that define the interval of the JP gene are depicted as blackened boxes; unblackened boxes designate noninformative meioses. These data suggest that the JP gene lies between the markers D18S1118 and D18S487.

FIG. 3A and FIG. 3B. Sequences of the wild-type (FIG. 3A) and mutant (FIG. 3B) alleles of SMAD4 exon 9 (nucleotides 1365 to 1382) from an affected member of the Iowa JP family. The rectangle indicates the 4 base-pairs deleted in the mutant allele (arrow).

FIG. 4A and FIG. 4B. Denaturing (FIG. 4A) and nondenaturing gels (FIG. 4B) of Iowa JP kindred family members, showing the SMAD4 exon 9 PCR product. Affected individuals 4, 5, 6, and 11, as well as one at risk (8), all have an extra band on denaturing gels that is produced by the 4 base-pair deletion. The mutant allele is also seen as a shift by SSCP (FIG. 4B).

DESCRIPTION OF ILLUSTRATIVE EMBODIMENTS

Figure 1:
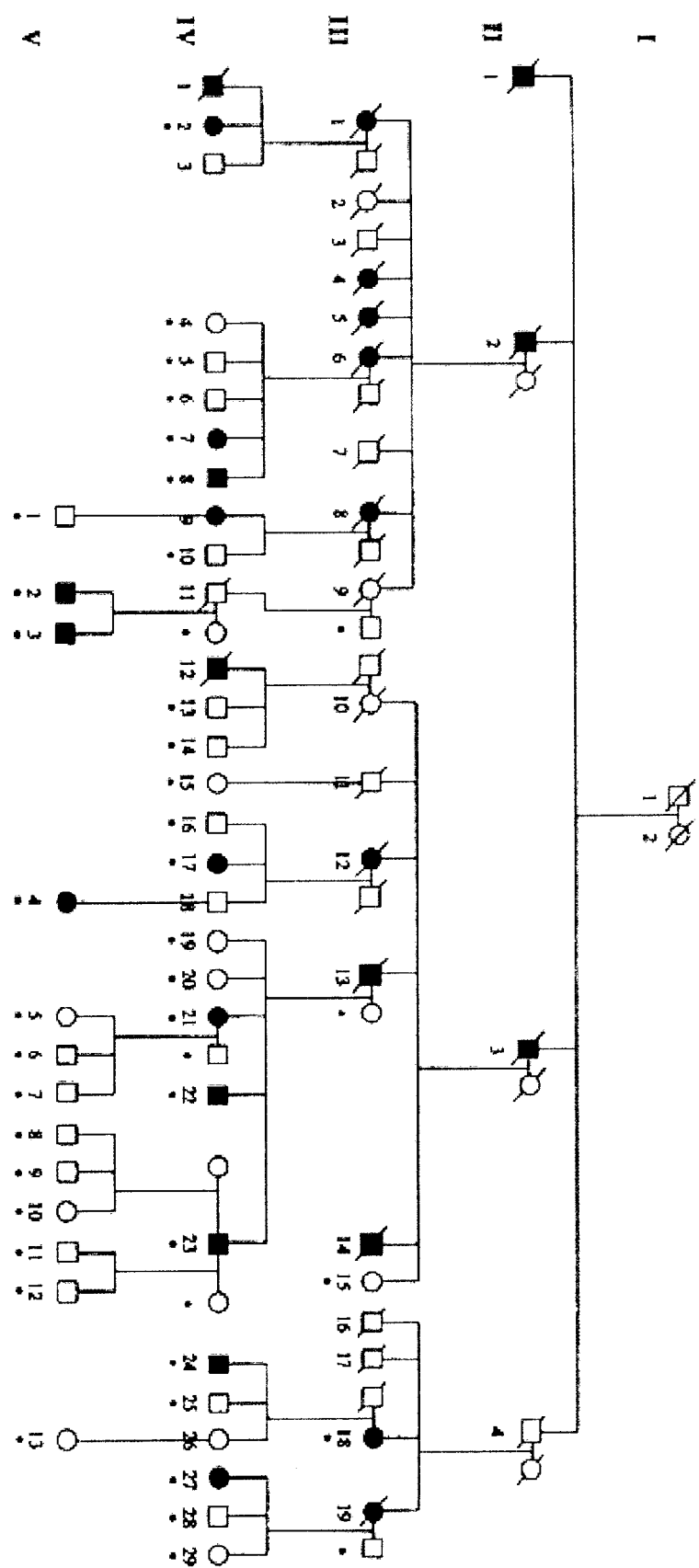
FIG. 1 Pedigree of a five-generation American midwestern FJP family (the Iowa FJP kindred). Blackened symbols designate affected family members; unblackened symbols indicate unaffected individuals or those with unknown affection status; genotyping was performed on those marked by asterisks (*).

Familial juvenile polyposis (JP) is a hamartomatous polyposis syndrome in which affected family members develop upper and lower gastrointestinal juvenile polyps and are at increased risk for gastrointestinal cancer. Other hamartomatous polyposis syndromes include Peutz-Jegher's Syndrome (PJS) and Cowden's Disease (CD). Although the genes for PJS and CD have been mapped to chromosome 19p (Hemminki et al., 1997; Hemminki et al, 1998; Mehenni et al., 1997), and 10q respectively, (Nelen et al., 1996; Liaw et al., 1997) there has been no definite linkage of JP to a particular gene or chromosomal region. A third entity, termed the "hereditary mixed-polyposis syndrome" (HMPS), differs from PJS and CD syndromes in that affected family members have atypical juvenile polyps, colonic adenomas, and colorectal carcinomas. A gene for HMPS has been mapped to chromosome 6q by linkage (Thomas et al., 1996), and it remains uncertain whether HMPS is a distinct clinical syndrome or a variant of FJP (whitelaw et al., 1997).

Thus far, linkage studies in FJP families have been limited, merely resulting in the exclusion of APC and MCC as the genes for FJP (Leggett et al, 1993). Likewise, other genetic studies, (Jacoby et al., 1997b), focused on the region of the PTEN gene have shown that there is some evidence for a tumor-suppressor gene on 10q for FJP (termed "JPI") (Jacoby et al., 1997a), but a recent study of 14 JP families found neither mutations in PTEN nor evidence of linkage to markers on 10q22-24 (Marsh et al., 1997). Analysis of an additional 11 cases of JP also did not uncover mutations in the PTEIV gene (Riggins et al., 1997). Additionally, it appears that the clinical manifestation of polyps in patients with PTEN mutations are actually more likely to be attributable to CD rather than JP (Lynch et al., 1997; Olschwang et al., 1998).

1. The Present Invention

A particular objective of the present invention was to identify by linkage analysis the chromosomal locus of the JP gene in a large kindred with generalized juvenile polyposis and gastrointestinal cancer. Further, once the FJP gene has been definitively identified it will be possible to identify mutations that lead to or predispose an individual to FJP and therefor provide the motivation for identifying methods and compositions for ameliorating the disease.

The studies presented herein found no evidence for linkage with markers near MSH2, MLH1, MCC, APC, HMPS, CDKN2A, JP1, PTEN, KRAS2, TP53, or LKB1. Linkage to FJP was established with several markers from chromosome 18q21.1. The maximum LOD score was 5.00. with marker D18S1099 (recombination fraction of 0.001). Analysis of critical recombinants places the FJP gene in an 11.9-cM interval bounded by D18S1118 and D18S487, a region that also contains the tumor-suppressor genes DCC and DPC4.

Additional studies showed for the first time, that the gene responsible for a malignant phenotype in JP is, in fact. the DPC4, also known as SMAD4. In particular it is shown that a subset of JP families carry germline mutations in SMAD4/DPC4, which encodes a critical cytoplasmic mediator in the transforming growth factor-β (TCF-β), activin and bone morphogenic protein (BMP) signaling pathways. The mutant SMAD4 proteins are predicted to be truncated at the carboxyl-terminus and lack sequences required for normal function. These results confirm an important role for SMAD4 in the development of JP and gastrointestinal tumors. Methods and compositions for the diagnosis and treatment of such disorders are presented herein below.

2. SMAD4/DPC4

DPC4 is a tumor suppressor gene, located on chromosome 18q21.1, centromeric to DCC, a gene located in the region of 18q LOH seen in sporadic colorectal and pancreatic cancers. As described herein DPC4 (deleted in pancreatic cancer locus 4) is the same as SMAD4 and the nomenclature can and is used interchangeably. DPC4 is described in U.S. Pat. No. 5,712,097, incorporated herein by reference in its entirety. More particularly, U.S. Pat. No. 5,712,097, discloses a cDNA sequence for DPC4 which comprises a 1656 bp transcribed sequence which encodes a predicted 552 amino acid coding sequence. The gene is said to be characterized by multiple stop codons in all three reading frames 5' to the putative ATG start site; multiple stop codons in the non-coding frames 3' to the start site; ten splice sites (eleven exons) in the longest possible reading frame; and a terminal TGA stop codon-in-frame, as well as stop codons nearby in the other two frames.

DPC4 polypeptide (SEQ ID NO:4) has amino acid sequence similarity to the D. melanogaster Mothers against dpp (Mad) gene as well as to the C. elegans Mad homologs smad-2, smad-3, smad-4 (CEM-1, CEM-2, CEM-3, respectively). The highest degree of similarity is found among exons 1, 2, and 11 of DPC4 and lesser similarity is found for exons 8, 9, and 10. The decapentaplegic (dpp) gene encodes a growth factor belonging to the transforming growth factor-β (TGF-β) superfamily and seems to play a central role in multiple cell-cell signaling events throughout development (Hursh, et al., 1993). A stop mutation responsible for a phenotype resembling dpp mutants is located at codon 417 within a conserved region of the Mad gene, matches the homologous position of the frameshift mutation found in DPC4, and is located one codon 5' to the position of a nonsense mutation found in DPC4 (Sekelsky et al, 1995).

DPC4 is a member of the SMAD family of genes, which code for cytoplasmic mediators in the transforming growth factor-β (TGF-β) signaling pathway (Wrana and Attisani, 1996). This pathway mediates growth inhibitory signals from the cell surface to the nucleus. Upon activation by TGF-β or related ligands, serine/threonine kinase receptors phosphorylate various SMADs, which then form heteromeric complexes with SMAD4 in the cytoplasm (Lagna et al., 1996). These complexes then migrate to the nucleus, where they are thought to regulate transcription through association with various DNA-binding proteins (Wrana and Pawson, 1997). The growth inhibitory effect of TGF-β on pancreatic cancer cell lines requires functional DPC4 (Grau et al., 1997).

DPC4 (SEQ ID NO:3) is a highly conserved gene which is frequently inactivated during the development of pancreatic and other types of carcinomas including bile duct cancer, bladder cancer and colorectal cancer. In a particular study, DPC4 was implicated in the multistep carcinogenesis of biliary tract carcinoma (Hahn el al, 1998). A search for mutations in COOH-terminal domain of DPC4 (exons 8-11) revealed that 16% of primary biliary tract carcinomas had point mutations in the DPC4 sequence. Interestingly, inactivation of DPC4 was especially common in carcinomas originating from the common bile duct, suggesting an important role for DPC4 in the development of this subtype of biliary tract tumor. In a comparative study, it was found that the DPC4 is rarely if ever mutated during prostatic oncogenesis, whereas inactivation of this gene may contribute to the genesis of a subset of colorectal carcinomas (MacGrogan et al. 1997). Tumor suppressive qualities of an intact DPC gene product have also been demonstrated in head and neck squamous carcinoma cells whereas the gene is shown to be deleted in tumorigenic clones (Reiss et al., 1997).

The DPC4 gene is homozygously deleted in approximately 30% of pancreatic carcinomas, and gene mutations are seen in 22% of pancreatic tumors which do not have homozygous deletions (Hahn et al., 1996). DPC4 was also found to be lost or altered in 5 of 18 (28%) colorectal carcinoma cell lines (Thiagalingam et al., 1996). The latter study defined the minimally lost region in 55 colorectal carcinoma cell lines to span the 16 cM interval between D18S535 and D18S858, which contains both the DCC and DPC4 genes.

Despite these studies showing that SMAD4 is a tumor suppressor in a variety of cancers, there is equally compelling evidence that suggest that DPC4 is not tumor suppressive in all cancers. One such study which used eleven separate lung tumors to look for the presence of mutations in SMAD4 found that SMAD4 was not a lung tumor suppressor (Devereux et al., 1997). Another study that analyzed patients presenting with prostate cancer concluded that the inactivation of one or more putative tumor suppressor genes on 18q21 other than DCC or DPC4 were responsible for the progression of human prostatic cancer. As there is a great deal of evidence that points to allelic loss on chromosome 18q as being involved in the progression of gastric carcinoma, a group recently analyzed the role of DPC4 in gastric carcinoma. DPC4 gene mutations and allelic status-at 18q21 in 30 primary gastric carcinomas and 5 gastric carcinoma cell lines were tested. Polymerase chain reaction single-strand conformation polymorphism and sequencing analyses revealed no DPC4 mutations in any of the primary tumors or cell lines. This strongly suggests that the target gene for loss on 18q is not DPC4 and that the true tumor suppressor gene, encoded near DPC4, has yet to be identified (Nishizuka et al., 1997).

Clearly, there is a great deal of disparate evidence about the involvement of DPC4 in various cancers and in particular in gastrointestinal cancer. The present invention definitively identifies the 18q21.1 locus as the chromosomal locus for juvenile polyposis. Further, the present invention clearly demonstrates that mutations in DPC4 result in JP and predisposes an individual to colorectal, pancreatic and gastric carcinoma. In fact, it is demonstrated in one embodiment of the present invention, that a loss in DPC4 gene expression is highly indicative of colorectal tumorigenesis.

3. Juvenile Polyposis and Gastrointestinal Malignancy

The inherited polyposis syndromes can be divided into the adenomatous (FAP) and hamartomatous types, the latter of which includes familial juvenile polyposis (JP), Peutz-Jeghers syndrome (PJ), and Cowden disease (CD). The polyps in PJ patients are true hamartomata, but these may undergo adenomatous change and evolve into gastrointestinal malignancies. In CD, family members may develop multiple hamartomata of the skin, breast, thyroid, oral mucosa, or GI tract, and these individuals are at risk for breast and thyroid malignancies. Of these three syndromes, however, the strongest predisposition to gastrointestinal malignancy is seen in JP, which remains the last of these syndromes in which the gene has not been identified.

JP is an autosomal dominant condition characterized by juvenile polyps of the stomach small intestine, and/or colon in affected family members. It has been suggested that there are actually three forms of JP, with polyps developing in the colon, the stomach, or generalized throughout the GI tract (Goodman et al., 1979). It is also possible that these entities represent variable expressivity or different alterations of the same gene (Rustigi, 1994). In the past, many patients with JP presented with advanced cancers of the gastrointestinal tract, but now most are diagnosed by endoscopy following episodes of gastrointestinal bleeding, usually occurring within the first two decades of life. Surgical specimens from JP patients reveal multiple juvenile polyps, which have a unique microscopic appearance. Upon cursory inspection these polyps appear hyperplastic, but closer examination reveals dilated submucosal cystic spaces lined with glandular epithelium, an overabundance of stromal tissue, and infiltration of inflammatory cells.

Thus, juvenile polyposis may be diagnosed when a relatively old and asymptomatic parent is screened colonoscopically and the smallest number of polyps found on this basis is five. These data allow a working definition of juvenile polyposis to be formulated: (1) more than five juvenile polyps of the colorectum; and/or (2) juvenile polyps throughout the gastrointestinal tract; and/or (3) any number of juvenile polyps with a family history of juvenile polyposis.

In contrast to the relatively rare familial form of juvenile polyposis, sporadic juvenile polyps are the most common type of polyps seen in children, and may occur in 1–2% of the population (Jarvinen, 1993). These sporadic polyps do not predispose to malignancy, are usually solitary, slough at an early age and generally do not recur. Based upon the benign course of patients with sporadic juvenile polyps, polyps in patients with familial JP were originally thought to be hamartomata without malignant potential. However, in 1975, investigators at the University of Iowa described a kindred in which 10 family members had been diagnosed with juvenile polyposis of the upper and/or lower gastrointestinal (GI) tract, and 11 members had developed GI carcinomas (Stemper et al., 1975). Since this time, there have been many reports of GI malignancy developing in patients with juvenile polyposis, including colon cancer (Goodman et al., 1979, Stemper et al., 1975; Liu et al, 1978; Rozen and Baratz, 1982; Ramaswamy et al., 1984; Jarvinen and Franssila, 1984; Baptist and Sabatini, 1985; Jones et al., Bentley et al., 1989; Scott-Conner et al., 1995). stomach cancer (Stemper et al., 1975, Scott-Conner et al, 1995; Yoshida et al., 1988), and pancreatic cancer (Stemper et al., 1975; Walpole and Cullity, 1989). The risk of developing GI malignancy in affected family members has been estimated to be anywhere from 9% (Jarvinen and Franssila, 1984) to as high as 68% (Jass, 1994). The progression to adenocarcinoma has been hypothesized to begin with an adenomatous focus within a juvenile polyp, which later becomes dysplastic, and finally undergoes malignant transformation (Goodman et al, 1979, Jarvinen and Franssila, 1984).

This strong association of gastrointestinal carcinoma with juvenile polyposis suggests that the germline mutations predisposing to these unusual polyps also may play an important role in the development of sporadic gastrointestinal cancers, and in particular, colorectal and gastric cancer. By using a unique resource namely those individuals with a heritable predisposition to these tumors, the present inventor has been able to identify a gene which predisposes an individual to gastrointestinal cancer. The autosomal dominant inheritance seen in these kindreds allowed for a molecular genetic approach for the chromosomal localization of the gene, and the detection of mutations in candidate gene which segregate with the disease phenotype. The discovery of DPC4 as the JP gene, described herein, will benefit kindred members by making presymptomatic genetic testing possible, and also may uncover a new pathway involved in the multi-step progression to colorectal cancer.

I. Genetic Studies of FJP Families

The majority of the hamartomatous polyposis syndromes have been genetically mapped or their predisposing genes have been identified, with the exception of FJP. The PJ gene has been mapped to chromosome 19p by comparative genomic hybridization and linkage (Hemminki et al, 1997), and germline mutations identified in the serine threonine kinase gene LKB1 (Hemminki et al., 1998). The gene for CD was localized to chromosome 10q22-23 by linkage (Nelen et al, 1996), and germline mutations in the PTEN gene were later described in affected family members (Liaw et al., 1997). A third entity, termed the hereditary mixed polyposis syndrome (HMPS), differs in that affected family members have polyps similar to (but distinct from) juvenile polyps, as well as colonic adenomas and colorectal carcinomas. A gene for HMPS has been mapped to chromosome 6q by linkage (Thomas et al, 1996), and it remains uncertain whether HMPS is a distinct clinical syndrome or a variant of FJP (Whitelaw et al, 1997).

In contrast, linkage studies in FJP families have been limited, with one report excluding APC and MCC as the genes for FJP (Leggett et al., 1993). Other genetic studies in JP have focused on the CD locus region on 10q, stimulated by the finding of an interstitial deletion at 10q22-q24 in an infant with multiple colonic juvenile polyps and several congenital abnormalities (Jacoby et al., 1997a). Evaluation of juvenile polyps for loss of heterozygosity in this region revealed somatic deletions within the lamina propria in 39 of 47 polyps (83%) derived from 13 unrelated patients with FJP and 3 with sporadic juvenile polyps. These findings have suggested the presence of a tumor suppressor gene on 10q involved in JP (termed JPI)(Jacoby et al., 1997b). A recent report described 3 patients with juvenile polyposis who had germline mutations in the PTFN gene, but none were described as having a family history of juvenile polyposis (Olschwang et al., 1998). Another recent study of 14 JP families found neither mutations in PTEN nor evidence of linkage to markers on 10q22-24(Marsh et at., 1997).

The present invention describes the linkage of the JP gene to markers on chromosome 18q21 in-the kindred originally described by Stemper et al.(1975), and found no evidence for linkage to markers from a variety of other chromosomal regions predisposing to sporadic colorectal cancer or polyposis, including 10q22-24. These data suggest genetic heterogeneity for the juvenile polyposis syndromes, and for the large family predisposed to GI carcinoma, linkage to the. same region commonly deleted in sporadic colorectal (Fearon et al, 1990) and pancreatic carcinoma (Hahn et al., 1996).

These findings have important ramifications for the identification of the tumor suppressor gene from 18q21 which plays a role in the development of these sporadic tumors. Although the gene involved in colorectal cancer was originally thought to be DCC (Fearon et al., 1990), subsequent studies have not provided compelling proof of mutations within the DCC gene. Part of this may be due to the large size of this gene, which spans approximately 1.4 Mb in genomic DNA and contains 29 exons (Cho et al, 1994). DCC has been shown to encode for a netrin receptor (Keino-Masu et al,. 1996), and transgenic mice lacking a functional DCC gene manifest defects in commissural axon projections (Fazeli et al., 1997). These mice do not appear to have an increased rate of intestinal tumors, and therefore the loss of DCC expression commonly seen in colorectal and pancreatic cancers may actually be related to changes in a linked gene (Fazeli et al, 1997).

Also mapping to the same region as DCC is DPC4 (deleted in pancreatic cancer 4), a member of the Mad gene family, which is involved in signal transduction of serine threonine kinase receptors (Hahn et al., 1996b). Interestingly, the gene for Peutz-Jeghers syndrome is caused by mutations in a serine threonine kinase gene (Hemminki et al., 1998). The association of gastrointestinal cancers with JP, and the genetic linkage of the FJP gene to the same interval on chromosome 18q21 frequently deleted in colorectal and pancreatic carcinomas suggests that identification of the JP gene could lend significant insight into the molecular mechanisms involved in these cancers. Here it is shown that a subset of JP families carry germline mutations in DPC4. The mutant DPC4 proteins are predicted to be truncated at the carboxy-terminus and lack sequences required for normal function. These results confirm an important role for DPC4 in the development of JP and gastrointestinal tumors.

4. Diagnosing Malignancy Involving DPC4

The present inventor has determined that alterations in DPC4 are associated with the formation of juvenile polyposis (JP). Further, it is known that juvenile polyposis predisposes an individual to gastrointestinal malignancy as described herein above. Therefore. DPC4 and the corresponding gene may be employed as a diagnostic or prognostic indicator of JP in general, and more particularly, of familial JP. More specifically, point mutations, deletions, insertions or regulatory perturbations relating to DPC4 cause JP and/or promote cancer development, cause or promote polyposis or tumor progression at a primary site, and/or cause or promote metastasis.

The present invention contemplates further the diagnosis of colorectal cancer by detecting. changes in the levels of SMAD4 expression. In one embodiment. SMAD4 immunostaining of colorectal samples utilizing an antibody recognizing the C-terminal end of the SMAD4 polypeptide, demonstrates a highly significant tendency for loss of SMAD4 expression during colorectal tumorigenesis.

I. Genetic Diagnosis

One embodiment of the instant invention comprises a method for detecting variation in the expression of DPC4. This may comprises determining that level of DPC4 or determining specific alterations in the expressed product. Obviously. this sort of assay has importance in the diagnosis of related cancers. Such cancer may involve cancers of the brain (glioblastomas, medulloblastoma; astrocytoma, oligodendroglioma, ependymomas), lung, liver, spleen, kidney, pancreas, bile ducts, ampalla of Vorter, small intestine, blood cells, lymph nodes, colon, rectum, breast, endometrium, stomach, prostate, testicle, ovary, skin, head and neck, esophagus, bone marrow, blood or other tissue. In particular, the present invention relates to the diagnosis of juvenile polyposis which may or may not ultimately lead to gastrointestinal cancer.

The biological sample can be any tissue or fluid. Various embodiments include cells of the skin, muscle, fascia, brain, prostate, breast, endometrium, lung, head & neck, pancreas, small intestine, blood cells, liver, testes, ovaries, colon, rectum, skin. stomach, esophagus, spleen, lymph nodes, bone marrow or kidney. Other embodiments include fluid samples such as peripheral blood, lymph fluid, ascites, serous fluid, pleural effusion, sputum, cerebrospinal fluid, lacrimal fluid, stool urine or amniotic fluid.

Nucleic acids used are isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA (cDNA). In one embodiment, the RNA is whole cell RNA; in another, it is poly-A RNA. Normally, the nucleic acid is amplified.

Depending on the format, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively. the detection may involve indirect identification of the product via chemiluminescence, radioactive scintigraphy of radiolabel or fluorescent label or even via a system using electrical or thermal impulse signals (Affymax Technology; Bellus, 1994).

Following detection, one may compare the results seen in a given patient with a statistically significant reference group of normal patients and patients that have DPC4-related pathologies. In this way, it is possible to correlate the amount or kind of DPC4 detected with various clinical states.

Various types of defects have been identified by the present inventors. Thus, "alterations" should be read as including deletions, insertions, point mutations and duplications. Point mutations result in stop codons, frameshift mutations or amino acid substitutions. Somatic mutations are those occurring in non-germline tissues. Germ-line tissue can occur in any tissue and are inherited. Mutations in and outside the coding region also may affect the amount of DPC4 produced, both by altering the transcription of the gene or in destabilizing or otherwise altering the processing of either the transcript (mRNA) or protein.

Many of the genes predisposing to the development of cancer are tumor suppressor genes, and conform to the two-hit hypothesis as described by Knudson for retinoblastoma (Knudson et al., 1975). Affected individuals from families with germline mutations in a tumor suppressor gene are born with a predisposition to cancer in all cells owing to the germline defect, and tumors develop after mutation or deletion of the remaining normal copy of the gene in a somatic cell. This results in loss of a functional protein whose role normally is to hold neoplastic transformation in check within the cell. Since many of these somatic events are deletions, mapping of these deletions helps to establish the minimal common region of overlap, which defines the region containing the tumor suppressor gene. Thus, a cell takes a genetic step toward oncogenic transformation when one allele of a tumor suppressor gene is inactivated due to inheritance of a germline lesion or acquisition of a somatic mutation. The inactivation of the other allele of the gene usually involves a somatic micromutation or chromosomal allelic deletion that results in loss of heterozygosity (LOH). Alternatively, both copies of a tumor suppressor gene may be lost by homozygous deletion.

The inventor mapped a gene predisposing to JP to chromosome 18q21. 1, between markers D18S118 and D18S487 (Howe et al.), an interval that contains the two putative tumor suppressor genes DCC and SMAD4 (Eppert et al., 1996). The high incidence of colorectal cancer (as well as one case of pancreatic cancer) in affected members of the JP kindred displaying 18q21 linkage (the Iowa JP kindred) (Stemper et al., 1975), led to the idea that one of these tumor suppressor genes could be the gene predisposing to JP. The inventor sequenced genomic polymerase chain reaction (PCR) products generated from one affected individual for each exon of DCC and DPC4. After sequencing 14 DCC exons and all 11 DPC4 exons, the inventors detected a 4 base-pair deletion in exon 9 of DPC4. The inventor subcloned the exon 9 PCR product from this patient and sequenced the individual alleles. One allele was the wild type and the other had a 4 base-pair deletion (FIG. 3) between nucleotides 1372 and 1375 (codons 414 to 416) of the cDNA sequence (GenBank Accession No. U44378 (Hahn et al., 1996)). This deletion caused a frameshift that creates a new stop codon at the end of exon 9 (nts 1432 to 1434 of the wild-type sequence, codon 434).

Figure 5:
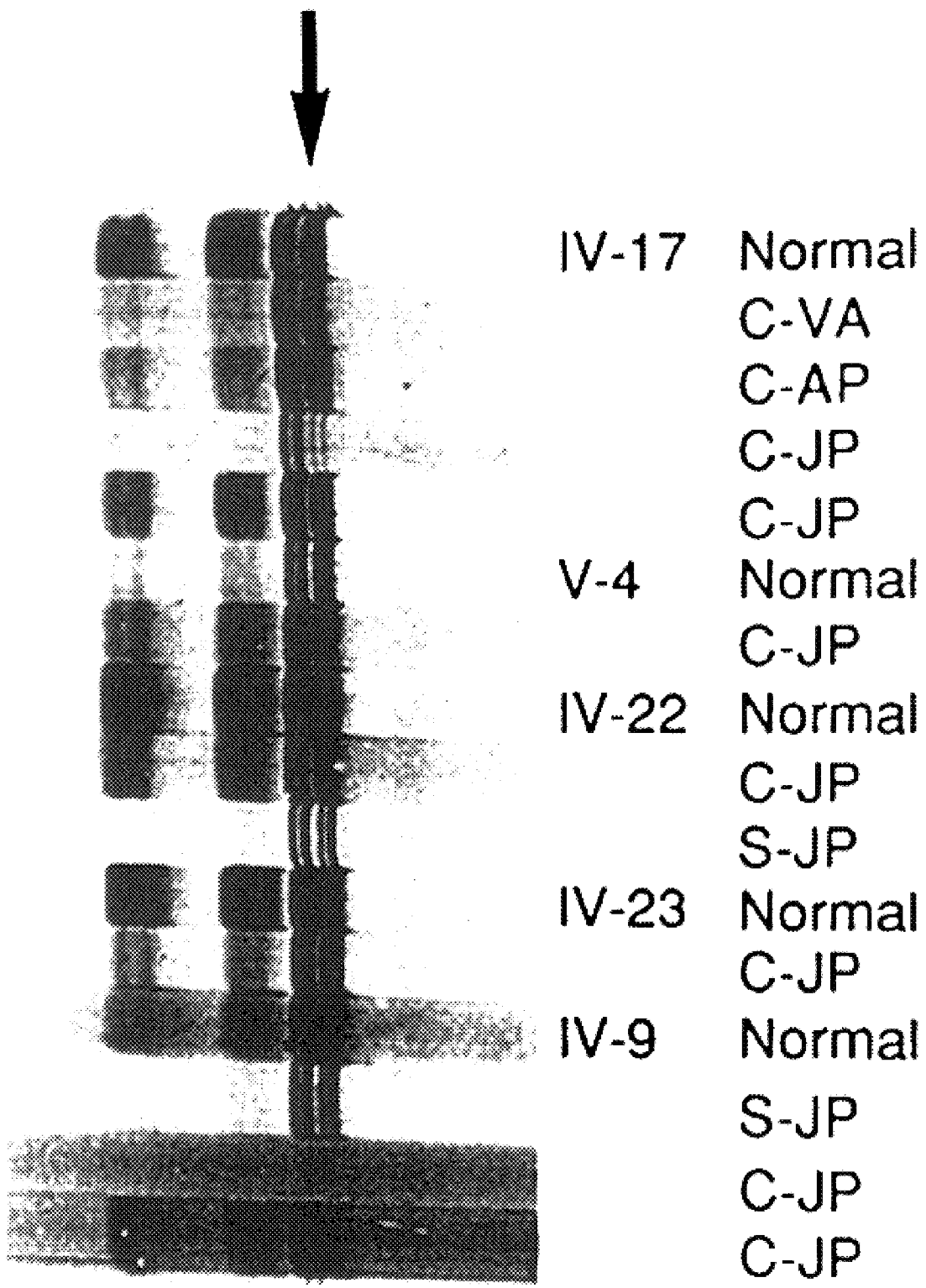
FIG. 5. PCR amplification of SMAD4 exon 9 from microdissected polyps. Pedigree numbers correspond to affected individuals as described in the Examples. Loss of the wild-type allele is seen in a juvenile polyp from patient IV-17 (arrow). DNA was extracted from paraffin-embedded polyps after microdissection. Amplification of exon 9 was performed using the primers 5'-TAGGCAAAGGTGTGCAGTTG-3' (SEQ ID NO:1) and 5'-TGCACTTGGGTAGATCTYATGAA-3' (SEQ ID NO:2), which generate a 152 bp product from within the exon. C-colon; S-stomach; VA-villous adenoma-AP=adenomatous polyp; JP=juvenile polyp.

The inventor further analyzed exon 9 of DPC4 from all 46 members of the Iowa JP kindred by PCR amplification and denaturing polyacrylamide gel electrophoresis. The altered allele was present in all 13 affected individuals, none of 7 spouses, and 4 of 26 individuals at risk (two-point lod score of 5.79, 0=0.00). This altered allele was also readily observed on SSCP gels (FIG. 4). To exclude the possibility that this alteration represented a polymorphism, the inventors amplified exon 9 from 242 unrelated individuals (484 chromosomes). The altered allele was not observed in this population. DNA extracted from GI polyps was also used to amplify DPC4 exon 9. This analysis revealed loss of the wild-type allele in 1 of 11 tumors derived from 5 affected individuals (FIG. 5).

Eight additional unrelated JP patients were subsequently analyzed for mutations of all exons of DPC4 by SSCP and genomic sequencing (Table 6). Two JP kindreds were found which segregated a similar 4-base-pair deletion in exon 9. Due to the nature of the sequence in this region, these deletions can begin at any of four consecutive nucleotides and result in the same mutant sequence and new stop codon. A patient with colonic and gastric juvenile polyposis (whose father has a history of GI symptoms but has not been evaluated clinically) was found to have a 2-base-pair deletion in exon 8 of SMAD4, at nts 1170–1171 (codon 348). This deletion causes a frameshift that creates a stop codon at nts 1178–1180 (codon 350). Another patient diagnosed with 30–40 colonic juvenile polyps at age 6 but with no family history of JP (four siblings and both parents unaffected) was found to have a 1-base-pair insertion between nts 815–820 of exon 5; this change added a guanine to a stretch of six sequential guanines in the wild-type sequence, and created a frameshift and a new stop codon at nucleotides 830–832 (codon 235). A family with two affected members, one with 10–50 juvenile polyps and the other with less than 10 polyps as well as one member having colorectal and pancreatic cancer, were found to have an A to C substitution at nucleotide 1186 (exon 8, codon 352), resulting in the conversion of a tyrosine into a serine. Another patient with a sporadic case of JP with 10 to 50 polyps in both the stomach and large intestine, was found to have a G to C substitution at nucleotide 661 (exon 4, codon 177), resulting in a truncated protein by converting a serine to a stop codon. A patient with multiple juvenile polyps was shown to have a one basepair deletion at nucleotide 1165 (exon 8, codon 345), resulting in a frame shift and a new stop codon at nucleotide 1276–1278 (codons 382–383).

It is contemplated that other mutations in the DPC4 gene may be identified in accordance with the present invention by detecting a nucleotide change in particular nucleic acids (U.S. Pat. No. 4,988,617, incorporated herein by reference). A variety of different assays are contemplated in this regard, including but not limited to, fluorescent in situ hybridization (FISH; U.S. Pat. No. 5,633,365 and U.S. Pat. No. 5,665,549, each incorporated herein by reference), direct DNA sequencing, PFGE analysis, Southern or Northern blotting, single-stranded conformation analysis (SSCA), RNAse protection assay, allele-specific oligonucleotide (ASO e.g., U.S. Pat. No. 5,639,611), dot blot analysis denaturing gradient gel electrophoresis (e.g., U.S. Pat. No. 5,190,856 incorporated herein by reference). RFLP (e.g., U.S. Pat. No. 5,324,631 incorporated herein by reference) and PCR™-SSCP. Methods for detecting and quantitating gene sequences, such as mutated. genes and oncogenes, in for example biological fluids are described in U.S. Pat. No. 5,496,699, incorporated herein by reference.

a. Primers and Probes

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred. Probes are defined differently, although they may act as primers. Probes, while perhaps capable of priming, are designed to binding to the target DNA or RNA and need not be used in an amplification process.

In preferred embodiments, the probes or primers are labeled with radioactive species ($^{32}P$, $^{14}C$, $^{35}S$, $^{3}H$, or other label), with a fluorophore (rhodamine, fluorescein) or a chemillumiscent (luciferase).

b. Template Dependent Amplifcation Methods

A number of template dependent processes are available to amplify the marker sequences present in a given template sample. One of the best known amplification methods is the polymerase chain reaction (referred to as PCR™) which is described in detail in U.S. Pat. No. Nos. 4,683,195, 4,683, 202 and 4,800,159, and in Innis et al., 1990, each of which is incorporated herein by reference in its entirety.

Briefly, in PCR™, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR™ amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641 filed Dec. 21, 1990. Polymerase chain reaction methodologies are well known in the art.

Another method for amplification is the ligase chain reaction ("LCR" U.S. Pat. Nos. 5,494,810, 5,484,699, EPO No. 320 308, each incorporated herein by reference). In LCR, two complementary probe pairs are prepared, and in the presence of the target sequence, each pair will bind to opposite complementary strands of the target such that they abut. In the presence of a ligase, the two probe pairs will link to form a single unit.

By temperature cycling, as in PCR™, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase an RNA-directed RNA polymerase, also may be used as still another amplification method in the present invention. In this method, a replicative sequence of RNA that has a region complementary to that of a target is added to a sample in the presence of an RNA polymerase. The polymerase will copy the replicative sequence that can then be detected. Similar methods also are described in U.S. Pat. No. 4,786,600, incorporated herein by reference, which concerns recombinant RNA molecules capable of serving as a template for the synthesis of complementary single-stranded molecules by RNA-directed RNA polymerase. The product molecules so formed also are capable of serving as a template for the synthesis of additional copies of the original recombinant RNA molecule.

An isothermal amplification method, in which restriction endonucleases and ligases are used to achieve the amplification of target molecules that contain nucleotide 5'-[alpha-thio]-triphosphates in one strand of a restriction site also may be useful in the amplification of nucleic acids in the present invention (Walker et al, 1992; U.S. Pat. No. 5,270,184 incorporated herein by reference). U.S. Pat. No. 5,747,255 (incorporated herein by reference) describes an isothermal amplification using cleavable oligonucleotides for polynucleotide detection. In the method described therein, separated populations of oligonucleotides are provided that contain complementary sequences to one another and that contain at least one scissile linkage which is cleaved whenever a perfectly matched duplex is formed containing the linkage. When a target polynucleotide contacts a first oligonucleotide cleavage occurs and a first fragment is produced which can hybridize with a second oligonucleotide. Upon such hybridization, the second oligonucleotide is cleaved releasing a second fragment that can. in turn, hybridize with a first oligonucleotide in a manner similar to that of the target polynucleotide.

Strand Displacement Amplification (SDA) is another method of carrying out isothermal amplification of nucleic acids which involves multiple rounds of strand displacement and synthesis, i.e., nick translation (e.g., U.S. Pat. Nos. 5,744,311; 5,733,752; 5,733,733; 5,712,124). A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization. the reaction is treated with RNase H, and the products of the probe identified as distinctive products that are released after digestion. The original template is annealed to another cycling probe and the reaction is repeated.

Still another amplification methods described in GB Application No. 2 202 328, and in PCT Application No. PCT/US89/01025, each of which is incorporated herein by reference in its entirety, may be used in accordance with the present invention. In the former application, "modified" primers are used in a PCR™-like, template-and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double stranded DNA, and then transcribed once again with an RNA polymerase such as T7 or SP6. The resulting products. whether truncated or complete, indicate target specific sequences.

Davey et al., EPO No. 329 822 (incorporated herein by reference in its entirety) disclose a nucleic acid amplification process involving cyclically synthesizing single-stranded RNA ("ssRNA"), ssDNA; and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes. this amplification can be done isothermally without addition of enzymes at each cycle. Because of the cyclical nature of this process, the starting sequence can be chosen to be in the form of either DNA or RNA.

Miller et al. PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR™" (Frohman, 1990; Ohara et al., 1989; each herein incorporated by reference in their entirety).

Methods based on ligation of two (or more) oligonucleotides in the presence of nucleic acid having the sequence of the resulting "di-oligonucleotide", thereby amplifying the di-oligonucleotide, also may be used in the amplification step of the present, invention. Wu et al., (1989), incorporated herein by reference in its entirety.

c. Southern/Northern Blotting

Blotting techniques are well known to those of skill in the art. Southern blotting involves the use of DNA as a target, whereas Northern blotting involves the use of RNA as a target. Each provide different types of information, although CDNA blotting is analogous, in many aspects, to blotting or RNA species.

Briefly, a probe is used to target a DNA or RNA species that has been immobilized on a suitable matrix, often a filter of nitrocellulose. The different species should be spatially separated to facilitate analysis. This often is accomplished by gel electrophoresis of nucleic acid species followed by "blotting" on to the filter.

Subsequently, the blotted target is incubated with a probe (usually labeled) under conditions that promote denaturation and rehybridization. Because the probe is designed to base pair with the target, the probe will binding a portion of the target sequence under renaturing conditions. Unbound probe is then removed, and detection is accomplished as described above.

d. Separation Methods

It normally is desirable, at one stage or another, to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder. 1982).

e. Detection Methods

Products may be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin. and the other member of the binding pair carries a detectable moiety.

In one embodiment, detection is by a labeled probe. The techniques involved are well known to those of skill in the art and can be found in many standard books on molecular protocols. See Sambrook et al., 1989. For example, chromophore or radiolabel probes or primers identify the target during or following amplification.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

In addition, the amplification products described above may be subjected to sequence analysis to identify specific kinds of variations using standard sequence analysis techniques. Within certain methods, exhaustive analysis of genes is carried out by sequence analysis using primer sets designed for optimal sequencing (Pignon et al, 1994). The present invention provides methods by which any or all of these types of analyses may be used. Using the sequences disclosed herein, oligonucleotide primers may be designed to permit the amplification of sequences throughout the DPC4 gene that may then be analyzed by direct sequencing.

f. Kit Components

All the essential materials and reagents required for detecting and sequencing DPC4 and variants thereof may be assembled together in a kit. This generally will comprise preselected primers and probes. Also included may be enzymes suitable for amplifying nucleic acids including various polymerases (RT, Taq, Sequenase™ etc.), deoxynucleotides and buffers to provide the necessary reaction mixture for amplification. Such kits also generally will comprise, in suitable means, distinct containers for each individual reagent and enzyme as well as for each primer or probe.

g. Design and Titeoretical Considerations for Relative Quantitative RT-PCR™

Reverse transcription (RT) of RNA to CDNA followed by relative quantitative PCR™ (RT-PCR™) can be used to determine the relative concentrations of specific mRNA species isolated from patients. By determining that the concentration of a specific mRNA species varies, it is shown that the gene encoding the specific mRNA species is differentially expressed.

In PCR™, the number of molecules of the amplified target DNA increase by a factor approaching two with every cycle of the reaction until some reagent becomes limiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR™ amplification is directly proportional to the starting concentration of the target before the reaction began. By determining the concentration of the amplified products of the target DNA in PCR™ reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived can be determined for the respective tissues or cells. This direct proportionality between the concentration of the PCR™ products and the relative mRNA abundances is only true in the linear range of the PCR™ reaction.

The final concentration of the target DNA in the plateau portion of the curve is determined by the availability of reagents in the reaction mix and is independent of the original concentration of target DNA. Therefore, the first condition that must be met before the relative abundances of a mRNA species can be determined by RT-PCR™ for a collection of RNA populations is that the concentrations of the amplified PCR™ products must be sampled when the PCR™ reactions are in the linear portion of their curves.

The second condition that must be met for an RT-PCR™ experiment to successfully determine the relative abundances of a particular mRNA species is that relative concentrations of the amplifiable cDNAs must be normalized to some independent standard. The goal of an RT-PCR™ experiment is to determine the abundance of a particular mRNA species relative to the average abundance of all mRNA species in the sample. In the experiments described below, mRNAs for β-actin, asparagine synthetase and lipocortin II were used as external and internal standards to which the relative abundance of other mRNAs are compared.

Most protocols for competitive PCR™ utilize internal PCR™ standards that are approximately as abundant as the target. These strategies are effective if the products of the PCR™ amplifications are sampled during their linear phases. If the products are sampled when the reactions are approaching the plateau phase, then the less abundant product becomes relatively over represented. Comparisons of relative abundances made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons can be made between RNA samples.

The above discussion describes theoretical considerations for an RT-PCR™ assay for clinically derived materials. The problems inherent in clinical samples are that they are of variable quantity (making normalization problematic), and that they are of variable quality (necessitating the co-amplification of a reliable internal control, preferably of larger size than the target). Both of these problems are overcome if the RT-PCR™ is performed as a relative quantitative RT-PCR™ with an internal standard in which the internal standard is an amplifiable CDNA fragment that is larger than the target cDNA fragment and in which the abundance of the mRNA encoding the internal standard is roughly 5–100 fold higher than the mRNA encoding the target. This assay measures relative abundance, not absolute abundance of the respective mRNA species.

Other studies may be performed using a more conventional relative quantitative RT-PCR™ assay with an external standard protocol. These assays sample the PCR™ products in the linear portion of their amplification curves. The number of PCR™ cycles that are optimal for sampling must be empirically determined for each target cDNA fragment. In addition, the reverse transcriptase products of each RNA population isolated from the various tissue samples must be carefully normalized for equal concentrations of amplifiable cDNAs. This consideration is very important since the assay measures absolute mRNA abundance. Absolute mRNA abundance can be used as a measure of differential gene expression only in normalized samples. While empirical determination of the linear range of the amplification curve and normalization of cDNA preparations are tedious and time consuming processes, the resulting RT-PCR™ assays can be superior to those derived from the relative quantitative RT-PCR™ assay with an internal standard.

One reason for this advantage is that without the internal standard/competitor, all of the reagents can be converted into a single PCR™ product in the linear range of the amplification curve, thus increasing the sensitivity of the assay. Another reason is that with only one PCR™ product, display of the product on an electrophoretic gel or another display method becomes less complex, has less background and is easier to interpret.

h. Chip Technologies

Specifically contemplated by the present inventors are chip-based DNA technologies such as those described by Hacia et al., (1996) and Shoemaker et al., (1996). Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization. See also Pease et al, (1994); Fodor et al., (1991).

II. Immunodiagnosis

Antibodies can be used in characterizing the DPC4 content of healthy and diseased tissues, through techniques such as ELISAs and Western blotting. This may provide a screen for the presence or absence of malignancy or as a predictor of future cancer.

The use of antibodies of the present invention, in an ELISA assay is contemplated. For example, anti-DPC4 antibodies are immobilized onto a selected surface, preferably a surface exhibiting a protein affinity such as the wells of a polystyrene microtiter plate. After washing to remove incompletely adsorbed material, it is desirable to bind or coat the assay plate wells with a non-specific protein that is known to be antigenically neutral with regard to the test antisera such as bovine serum albumin (BSA), casein or solutions of powdered milk. This allows for blocking of non-specific adsorption sites on the immobilizing surface and thus reduces the background caused by non-specific binding of antigen onto the surface.

After binding of antibody to the well, coating with a non-reactive material to reduce background, and washing to remove unbound material, the immobilizing surface is contacted with the sample to be tested in a manner conducive to immune complex (antigen/antibody) formation.

Following formation of specific immunocomplexes between the test sample and the bound antibody, and subsequent washing, the occurrence and even amount of immunocomplex formation may be determined by subjecting same to a second antibody having specificity for DPC4 that differs the first antibody. Appropriate conditions preferably include diluting the sample with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 hr, at temperatures preferably on the order of about 25° to about 27° C. Following incubation, the antisera-contacted surface is washed so as to remove non-immunocomplexed material. A preferred washing procedure includes washing with a solution such as PBS/Tween® or borate buffer.

To provide a detecting means, the second antibody will preferably have an associated enzyme that will generate a color development upon incubating with an appropriate chromogenic substrate. Thus, for example, one will desire to contact and incubate the second antibody-bound surface with a urease or peroxidase-conjugated anti-human IgG for a period of time and under conditions which favor the development of immunocomplex formation (e.g., incubation for 2 hr at room temperature in a PBS-containing solution such as PBS/Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectrum spectrophotometer.

The preceding format may be altered by first binding the sample to the assay plate. Then, primary antibody is incubated with the assay plate, followed by detecting of bound primary antibody using a labeled second antibody with specificity for the primary antibody.

The steps of various other useful immunodetection methods have been described in the scientific literature, such as, eg., Nakamura et al., (1987; incorporated herein by reference). Immunoassays, in their most simple and direct sense, are binding assays. Certain preferred immunoassays are the various types of radioimmunoassays (RIA) and immunobead capture assay. Immunohistochemical detection using tissue-sections also is particularly useful. However, it will be readily appreciated that detection is not limited to such techniques, and Western blotting, dot blotting, FACS analyses, and the like also may be used in connection with the present invention.

The antibody compositions of the present invention will find great use in immunoblot or Western blot analysis. The antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. Immunologically-based detection methods for use in conjunction with Western blotting include enzymatically-, radiolabel-, or fluorescently-tagged secondary antibodies against the toxin moiety are considered to be of particular use in this regard. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

5. Methods for Screening Active Compounds

The present invention also contemplates the use of DPC4 and active fragments, and nucleic acids coding therefor, in the screening of compounds for activity in either stimulating DPC4 activity, overcoming the lack of DPC4 or blocking the effect of a mutant DPC4 molecule. These assays may make use of a variety of different formats and may depend on the kind of "activity" for which the screen is being conducted. Contemplated functional "read-outs" include binding to a compound, inhibition of binding to a substrate ligand, receptor or other binding partner by a compound, phosphatase activity, TGF-$\beta$ interaction of DPC4, inhibition or stimulation of cell-to-cell signaling, growth, metastasis, cell division, cell migration, soft agar colony formation, contact inhibition, invasiveness, angiogenesis, apoptosis, tumor progression or other malignant phenotype.

I. In Vitro Assays

In one embodiment, the invention is to be applied for the screening of compounds that bind to the DPC4 molecule or fragment thereof. The polypeptide or fragment may be either free in solution, fixed to a support, expressed in or on the surface of a cell. Either the polypeptide or the compound may be labeled, thereby permitting determining of binding.

In another embodiment, the assay may measure the inhibition of binding of DPC4 to a natural or artificial substrate or binding partner. Competitive binding assays can be performed in which one of the agents (DPC4, binding partner or compound) is labeled. Usually, the polypeptide will be the labeled species. One may measure the amount of free label versus bound label to determine binding or inhibition of binding.

Another technique for high throughput screening of compounds is described in WO 84/03564. Large numbers of small peptide test compounds are synthesized on a solid substrate, such as plastic pins or some other surface. The peptide test compounds are reacted with DPC4 and washed. Bound polypeptide is detected by various methods.

Purified DPC4 can be coated directly onto plates for use in the aforementioned drug screening techniques. However, non-neutralizing antibodies to the polypeptide can be used to immobilize the polypeptide to a solid phase. Also, fusion proteins containing a reactive region (preferably a terminal region) may be used to link the DPC4 active region to a solid phase.

Various cell lines containing wild-type or natural or engineered mutations in DPC4 can be used to study various functional attributes of DPC4 and how a candidate compound affects these attributes. Methods for engineering mutations are described elsewhere in this document, as are naturally-occurring mutations in DPC4 that lead to, contribute to and/or otherwise cause malignancy. In such assays, the compound would be formulated appropriately, given its biochemical nature, and contacted with a target cell. Depending on the assay, culture may be required. The cell may then be examined by virtue of a number of different physiologic assays. Alternatively, molecular analysis may be performed in which the function of DPC4, or related pathways, may be explored. This may involve assays such as those for protein expression, enzyme function, substrate utilization, phosphorylation states of various molecules including DPC4, cAMP levels, mRNA expression (including differential display of whole cell or polyA RNA) and others.

II. In Vivo Assays

The present invention also encompasses the use of various animal models. Thus, any identity seen between human and other animal DPC4 provides an excellent opportunity to examine the function of DPC4 in a whole animal system where it is normally expressed. By developing or isolating mutant cells lines that fail to express normal DPC4, one can generate models in mice that will be highly predictive of juvenile polyposis and related cancers in humans and other mammals. These models may employ the orthotopic or systemic administration of tumor cells to mimic juvenile polyposis and/or associated cancers. Alternatively, one may induce such a malignant phenotype in animals by providing agents known to be responsible for certain events associated with malignant transformation and/or tumor progression. Finally, transgenic animals (discussed below) that lack a wild-type DPC4 may be utilized as models for juvenile polyposis and cancer development and treatment.

Treatment of animals with test compounds will involve the administration of the compound, in an appropriate form, to the animal. Administration will be by any route the could be utilized for clinical or non-clinical purposes, including but not limited to oral, nasal, buccal, rectal, vaginal or topical. Alternatively, administration may be by intratracheal instillation, bronchial instillation, intradermal, subcutaneous, intramuscular, intraperitoneal or intravenous injection. Specifically contemplated are systemic intravenous injection, regional administration via blood or lymph supply and intratumoral injection.

Determining the effectiveness of a compound in vivo may involve a variety of different criteria. Such criteria include, but are not limited to, survival, reduction of tumor burden or mass, arrest or slowing of tumor progression, elimination of tumors, inhibition or prevention of metastasis, increased activity level, improvement in immune effector function and improved food intake.

III. Rational Drug Design

The goal of rational drug design is to produce structural analogs of biologically active polypeptides or compounds with which they interact (agonists, antagonists, inhibitors, binding partners, etc.). By creating such analogs, it is possible to fashion drugs which are more active or stable than the natural molecules, which have different susceptibility to alteration or which may affect the function of various other molecules. In one approach, one would generate a three-dimensional structure for DPC4 or a fragment thereof. This could be accomplished by x-ray crystallography, computer modeling or by a combination of both approaches. An alternative approach, "alanine scan," involves the random replacement of residues throughout molecule with alanine, and the resulting affect on function determined.

It also is possible to isolate a DPC4 specific antibody, selected by a functional assay, and then solve its crystal structure. In principle, this approach yields a pharmacore upon which subsequent drug design can be based. It is possible to bypass protein crystallograph altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

Thus, one may design drugs which have improved DPC4 activity or which act as stimulators, inhibitors, agonists, antagonists of DPC4 or molecules affected by DPC4 function. By virtue of the availability of cloned DPC4 sequences, sufficient amounts of DPC4 can be produced to perform crystallographic studies. In addition. knowledge of the polypeptide sequences permits computer employed predictions of structure-function relationships.

VI. Transgenic Animals/Knockout Animals

In one embodiment of the invention, transgenic animals are produced which contain a functional transgene encoding a functional DPC4 polypeptide or variants thereof. Transgenic animals expressing DPC4 transgenes, recombinant cell lines derived from such animals and transgenic embryos may be useful in methods for screening for and identifying agents that induce or repress function of DPC4 Transgenic animals of the present invention also can be used as models for studying indications such as cancers.

In one embodiment of the invention, a DPC4 transgene is introduced into a non-human host to produce a transgenic animal expressing a human or murine DPC4 gene. The transgenic animal is produced by the integration of the transgene into the genome in a manner that permits the expression of the transgene. Methods for producing transgenic animals are generally described by Wagner and Hoppe (U.S. Pat. No. 4,873,191; which is incorporated herein by reference), Brinster et al, 1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

It may be desirable to replace the endogenous DPC4 by homologous recombination between the transgene and the endogenous gene; or the endogenous gene may be eliminated by deletion as in the preparation of "knock-out" animals. Typically, a DPC4 gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish. Within a particularly preferred embodiment, transgenic mice are generated which overexpress DPC4 or express a mutant form of the polypeptide. Alternatively, the absence of a DPC4 in "knock-out" mice permits the study of the effects that loss of DPC4 protein has on a cell in vivo. Knock-out mice also provide a model for the development of DPC4-related malignancy for example, juvenile polyposis.

As noted above, transgenic animals and cell lines derived from such animals may find use in certain testing experiments. In this regard, transgenic animals and cell lines capable of expressing wild-type or mutant DPC4 may be exposed to test substances. These test substances can be screened for the ability to enhance wild-type DPC4 expression and or function or impair the expression or function of mutant DPC4.

6. Methods for Treating DPC4 Related Malignancies

The present invention also involves, in another embodiment, the treatment of juvenile polyposis and cancer. The types of malignancy that may be treated, according to the present invention, is limited only by the involvement of DPC4. By involvement, it is not even a requirement that DPC4 be mutated or abnormal—the overexpression of this tumor suppressor may actually overcome other lesions within the cell. Thus, it is contemplated that a wide variety of tumors may be treated using DPC4 therapy, including cancers of the pancreas, small intestine. large intestine, colon, stomach, rectal tumors or other tissue.

In many contexts, it is not necessary that the tumor cell be killed or induced to undergo normal cell death or "apoptosis." Rather, to accomplish a meaningful treatment, all that is required is that the tumor growth be slowed to some degree. It may be that the tumor growth is completely blocked. however. or that some tumor regression is achieved. Clinical terminology such as "remission" and "reduction of tumor" burden also are contemplated given their normal usage.

I. Genetic Based Therapies

One of the therapeutic embodiments contemplated by the present inventors is the intervention, at the molecular level, in the events involved in the tumorigenesis of some cancers. Specifically, the present inventors intend to provide, to a juvenile polyposis cell (or even a subsequent cancer cell), an expression construct capable of providing DPC4 to that cell. Because the sequence homology between the human, and other DPC4s, any of these nucleic acids could be used in human therapy, as could any of the gene sequence variants discussed above which would encode the same, or a biologically equivalent polypeptide. The lengthy discussion of expression vectors and the genetic elements employed therein is incorporated into this section by reference. Particularly preferred expression vectors are viral vectors such as adenovirus, adeno-associated virus, herpesvirus, vaccinia virus and retrovirus. Also preferred is liposomally-encapsulated expression vector.

Those of skill in the art are well aware of how to apply gene delivery to in vivo and ex vivo situations. For viral vectors, one generally will prepare a viral vector stock. Depending on the kind of virus and the titer attainable, one will deliver $1\times10^4$, $1\times10^5$, $1\times10^6$, $1\times10^7$, $1\times10^8$, $1\times10^9$, $1\times10^{10}$, $1\times10^{11}$ or $1\times10^{12}$ infectious particles to the patient. Similar figures may be extrapolated for liposomal or other non-viral formulations by comparing relative uptake efficiencies. Formulation as a. pharmaceutically acceptable composition is discussed below.

Various routes are contemplated for various tumor types. The section below on routes contains an extensive list of possible routes. For practically any tumor, systemic delivery is contemplated. This will prove especially important for attacking microscopic polyposis and microscopic cancer. Where discrete polyposis mass may be identified, a variety of direct, local and regional approaches may be taken. For example, the tumor may be directly injected with the expression vector. A polyp (or tumor) bed may be treated prior to, during or after resection. Following resection, one generally will deliver the vector by a catheter left in place following surgery. One may utilize the tumor vasculature to introduce the vector into the tumor by injecting a supporting vein or artery. A more distal blood supply route also may be utilized.

In a different embodiment, ex vivo gene therapy is contemplated. This approach is particularly suited, although not limited, to treatment of bone marrow associated cancers. In an ex vivo embodiment, cells from the patient are removed and maintained outside the body for at least some period of time. During this period, a therapy is delivered, after which the cells are reintroduced into the patient; hopefully, any malignant cells in the sample have been killed.

Autologous bone marrow transplant (ABMT) is an example of ex vivo gene therapy. Basically, the notion behind ABMT is that the patient will serve as his or her own bone marrow donor. Thus, a normally lethal dose of irradiation or chemotherapeutic may be delivered to the patient to kill malignant cells, and the bone marrow repopulated with the patients own cells that have been maintained (and perhaps expanded) ex vivo. Because, bone marrow often is contaminated with tumor cells, it is desirable to purge the bone marrow of these cells. Use of gene therapy to accomplish this goal is yet another way DPC4 may be utilized according to the present invention.

II. Immunotherapies

Immunotherapeutics, generally, rely on the use of immune effector cells and molecules to target and destroy malignant cells. The immune effector may be, for example an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

According to the present invention, it is unlikely that DPC4 could serve as a target for an immune effector given that (i) it is unlikely to be expressed on the surface of the cell and (ii) that the presence, not absence, of DPC4 is associated with the normal state. However, it is possible that particular mutant forms of DPC4 may be targeted by immunotherapy, either using antibodies, antibody conjugates or immune effector cells.

A more likely scenario is that immunotherapy could be used as part of a combined therapy, in conjunction with DPC4-targeted gene therapy. The general approach for combined therapy is discussed below. Generally, the tumor cell must bear some marker that is amenable to targeting, i.e., is not present on the majority of other cells. Many tumor marker exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG. Sialyl Lewis Antigen, MucA, MucB, PLAP, estrogen receptor, laminin receptor, erb B and p155.

a. Immunoconjugates.

The invention further provides immunotoxins in which an antibody that binds to a cancer marker, such as a mutant DPC4, is linked to a cytotoxic agent. Immunotoxin technology is fairly well-advanced and known to those of skill in the art. Immunotoxins are agents in which the antibody component is linked to another agent, particularly a cytotoxic or otherwise anticellular agent, having the ability to kill or suppress the growth or cell division of cells.

As used herein, the terms "toxin" and "toxic moiety" are employed to refer to any Cytotoxic or otherwise anticellular agent that has such a killing or suppressive property. Toxins are thus pharmacologic agents that can be conjugated to an antibody and delivered in an active form to a cell, wherein they will exert a significant deleterious effect.

The preparation of immunotoxins is, in general, well known in the art (see, e.g., U.S. Pat. No. 4,340,535, incorporated herein by reference). It also is known that while IgG based immunotoxins will typically exhibit better binding capability and slower blood clearance than their Fab' counterparts, Fab' fragment-based immunotoxins will generally exhibit better tissue penetrating capability as compared to IgG based immunotoxins.

Exemplary anticellular agents include chemotherapeutic agents, radioisotopes as well as cytotoxins. Example of chemotherapeutic agents are hormones such as steroids; antimetabolites such as cytosine arabinoside, fluorouracil, methotrexate or aminopterin; anthracycline; mitomycin C; vinca alkaloids; demecolcine; etoposide; mithramycin; or alkylating agents such as chlorambucil or melphalan.

Preferred immunotoxins often include a plant-, fungal- or bacterial-derived toxin, such as an A chain toxin, a ribosome inactivating protein, α-sarcin, aspergillin, restirictocin, a ribonuclease, diphtheria toxin or pseudomonas exotoxin, to mention just a few examples. The use of toxin-antibody constructs is well known in the art of immunotoxins, as is their attachment to antibodies. Of course, combinations of the various toxins could also be coupled to one antibody molecule, thereby accommodating variable or even enhanced cytotoxicity.

One type of toxin for attachment to antibodies is ricin, with deglycosylated ricin A chain being particularly preferred. As used herein, the term "ricin" is intended to refer to ricin prepared from both natural sources and by recombinant means. Various recombinant or genetically engineered forms of the ricin molecule are known to those of skill in the art, all of which may be employed in accordance with the present invention.

Deglycosylated ricin A chain (dgA) is preferred because of its extreme potency, longer half-life, and because it is economically feasible to manufacture it a clinical grade and scale (available commercially from Inlanid Laboratories, Austin, Tex.). Truncated ricin A chain, from which the 30 N-terminal amino acids have been removed by Nagarase (Sigma), also may be employed.

Linking or coupling one or more toxin moieties to an antibody may be achieved by a variety of mechanisms, for example, covalent binding, affinity binding, intercalation, coordinate binding and complexation. Preferred binding methods are those involving covalent binding, such as using chemical cross-linkers, natural peptides or disulfide bonds.

The covalent binding can be achieved either by direct condensation of existing side chains or by the incorporation of external bridging molecules. Many bivalent or polyvalent agents are useful in coupling protein molecules to other proteins, peptides or amine functions. Examples of coupling agents are carbodiimides, diisocyanates, glutaraldehyde, diazobenzenes, and hexamethylene diamines. This list is not intended to be exhaustive of the various coupling agents known in the art but, rather, is exemplary of the more common coupling agents that may be used.

In preferred embodiments, it is contemplated that one may wish to first derivatize the antibody, and then attach the toxin component to the derivatized product. As used herein, the term "derivatize" is used to describe the chemical modification of the antibody substrate with a suitable cross-linking agent. Examples of cross-linking agents for use in this manner include the disulfide-bond containing linkers SPDP (N-succinimidyl-3-(2-pyridyldithio)propionate) and SMPT (4-succinimidyl-oxycarbonyl-$\alpha$-methyl-$\alpha$(2-pyridyldithio)toluene).

Biologically releasable bonds are particularly important to the realization of a clinically active immunotoxin in that the toxin moiety must be capable of being released from the antibody once it has entered the target cell. Numerous types of linking constructs are known, including simply direct disulfide bond formation between sulfhydryl groups contained on amino acids such as cysteine, or otherwise introduced into respective protein structures, and disulfide linkages using available or designed linker moieties.

Numerous types of disulfide-bond containing linkers are known which can successfully be employed to conjugate toxin moieties to antibodies, however, certain linkers are generally preferred, such as, for example, sterically hindered disulfide bond linkers are preferred due to their greater stability in vivo, thus preventing release of the toxin moiety prior to binding at the site of action. A particularly preferred cross-linking reagent is SMPT, although other linkers such as SATA, SPDP and 2-iminothiolane also may be employed.

Once conjugated, it will be important to purify the conjugate so as to remove contaminants such as unconjugated A chain or antibody. It is important to remove unconjugated A chain because of the possibility of increased toxicity. Moreover, it is important to remove unconjugated antibody to avoid the possibility of competition for the antigen between conjugated and unconjugated species. In any event, a number of purification techniques have been found to provide conjugates to a sufficient degree of purity to render them clinically useful.

In general, the most preferred technique will incorporate the use of Blue-Sepharose with a gel filtration or gel permeation step. Blue-Sepharose is a column matrix composed of Cibacron Blue 3GA and agarose, which has been found to be useful in the purification of immunoconjugates. The use of Blue-Sepharose combines the properties of ion exchange with A chain binding to provide good separation of conjugated from unconjugated binding. The Blue-Sepharose allows the elimination of the free (non conjugated) antibody from the conjugate preparation. To eliminate the free (unconjugated) toxin (e.g., dgA) a molecular exclusion chromatography step may be used using either conventional gel filtration procedure or high performance liquid chromatography.

After a sufficiently purified conjugate has been prepared, one will generally desire to prepare it into a pharmaceutical composition that may be administered parenterally. This is done by using for the last purification step a medium with a suitable pharmaceutical composition. Such formulations will typically include pharmaceutical buffers, along with excipients, stabilizing agents and such like. The pharmaceutically acceptable compositions will be sterile, non-immunogenic and non-pyrogenic. Details of their preparation are well known in the art and are further described herein. It will be appreciated that endotoxin contamination should be kept minimally at a safe level, for example, less that 0.5 ng/mg protein.

Suitable pharmaceutical compositions in accordance with the invention will generally comprise from about 10 to about 100 mg of the desired conjugate admixed with an acceptable pharmaceutical diluent or excipient, such as a sterile aqueous solution, to give a final concentration of about 0.25 to about 2.5 mg/ml with respect to the conjugate.

As mentioned above, the antibodies of the invention may be linked to one or more chemotherapeutic agents, such as anti-tumor drugs, cytokines, antimetabolites, alkylating agents, hormones, nucleic acids and the like, which may thus be targeted to a DPC4 expressing cell using the antibody conjugate. The advantages of antibody-conjugated agents over their non-antibody conjugated counterparts is the added selectivity afforded by the antibody.

In analyzing the variety of chemotherapeutic and pharmacologic agents available for conjugating to an antibody, one may wish to particularly consider those that have been previously shown to be successfully conjugated to antibodies and to function pharmacologically. Exemplary antineoplastic agents that have been used include doxorubicin daunomycin, methotrexate, vinblastine. Moreover, the attachment of other agents such as neocarzinostatin, macromycin, trenimon and $\alpha$-amanitin has also been described. The lists of suitable agents presented herein are, of course merely exemplary in that the technology for attaching pharmaceutical agents to antibodies for specific delivery to tissues is well established.

Thus, it is generally believed to be possible to conjugate to antibodies any pharmacologic agent that has a primary or secondary amine group, hydrazide or hydrazine group, carboxyl alcohol, phosphate, or alkylating group available for binding or cross-linking to the amino acids or carbohydrate groups of the antibody. In the case of protein structures, this is most readily achieved by means of a cross linking agent, as described above for the immunotoxins. Attachment also may be achieved by means of an acid labile acyl hydrazone or cis aconityl linkage between the drug and the antibody, or by using a peptide spacer such as L-Leu-L-Ala-L-Leu-L-Ala, between the $\gamma$-carboxyl group of the drug and an amino acid of the antibody.

III. Protein Therapy

Another therapy approach is the provision, to a subject, of DPC4 polypeptide, active fragments, synthetic peptides, mimetics or other analogs thereof. The protein may be produced by recombinant expression means or, if small enough, generated by an automated peptide synthesizer. Formulations would be selected based on the route of administration and purpose including, but not limited to, liposomal formulations and classic pharmaceutical preparations.

VI. Combined Therapy with Immunotherapy, Traditional Chemo- or Radiotherapy

Tumor cell resistance to DNA damaging agents represents a major problem in clinical oncology. One goal of current cancer research is to find ways to improve the efficacy of chemo- and radiotherapy. One way is by combining such traditional therapies with gene therapy. For example, the herpes simplex-thymidine kinase (HS-tk) gene, when delivered to brain tumors by a retroviral vector system, successfully induced susceptibility to the antiviral agent ganciclovir (Culver et al., 1992). In the context of the present invention, it is contemplated that DPC4 replacement therapy could be used similarly in conjunction with chemo-or radiotherapeutic intervention. It also may prove effective to combine DPC4 gene therapy with immunotherapy, as described above.

To kill cells, inhibit cell growth, inhibit metastasis, inhibit angiogenesis or otherwise reverse or reduce the malignant phenotype of tumor cells, using the methods and compositions of the present invention, one would generally contact a "target" cell with a DPC4 expression construct and at least one other agent. These compositions would be provided in a combined amount effective to kill or inhibit proliferation of the cell. This process may involve contacting the cells with the expression construct and the agent(s) or factor(s) at the same time. This may be achieved by contacting the cell with a single composition or pharmacological formulation that includes both agents, or by contacting the cell with two distinct compositions or formulations, at the same time, wherein one composition includes the expression construct and the other includes the agent.

Alternatively, the gene therapy treatment may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one would contact the cell with both modalities within about 12–24 hours of each other and, more preferably, within about 6–12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either DPC4 or the other agent will be desired. Various combinations may be employed, where DPC4 is "A" and the other agent is "B", as exemplified below:

A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B

Other combinations are contemplated. Again, to achieve cell killing, both agents are delivered to a cell in a combined amount effective to kill the cell.

Agents or factors suitable for use in a combined therapy are any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety of chemical compounds, also described as "chemotherapeutic agents," function to induce DNA damage, all of which are intended to be of use in the combined treatment methods disclosed herein. Chemotherapeutic agents contemplated to be of use, include, e.g., adriamnycin, 5-fluorouracil (5FU), etoposide (VP-16), camptothecin, actinomycin-D, mitomycin C, cisplatin (CDDP) and even hydrogen peroxide. The invention also encompasses the use of a combination of one or more DNA damaging agents, whether radiation-based or actual compounds, such as the use of X-rays with cisplatin or the use of cisplatin with etoposide. In certain embodiments, the use of cisplatin in combination with a DPC4 expression construct is particularly preferred as this compound.

In treating juvenile polyposis or a related cancer according to the invention, one would contact the tumor cells with an agent in addition to the expression construct. This may be achieved by irradiating the localized tumor site with radiation such as X-rays, UV-light, D-rays or even microwaves. Alternatively, the tumor cells may be contacted with the agent by administering to the subject a therapeutically effective amount of a pharmaceutical composition comprising a compound such as, adriamycin, 5-fluorouracil, etoposide, camptothecin, actinomycin-D, mitomycin C, or more preferably, cisplatin. The agent may be prepared and used as a combined therapeutic composition, or kit, by combining it with a DPC4 expression construct, as described above.

Agents that directly cross-link nucleic acids, specifically DNA, are envisaged to facilitate DNA damage leading to a synergistic, antineoplastic combination with DPC4. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25–75 mg/m$^2$ at 21 day intervals for adriamycin, to 35–50 mg/m2 for etoposide intravenously or double the intravenous dose orally.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, X-rays, and/or the directed delivery of radioisotopes to tumor cells. Other forms of DNA damaging factors also are contemplated such as microwaves and UV-irradiation. It is most likely that all of these factors effect a broad range of damage DNA, on the precursors of DNA-the replication and repair of DNA, and the assembly and maintenance of chromosomes. Dosage ranges for X-rays range from daily doses of 50 to 200 gGy for prolonged periods of time (3 to 4 weeks), to single doses of 2000 to 6000 gGy. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624–652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The inventors propose that the regional delivery of DPC4 expression constructs to patients with DPC4-linked cancers will be a very efficient method for delivering a therapeutically effective gene to counteract the clinical disease. Similarly, the chemo- or radiotherapy may be directed to a particular, affected region of the subjects body. Alternatively, systemic delivery of expression construct and/or the agent may be appropriate in certain circumstances, for example, where extensive metastasis has occurred.

In addition to combining DPC4-targeted therapies with chemo-and radiotherapies, it also is contemplated that combination with other gene therapies will be advantageous. For example, targeting of DPC4 and p53 or p16 mutations at the same time may produce an improved anti-cancer treatment. Any other tumor-related gene conceivably can be targeted in this manner, for example, p21, Rb, APC, DCC, NF-1, NF-2, BCRRA2, p16, FHIT, WT-1, MEN-1, RET, BRCA, VHL, FCC, MCC, ras, myc, neu, raf erb, src, fms, jun, irk, ret, gsp, hst, bcl and abl.

It also should be pointed out that any of the foregoing therapies may prove useful by themselves in treating a mutant DPC4. In this regard, reference to chemotherapeutics and non-DPC4 gene therapy in combination should also be read as a contemplation that these approaches may be employed separately.

6. Engineering Expression Constructs

In certain embodiments, the present invention involves the manipulation of genetic material to produce expression constructs that encode a therapeutic gene for the treatment of juvenile polyposis and/or related cancer (DPC4). Such methods involve the generation of expression constructs containing, for example, a heterologous DNA encoding a gene of interest and a means for its expression, replicating the vector in an appropriate helper cell, obtaining viral particles produced therefrom, and infecting cells with the recombinant virus particles.

The gene will be a normal DPC4 gene discussed herein above, or the gene may be a second therapeutic gene or nucleic acid useful in the treatment of, for example cancer cells. In the context of gene therapy, the gene will be a heterologous DNA, meant to include DNA derived from a source other than the viral genome which provides the backbone of the vector. Finally, the virus may act as a live viral vaccine and express an antigen of interest for the production of antibodies there against. The gene may be derived from a prokaryotic or eukaryotic source such as a bacterium, a virus, a yeast, a parasite, a plant, or even an animal. The heterologous DNA also may be derived from more than one source, i.e. a multigene construct or a fusion protein. The heterologous DNA also may include a regulatory sequence which may be derived from one source and the gene from a different source.

I. Additional Therapeutic Genes

The present invention contemplates the use of a variety of different genes in combination with DPC4 gene constructs. For example, genes encoding enzymes, hormones, cytokines, oncogenes, receptors, tumor suppressors, transcription factors, drug selectable markers, toxins and various antigens are contemplated as suitable genes for use according to the present invention. In addition, antisense constructs derived from oncogenes are other "genes" of interest according to the present invention.

As described herein above DPC4 is a known tumor suppressor first found to be deleted in pancreatic cancer 4 (Hahn et al., 1996 Genbank accession No. U44378, specifically incorporated herein by reference). In certain embodiments, of the present invention, it will be possible to introduce wild-type DPC4 to juvenile polyposis cells. U.S. Pat. No. 5,712,097 describes the gene sequence for DPC4 and methods of providing DPC4 to a cell.

a. Other Tumor Suppressors

The genetic constructs of the present invention may further comprise other tumor suppressor in combination with DPC4. p53 is one such ubiquitously recognized as a tumor suppressor gene (Hollstein et clo, 1991; U.S. Pat. No. 5,747,469, specifically incorporated herein by reference in its entirety). Other tumor related genes that could be used herein include $p16^{INK4}$ (Caldas et al., 1994. Cheng et al., 1994; Hussussian et al., 1994; Kamb et al., 1994; Kamb et al., 1994; Mori et al., 1994; Okamoto et al., 1994; Nobori et al., 1995; Orlow et al., 1994; Arap et al., 1995); Cell adhesion molecules, or CAM's (Edelman and Crossin, 1991; Frixen et al, 1991; Bussemakers et al, 1992; Matsura et al., 1992; Umbas et al., 1992); RB. APC, DCC, NF-1, NF-2, WT-1, MEN-I, MEN-II, zacl, p73, VHL, MAMC1, FCC and MCC. Additionally, inducers of apoptosis also are contemplated for use in combination with DPC4, these include members of the Bcl-2 family (Bax, Bax, Bak, Bcl-$X_5$, Bik, Bid, Bad, Harakiri) as well as, Ad E1B and ICE-CED3 proteases, similarly could find use according to the present invention.

b. Enzymes

Various enzyme genes are of interest according to the present invention. Such enzymes include cytosine deaminase, hypoxanthine-guanine phosphoribosyltransferase, galactose-1-phosphate uridyltransferase, phenylalanine hydroxylase, glucocerbrosidase, sphingomyelinase, α-L-iduronidase, glucose-6-phosphate dehydrogenase, HSV thymidine kinase and human thymidine kinase.

C. Cytokines

Other classes of genes that are contemplated to be inserted into the therapeutic expression constructs of the present invention include interleukins and cytokines. Interleukin 1 (IL-1), IL-2, IL-3, IL-4, IL-5, IL-6, IL-7, IL-8, IL-9, IL-10, IL-11 IL-12, GM-CSF and G-CSF.

d. Antibodies

In yet another embodiment, the heterologous gene may include a single-chain antibody. Methods for the production of single-chain antibodies are well known to those of skill in the art. The skilled artisan is referred to U.S. Pat. No. 5,359,046, (incorporated herein by reference) for such methods. A single chain antibody is created by fusing together the variable domains of the heavy and light chains using a short peptide linker, thereby reconstituting an antigen binding site on a single molecule.

Single-chain antibody variable fragments (Fvs) in which the C-terminus of one variable domain is tethered to the N-terminus of the other via a 15 to 25 amino acid peptide or linker, have been developed without significantly disrupting antigen binding or specificity of the binding (Bedzyk et al., 1990; Chaudhary et al., 1990). These Fvs lack the constant regions (Fc) present in the heavy and light chains of the native antibody.

Antibodies to a wide variety of molecules can be used in combination with the present invention, including antibodies against oncogenes, toxins, hormones, enzymes, viral or bacterial antigens, transcription factors, receptors and the like.

II. Antisense constructs

Oncogenes such as ras, myc, neu, raf erb, src, fms, jun, trk, ret, gsp, hst, and abl as well as the antiapoptotic member of the Bcl-2 family also are suitable targets. However, for therapeutic benefit, these oncogenes would be expressed as an antisense nucleic acid, so as to inhibit the expression of the oncogene. The term "antisense nucleic acid" is intended to refer to the oligonucleotides complementary to the base sequences of oncogene-encoding DNA and RNA. Antisense oligonucleotides, when introduced into a target cell, specifically bind to their target nucleic acid and interfere with transcription, RNA processing, transport and/or translation. Targeting double-stranded (ds) DNA with oligonucleotide leads to triple-helix formation; targeting RNA will lead to double-helix formation.

Antisense constructs may be designed to bind to the promoter and other control regions, exons, introns or even exon-intron boundaries of a gene. Antisense RNA constructs, or DNA encoding such antisense RNAs, may be employed to inhibit gene transcription or translation or both within a host cell, either in vitro or in vivo, such as within a host animal, including a human subject. Nucleic acid sequences comprising "complementary nucleotides" are those which are capable of base-pairing according to the standard Watson-Crick complementary rules. That is, that the larger purines will base pair with the smaller pyrimidines to form only combinations of guanine paired with cytosine (G:C) and adenine paired with either thymine (A:T), in the case of DNA, or adenine paired with uracil (A:U) in the case of RNA.

As used herein, the terms "complementary" or "antisense sequences" mean nucleic acid sequences that are substantially complementary over their entire length and have very few base mismatches. For example, nucleic acid sequences of fifteen bases in length may be termed complementary when they have a complementary nucleotide at thirteen or fourteen positions with only single or double mismatches. Naturally, nucleic acid sequences which are "completely complementary" will be nucleic acid sequences which are entirely complementary throughout their entire length and have no base mismatches.

While all or part of the gene sequence may be employed in the context of antisense construction, statistically, any sequence 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that oligonucleotides of 8, 9, 10, 11, 12, 13, 14, 15, 16, 17, 18, 19, 20 or more base pairs will be used. One can readily determine whether a given antisense nucleic acid is effective at targeting of the corresponding host cell gene simply by testing the constructs in vitro to determine whether the endogenous gene's function is affected or whether the expression of related genes having complementary sequences is affected.

In certain embodiments, one may wish to employ antisense constructs which include other elements. for example, those which include C-5 propyne pyrimidines. Oligonucleotides which contain C-5 propyne analogues of utidine and cytidine have been shown to bind RNA with high affinity and to be potent antisense inhibitors of gene expression (Wagner et al., 1993).

III. Ribozyme Constructs

As an alternative to targeted antisense delivery, targeted ribozymes may be used. The term "ribozyme" refers to an RNA-based enzyme capable of targeting and cleaving particular base sequences in oncogene DNA and RNA.

Ribozymes either can be targeted directly to cells, in the form of RNA oligo-nucleotides incorporating ribozyme sequences. or introduced into the cell as an expression construct encoding the desired ribozymal RNA. Ribozymes may be used and applied in much the same way as described for antisense nucleic acids.

IV. Selectable Markers

In certain embodiments of the invention, the therapeutic expression constructs of the present invention contain nucleic acid constructs whose expression may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants. For example, genes that confer resistance to neomycin, puromycin, hygromycin, DHFR, GPT, zeocin and histidinol are useful selectable markers. Alternatively, enzymes such as herpes simplex virus thymidine kinase (tk) may be employed. Immunologic markers also can be employed. The selectable marker employed is not believed to be important, so long as it is capable of being expressed simultaneously with the nucleic acid encoding a gene product. Further examples of selectable markers are well known to one of skill in the art and include reporters such as EGFP, β-gal or chloramphenicol acetyltransferase (CAT).

V. Multigene Constructs and IRES

In certain embodiments of the invention, the use of internal ribosome binding sites (IRES) elements are used to create multigene polycistronic messages. IRES elements are able to bypass the ribosome scanning model of 5'-methylated, Cap-dependent translation and begin translation at internal sites (Pelletier and Sonenberg, 1988). IRES elements from two members of the picanovirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

VI. Control Regions a. Promoters

Throughout this application, the term "expression construct" is meant to include any type of genetic construct containing a nucleic acid coding for gene products in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding genes of interest.

The nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–11 0 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription.

The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, β-actin, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized.

Selection of a promoter that is regulated in response to specific physiologic or synthetic signals can permit inducible expression of the gene product. For example in the case where expression of a transgene, or transgenes when a multicistronic vector is utilized. is toxic to the cells in which the vector is produced in, it may be desirable to prohibit or reduce expression of one or more of the transgenes. Examples of transgenes that may be toxic to the producer cell line are pro-apoptotic and cytokine genes. Several inducible promoter systems are available for production of viral vectors where the transgene product may be toxic.

The ecdysone system (Invitrogen, Carlsbad, Calif.) is one such system. This system is designed to allow regulated expression of a gene of interest in mammalian cells. It consists of a tightly regulated expression mechanism that allows virtually no basal level expression of the transgene, but over 200-fold inducibility. The system is based on the heterodimeric ecdysone receptor of Drosophila, and when ecdysone or an analog such as muristerone A binds to the receptor, the receptor activates a promoter to turn on expression of the downstream transgene high levels of mRNA transcripts are attained. In this system, both monomers of the heterodimeric receptor are constitutively expressed from one vector, whereas the ecdysone-responsive promoter which drives expression of the gene of interest is on another plasmid. Engineering of this type of system into the gene transfer vector of interest would therefore be useful. Cotransfection of plasmids containing the gene of interest and the receptor monomers in the producer cell line would then allow for the production of the gene transfer vector without expression of a potentially toxic transgene. At the appropriate time, expression of the transgene could be activated with ecdysone or muristeron A.

Another inducible system that would be useful is the Tet-Off™ or Tet-On™ system (Clontech, Palo Alto, Calif.) originally developed by Gossen and Bujard (Gossen and Bujard, 1992; Gossen et al, 1995). This system also allows high levels of gene expression to be regulated in response to tetracycline or tetracycline derivatives such as doxycycline. In the Tet-On™ system, gene expression is turned on in the presence of doxycycline, whereas in the Tet-Off™ system, gene expression is turned on in the absence of doxycycline. These systems are based on two regulatory elements derived from the tetracycline resistance operon of E. coli. The tetracycline operator sequence to which the tetracycline repressor binds, and the tetracycline repressor protein. The gene of interest is cloned into a plasmid behind a promoter that has tetracycline-responsive elements present in it. A second plasmid contains a regulatory element called the tetracycline-controlled transactivator, which is composed, in the Tet-Off™ system, of the VP16 domain from the herpes simplex virus and the wild-type tertracycline repressor. Thus in the absence of doxycycline, transcription is constitutively on. In the Tet-On™ system, the tetracycline repressor is not wild type and in the presence of doxycycline activates transcription. For gene therapy vector production, the Tet-Off™ system would be preferable so that the producer cells could be grown in the presence of tetracycline or doxycycline and prevent expression of a potentially toxic transgene, but when the vector is introduced to the patient, the gene expression would be constitutively on.

In some circumstances, it may be desirable to regulate expression of a transgene in a gene therapy vector. For example. different viral promoters with varying strengths of activity may be utilized depending on the level of expression desired. In mammalian cells, the CMV immediate early promoter if often used to provide strong transcriptional activation. Modified versions of the CMV promoter that are less potent have also been used when reduced levels of expression of the transgene are desired. When expression of a transgene in hematopoetic cells is desired. retroviral promoters such as the LTRs from MLV or MMTV are often used. Other viral promoters that may be used depending on the desired effect include SV40, RSV LTR, HIV-1 and HIV-2 LTR, adenovirus promoters such as from the E1A, E2A. or MLP region, AAV LTR, cauliflower mosaic virus, HSV-TK, and avian sarcoma virus.

Similarly tissue specific promoters may be used to effect transcription in specific tissues or cells so as to reduce potential toxicity or undesirable effects to non-targeted tissues. For example, promoters such as the PSA, probasin, prostatic acid phosphatase or prostate-specific glandular kallikrein (hK2) may be used to target gene expression in the prostate. Similarly, the following promoters may be used to target gene expression in other tissues (Table 1).

TABLE 1

Tissue specific promoters

| Tissue | Promoter |
|---|---|
| Pancreas | insulin |
| | elastin |
| | amylase |
| | pdr-1 pdx-1 |
| | glucokinase |
| Liver | albumin PEPCK |
| | HBV enhancer |
| | alpha fetoprotein |
| | apolipoprotein C |
| | alpha-1 antitrypsin |
| | vitellogenin, NF-AB |
| | Transthyretin |
| Skeletal muscle | myosin H chain |
| | muscle creatine kinase |
| | dystrophin |
| | calpain p94 |
| | skeletal alpha-actin |
| | fast troponin 1 |
| Skin | keratin K6 |
| | keratin K1 |
| Lung | CFTR |
| | human cytokeratin 18 (K18) |
| | pulmonary surfactant proteins A, B and C |
| | CC-10 |
| | P1 |
| Smooth muscle | sm22 alpha |
| | SM-alpha-actin |
| Endothelium | endothelin-1 |
| | E-selectin |
| | von Willebrand factor |
| | TIE (Korhonen et al., 1995) |
| | KDR/flk-1 |
| Melanocytes | tyrosinase |
| Adipose tissue | lipoprotein lipase (Zechner et al., 1988) |
| | adipsin (Spiegelman et al., 1989) |
| | acetyl-CoA carboxylase (Pape and Kim, 1989) |
| | glycerophosphate dehydrogenase (Dani et al., 1989) |
| | adipocyte P2 (Hunt el al., 1986) |
| Blood | β-globin |

In certain indications, it may be desirable to activate transcription at specific times after administration of the gene therapy vector. This may be done with such promoters as those that are hormone or cytokine regulatable. For example in gene therapy applications where the indication is a gonadal tissue where specific steroids are produced or routed to, use of androgen or estrogen regulated promoters may be advantageous. Such promoters that are hormone regulatable include MMTV, MT-1, ecdysone and RuBisco. Other hormone regulated promoters such as those responsive to thyroid, pituitary and adrenal hormones are expected to be useful in the present invention. Cytokine and inflammatory protein responsive promoters that could be used include K and T Kininogen (Kageyama et al. 1987). c-fos, TNF-alpha, C-reactive protein (Arcone et al, 1988), haptoglobin (Oliviero et al, 1987), serum amyloid A2, C/EBP alpha, IL-1. IL-6 (Poli and Cortese, 1989), Complement C3 (Wilson et al., 1990), IL-8, alpha-1 acid glycoprotein (Prowse and Baumann, 1988), alpha-1 antitypsin, lipoprotein lipase (Zechner et al., 1988), angiotensinogen (Ron et al., 1991), fibrinogen, c-jun (inducible by phorbol esters, TNF-alpha, UV radiation, retinoic acid, and hydrogen peroxide), collagenase (induced by phorbol esters and retinoic acid), metallothionein (heavy metal and glucocorticoid inducible), Stromelysin (inducible by phorbol ester, interleukin-1 and EGF), alpha-2 macroglobulin and alpha-1 antichymotrypsin.

It is envisioned that cell cycle regulatable promoters may be useful in the present invention. For example, in a bi-cistronic gene therapy vector, use of a strong CMV promoter to drive expression of a first gene such as p16 that arrests cells in the GI phase could be followed by expression of a second gene such as $p^{53}$ under the control of a promoter that is active in the G1 phase of the cell cycle, thus providing a "second hit" that would push the cell into apoptosis. Other promoters such as those of various cyclins, PCNA, galectin-3, E2F1, p53 and BRCA1 could be used.

Tumor specific promoters such as osteocalcin, hypoxia-responsive element (HRE), MAGE-4, CEA, alpha-fetoprotein, GRP78/BiP and tyrosinase also may be used to regulate gene expression in tumor cells. Other promoters that could be used according to the present invention include Lac-regulatable, chemotherapy inducible (e.g., MDR), and heat (hyperthermia) inducible promoters, Radiation-inducible (e.g., EGR (Joki et al., 1995)), Alpha-inhibin, RNA pol III tRNA met and other amino acid promoters, U1 snRNA (Bartlett et al., 1996), MC-1, PGK, -actin and alpha-globin. Many other promoters that may be useful are listed in Walther and Stein (1996).

It is envisioned that any of the above promoters alone or in combination with another may be useful according to the present invention depending on the action desired. In addition this list of promoters should not be construed to be exhaustive or limiting, those of skill in the art will know of other promoters that may be used in conjunction with the promoters and methods disclosed herein.

b. Enhancers

Enhancers are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of promoters additional to the tissue specific promoters listed above, cellular promoters/enhancers and inducible promoters/enhancers that could be used in combination with the nucleic acid encoding a gene of interest in an expression construct (Table 2 and Table 3). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

In preferred embodiments of the invention, the expression construct comprises a virus or engineered construct derived from a viral genome. The ability of certain viruses to enter cells via receptor-mediated endocytosis and to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 KB of foreign genetic material but can be readily introduced in a variety of cell lines and laboratory animals (Nicolas and Rubenstein, 1988; Temin, 1986).

C. Polyadenylation Signals

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human or bovine growth hormone and SV40 polyadenylation signals. Also contemplated as an element of the expression cassette is a terminator. These elements can serve to enhance message levels and to minimize read through from the cassette into other sequences.

TABLE 2

| ENHANCER |
| --- |
| Immunoglobulin Heavy Chain |
| Immunoglobulin Light Chain |
| T-Cell Receptor |
| HLA DQ α and DQ β |
| β-Interferon |
| Interleukin-2 |
| Interleukin-2 Receptor |
| MHC Class II 5 |
| MHC Class II HLA-DRα |
| β-Actin |
| Muscle Creatine Kinase |
| Prealbumin (Transthyretin) |
| Elastase I |
| Metallothionein |
| Collagenase |
| Albumin Gene |
| α-Fetoprotein |
| τ-Globin |
| β-Globin |
| e-fos |
| c-HA-ras |
| Insulin |
| Neural Cell Adhesion Molecule (NCAM) |
| α1-Antitrypsin |
| H2B (TH2B) Histone |
| Mouse or Type I Collagen |
| Glucose-Regulated Proteins (GRP94 and GRP78) |
| Rat Growth Hormone |
| Human Serum Amyloid A (SAA) |
| Troponin I (TN I) |
| Platelet-Derived Growth Factor |
| Duchenne Muscular Dystrophy |
| SV40 |
| Polyoma |
| Retroviruses |
| Papilloma Virus |
| Hepatitis B Virus |
| Human Immunodeficiency Virus |
| Cytomegalovirus |
| Gibbon Ape Leukemia Virus |

TABLE 3

| Element | Inducer |
| --- | --- |
| MT II | Phorbol Ester (TPA) |
| | Heavy metals |
| MMTV (mouse mammary tumor virus) | Glucocorticoids |
| β-Interferon | poly(rI)X |
| | poly(rc) |
| Adenovirus 5 E2 | Ela |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | Ela, SV40 Large T Antigen |
| Proliferin | Phorbol Ester-TPA |
| Tumor Necrosis Factor | FMA |
| Thyroid Stimulating Hormone α Gene | Thyrbid Hormone |
| Insulin E Box | Glucose |

7. Methods of Gene Transfer

In order to mediate the effect transgene expression in a cell, it will be necessary to transfer the therapeutic expression constructs of the present invention into a cell. Such transfer may employ viral or non-viral methods of gene transfer. This section provides a discussion of methods and compositions of gene transfer.

I. Viral Vector-Mediated Transfer

The DPC4 gene is incorporated into an adenoviral infectious particle to mediate gene transfer to a cell. Additional expression constructs encoding other therapeutic agents as described herein also may be transferred via viral transduction using infectious viral particles, for example, by transformation with an adenovirus vector of the present invention as described herein below. Alternatively, retroviral or bovine papilloma virus may be employed, both of which permit permanent transformation of a host cell with a gene(s) of interest. Thus, in one example, viral infection of cells is used in order to deliver therapeutically significant genes to a cell. Typically, the virus simply will be exposed to the appropriate host cell under physiologic conditions, permitting uptake of the virus. Though adenovirus is exemplified, the present methods may be advantageously employed with other viral vectors, as discussed below.

a. Adenovirus.

Adenovirus is particularly suitable for use as a gene transfer vector because of its mid-sized DNA genome, ease of manipulation, high titer, wide target-cell range, and high infectivity. The roughly 36 kB viral genome is bounded by 100–200 base pair (bp) inverted terminal repeats (ITR), in which are contained cis-acting elements necessary for viral DNA replication and packaging. The early (E) and late (L) regions of the genome that contain different transcription units are divided by the onset of viral DNA replication.

The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan, 1990). The products of the late genes (L1, L2, L3, L4 and L5), including the majority of the viral capsid proteins, are expressed only after significant processing of a single primary transcript issued by the major late promoter (MLP). The MLP (located at 16.8 map units) is particularly efficient during the late phase of infection, and all the mRNAs issued from this promoter possess a 5' tripartite leader (TL) sequence which makes them preferred mRNAs for translation.

In order for adenovirus to be optimized for gene therapy, it is necessary to maximize the carrying capacity so that large segments of DNA can be included. It also is very desirable to reduce the toxicity and immunologic reaction associated with certain adenoviral products. The two goals are, to an extent, coterminous in that elimination of adenoviral genes serves both ends. By practice of the present invention, it is possible achieve both these goals while retaining the ability to manipulate the therapeutic constructs with relative ease.

The large displacement of DNA is possible because the cis elements required for viral DNA replication all are localized in the inverted terminal repeats (ITR) (100–200 bp) at either end of the linear viral genome. Plasmids containing ITR's can replicate in the presence of a non-defective adenovirus (Hay et al., 1984). Therefore, inclusion of these elements in an adenoviral vector should permit replication.

In addition, the packaging signal for viral encapsidation is localized between 194–385 bp (0.5–1.1 map units) at the left end of the viral genome (Hearing et al., 1987). This signal mimics the protein recognition site in bacteriophage λ DNA where a specific sequence close to the left end, but outside the cohesive end sequence, mediates the binding to proteins that are required for insertion of the DNA into the head structure. E1 substitution vectors of Ad have demonstrated that a 450 bp (0–1.25 map units) fragment at the left end of the viral genome could direct packaging in 293 cells (Levrero et al., 1991).

Previously, it has been shown that certain regions of the adenoviral genome can be incorporated into the genome of mammalian cells and the genes encoded thereby expressed. These cell lines are capable of supporting the replication of an adenoviral vector that is deficient in the adenoviral function encoded by the cell line. There also have been reports of complementation of replication deficient adenoviral vectors by "helping" vectors, e.g., wild-type virus or conditionally defective mutants.

Replication-deficient adenoviral vectors can be complemented, in trans, by helper virus. This observation alone does not permit isolation of the replication-deficient vectors, however, since the presence of helper virus, needed to provide replicative functions, would contaminate any preparation. Thus. an additional element was needed that would add specificity to the replication and/or packaging of the replication-deficient vector. That element, as provided for in the present invention, derives from the packaging function of adenovirus.

It has been shown that a packaging signal for adenovirus exists in the left end of the conventional adenovirus map (Tibbetts, 1977). Later studies showed that a mutant with a deletion in the E1A (194–358 bp) region of the genome grew poorly even in a cell line that complemented the early (E1A) function (Hearing and Shenk, 1983). When a compensating adenoviral DNA (0–353 bp) was recombined into the right end of the mutant, the virus was packaged normally. Further mutational analysis identified a short, repeated, position-dependent element in the left end of the Ad5 genome. One copy of the repeat was found to be sufficient for efficient packaging if present at either end of the genome, but not when moved towards the interior of the Ad5 DNA molecule (Hearing et al, 1987).

By using mutated versions of the packaging signal, it is possible to create helper viruses that are packaged with varying efficiencies. Typically, the mutations are point mutations or deletions. When helper viruses with low efficiency packaging are grown in helper cells. the virus is packaged, albeit at reduced rates compared to wild-type virus, thereby permitting propagation of the helper. When these helper viruses are grown in cells along with virus that contains wild-type packaging signals, however, the wild-type packaging signals are recognized preferentially over the mutated versions. Given a limiting amount of packaging factor, the virus containing the wild-type signals are packaged selectively when compared to the helpers. If the preference is great enough, stocks approaching homogeneity should be achieved.

b. Retrovirus.

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes—gag, pol and env—that code for capsid proteins, polymerase enzyme, and envelope components, respectively. A sequence found upstream from the gag gene, termed Ψ, functions as a signal for packaging of the genome into virions. Two long terminal repeat (LTR) sequences are present at the 5' and 3' ends of the viral genome. These contain strong promoter and enhancer sequences and also are required for integration in the host cell genome (Coffin, 1990).

In order to construct a retroviral vector, a nucleic acid encoding a promoter is inserted into the viral genome in the place of certain viral sequences to produce a virus that is replication-defective. In order to produce virions, a packaging cell line containing the gag, pol and env genes but without the LTR and Ψ components is constructed (Mann et al., 1983). When a recombinant plasmid containing a human CDNA, together with the retroviral LTR and Ψ sequences is introduced into this cell line (by calcium phosphate precipitation for example), the Ψ sequence allows the RNA transcript of the recombinant plasmid to be packaged into viral particles, which are then secreted into the culture media (Nicolas and Rubenstein, 1988; Temin, 1986; Mann et al, 1983). The media containing the recombinant retroviruses is collected, optionally concentrated, and used for gene transfer. Retroviral vectors are able to infect a broad variety of cell types. However, integration and stable expression of many types of retroviruses require the division of host cells (Paskind et al., 1975).

An approach designed to allow specific targeting of retrovirus vectors recently was developed based on the chemical modification of a retrovirus by the chemical addition of galactose residues to the viral envelope. This modification could permit the specific infection of cells such as hepatocytes via asialoglycoprotein receptors. should this be desired.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, the infection of a variety of human cells that bore those surface antigens was demonstrated with an ecotropic virus in vitro (Roux et al., 1989).

c. Adeno-associated Virus.

AAV utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription.

The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42–46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low level expression of AAV rep proteins is believed to hold AAV structural expression in check, and helper virus infection is thought to remove this block.

The terminal repeats of the AAV vector can be obtained by restriction endonuclease digestion of AAV or a plasmid such as p201, which contains a modified AAV genome (Samulski et al., 1987), or by other methods known to the skilled artisan, including but not limited to chemical or enzymatic synthesis of the terminal repeats based upon the published sequence of AAV. The ordinarily skilled artisan can determnine, by well-known methods such as deletion analysis, the minimum sequence or part of the AAV ITRs which is required to allow function, i.e., stable and site-specific integration. The ordinarily skilled artisan also can determine which minor modifications of the sequence can be tolerated while maintaining the ability of the terminal repeats to direct stable, site-specific integration.

AAV-based vectors have proven to be safe and effective vehicles for gene delivery in vitro, and these vectors are being developed and tested in pre-clinical and clinical stages for a wide range of applications in potential gene therapy, both ex vivo and in vivo (Carter and Flotte, 1996; Chatterjee et al., 1995; Ferrari et al., 1996; Fisher et al., 1996; Flotte et al., 1993; Goodman et al., 1994; Kaplitt et al, 1994; 1996; Kessler et al., 1996; Koeberl et al., 1997; Mizukami et al., 1996).

AAV-mediated efficient gene transfer and expression in the lung has led to clinical trials for the treatment of cystic fibrosis (Carter and Flotte, 1996; Flotte et al., 1993). Similarly, the prospects for treatment of muscular dystrophy by AAV-mediated gene delivery of the dystrophin gene to skeletal muscle, of Parkinson's disease by tyrosine hydroxylase gene delivery to the brain, of hemophilia B by Factor IX gene delivery to the liver, and potentially of myocardial infarction by vascular endothelial growth factor gene to the heart, appear promising since AAV-mediated transgene expression in these organs has recently been shown to be highly efficient (Fisher et al., 1996; Flotte et al., 1993; Kaplitt et al., 1994; 1996; Koeberl et al., 1997; McCown et al., 1996; Ping et al., 1996; Xiao et al, 1996).

d. Other Viral Vectors.

Other viral vectors may be employed as expression constructs in the present invention. Vectors derived from viruses such as vaccinia virus (Ridgeway, 1988; Baichwal and Sugden, 1986; Coupar et al, 1988) canary pox virus, and herpes viruses may be employed. These viruses offer several features for use in gene transfer into various mammalian cells.

II. Non-viral Transfer

DNA constructs of the present invention are generally delivered to a cell, in certain situations, the nucleic acid to be transferred is non-infectious, and can be transferred using non-viral methods.

Several non-viral methods for the transfer of expression constructs into cultured mammalian cells are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al, 1984), direct microinjection (Harland and Weintraub, 1985), DNA-loaded liposomes (Nicolau and Sene, 1982; Fraley et al, 1979), cell sonication (Fechheimer et al., 1987), gene bombardment using high velocity microprojectiles (Yang et al, 1990), and receptor-mediated transfection (Wu and Wu, 1987; Wu and Wu, 1988).

Once the construct has been delivered into the cell the nucleic acid encoding the therapeutic gene may be positioned and expressed at different sites. In certain embodiments, the nucleic acid encoding the therapeutic gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In a particular embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). The addition of DNA to cationic liposomes causes a topological transition from liposomes to optically birefringent liquid-crystalline condensed globules (Radler et al, 1997). These DNA-lipid complexes are potential non-viral vectors for use in gene therapy.

Liposome-mediated nucleic acid delivery and expression of foreign DNA in vitro has been very successful. Using the β-lactamase gene, Wong et al., (1980) demonstrated the feasibility of liposome-mediated delivery and expression of foreign DNA in cultured chick embryo, HeLa. and hepatoma cells. Nicolau et al., (1987) accomplished successful liposome-mediated gene transfer in rats after intravenous injection. Also included are various commercial approaches involving "lipofection" technology.

In certain embodiments of the invention, the liposome may be complexed with a hemagglutinating virus (HVJ).

This has been shown to facilitate fusion with the cell membrane and promote cell entry of liposome-encapsulated DNA (Kaneda et al., 1989). In other embodiments. the liposome may be complexed or employed in conjunction with nuclear nonhistone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention.

Other vector delivery systems which can be employed to deliver a nucleic acid encoding a therapeutic gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferring (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example. Nicolau et al, (1987) employed lactosyl-ceramide, a galactose-terminal asialganglioside, incorporated into liposomes and observed an increase in the uptake of the insulin gene by hepatocytes. Thus, it is feasible that a nucleic acid encoding a therapeutic gene also may be specifically delivered into a cell type such as prostate, epithelial or tumor cells, by any number of receptor-ligand systems with or without liposomes. For example, the human prostate-specific antigen (Watt et al, 1986) may be used as the receptor for mediated delivery of a nucleic acid in prostate tissue.

In another embodiment of the invention, the expression construct may simply consist of naked recombinant DNA or plasmids. Transfer of the construct may be performed by any of the methods mentioned above which physically or chemically permeabilize the cell membrane. This is applicable particularly for transfer in vitro. however, it may be applied for in vivo use as well. Dubensky et al., (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. It is envisioned that DNA encoding a CAM also may be transferred in a similar manner in vivo and express CAM.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al, 1987). Several devices for accelerating small particles have been developed. One such device relies on a high voltage discharge to generate an electrical current, which in turn provides the motive force (Yang et al, 1990). The microprojectiles used have consisted of biologically inert substances such as tungsten or gold beads 8. Formulations and Routes for Administration to Patients Where clinical applications are contemplated, it will be necessary to prepare pharmaceutical compositions-expression vectors, virus stocks, proteins, antibodies and drugs—in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra.

The active compounds also may be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all msolvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient also may be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

9. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

General Methods Employed in the Identification of the FJP Gene

To determine the role of the DPC gene, DNA extracted from sporadic colorectal cancers which will be used. A database has been established for these tumors, containing clinical, pathologic, and follow-up information on these patients. A useful initial approach to study these limited resources would be evaluation for loss of heterozygosity of STRPs flanking the DPC4 gene. Those tumors which have heterozygous deletions of the DPC gene will be analyzed by SSCP for the most common exons harboring mutations. Tumors demonstrating, gel shifts will be directly sequenced.

Northern Blotting

Expression of DPC4 can be studied by hybridization to Northern blots containing poly A+ RNA from a variety of human tissues. Blot MTN blot #7759-1 (Clontech, Palo Alto, Calif.), which contains spleen, thymus, prostate, testis, ovary, small intestine, colon, and peripheral lymphocytes can be used for these purposes. DPP4 can be labeled by end-labeling one PCR primer for a fragment of the gene with [$\gamma$-$^{32}$P]dATP (Sambrook et al., 1989), and beta-actin using [$\alpha$-$^{32}$P]dCTP by the random primer method (Feinberg and Vogelstein, 1984). Blots may be pre-hybridized in ExpressHyb solution (Clontech) at 68° C. for 30 minutes, the radiolabeled probe added. then followed by continuous shaking for 1 hour. Membranes are washed in 2×SSC, 0.05% SDS for 15 minutes at room temperature, then twice at 50° C. in 0.1×SSC, 0.1% SDS for 15 minutes. For visualization. blots are exposed to Kodak XAR film for 2–4 hrs. at room temperature.

Southern Blotting

5 $\mu$g of DNA from family members are digested with the restriction enzymes (such as BamHI, EcoRI, HindIII, NdeI, and PvuII) under conditions recommended by the manufacturer. These digests are then electrophoresed through 0.8% agarose gels, and southern transfer performed. cDNA or PCR™ for DPC4 are hybridized to these blots, in order to determine whether there are alterations in the size of the gene product. Changes which do not appear to be polymorphisms will prompt further in-depth evaluation-of the DPC4.

PFGE Mapping

Restriction enzyme digests of high molecular weight DNA from patients are performed using 1% agarose plugs equilibrated in 200 μl of 1×buffer and 0.25 units/μl of restriction enzyme, using conditions as described by the manufacturer. PFGE of digested plugs is performed in 0.5×TBE, and performing PFGE using a CHEF DRII apparatus (BioRad, Hercules, Calif.). Gels are generally run at 16° C. using a ramped switching time of 2–20 seconds over 18 hours. as described in Howe et al (1993). Gels are depurinated by treatment with 0.25 M HCl for 10 minutes, neutralized in 0.5 M NaOH/1.5 M NaCl, then alkaline transfer to nylon membranes is achieved in 0.25 M NaOH/ 1.5 M NaCl. Hybridization using radiolabeled lambda phage, PCR products from DPC4 amplified from normal human DNA, and YAC end clone sequences is performed identify large rearrangements in the region of the DPC4 gene. Size markers used are λ phage concatomers (Carle and Olson, 1984).

SSCP

Primers were designed for each DPC4 exon using the Primer3 server (http://www-genome.wi.mit.edu/cgi-bin/primer/primer3.cgi). The procedure used for SSCP will involve standard PCR amplification of each exon, mixing this with 5 μl of stop solution (95% formamide/10 mM NaOH/0.05% xylene cyanol/0.05% bromophenol blue), and heating samples to 95° C. for 3 minutes. 3 μl of this mixture is then loaded onto 5% non-denaturing polyacrylamide gels and run in 1×TBE at 10 watts for 12–16 hours using several gel conditions, then silver-stained. Mutations are identified by gel shifts differing from that of the wild-type sequences.

Sequencing of Candidate Genes

When gel shifts are identified, these PCR products can be directly sequenced. Prior to sequencing, the PCR products are electrophoresed through 2% agarose gels, stained with ethidium bromide, and analyzed to determine whether a strong, single band of the expected size is present. If so, then the PCR reaction products are purified using the Qiaquick PCR purification kit (Qiagen, Santa Clarita, Calif.) then reanalyzed for concentration and a single product by gel electrophoresis. If a few different product sizes are found for an exon, then the PCR conditions are re-optimized, and if on repeat analysis there remain a few discrete bands, the correct size band is cut out and DNA recovered using the Qiaquick gel extraction kit (Qiagen, Santa Clarita, Calif.).

Sequencing of these products is carried out using the ABI Prism Dye Terminator Cycle Sequencing kit (Applied Biosystems, Foster City, Calif.), usually using the individual PCR primers to sequence the complementary strand in separate reactions. Occasionally new sequencing primers need to be synthesized when results using the PCR primers are poor. Sequence analysis software is used to identify mutations relative to the wild-type sequence.

Identifying Changes in Transcript Size

Changes predicted to result in alteration in the size of the RNA transcript (i.e. stop codons or alterations in splice sites) are confirmed by extraction of total RNA from a panel of affected and unaffected individuals (using the S.N.A.P. Total RNA isolation kit, Invitrogen, San Diego, Calif.), reverse transcriptase PCR with oligo-dT primers to generate CDNA (CDNA Cycle kit, Invitrogen), and PCR amplification of overlapping fragments of the gene followed by gel electrophoresis to demonstrate a reduction in the size of the transcripts.

Analysis of New JP Patients

The DPC4 can be analyzed for mutations in each FJP family. Since mutations may be clustered in highly conserved regions of a gene, these exons will be studied first in new families. The initial screening can be by SSCP of the most highly conserved exons, followed by sequencing if gel shifts are observed. If shifts on SSCP are not found using a variety of different gel conditions for these most conserved exons, then the remaining exons can be analyzed by SSCP. If no changes are observed then these exons can be directly sequenced in an affected member of the family. When base changes relative to the wild-type sequence are found, they can be examined in the rest of the family as well as in unrelated individuals. If mutations are still not found in this gene in new families which appear linked to 18q21, then they will be evaluated for alterations in splicing which may have been missed by direct sequencing or SSCP.

LOH Studies

Recent deletion mapping of sporadic colorectal cancers have defined an interval on 18q21 spanning from STRP D18S535 to D18S858 (Thiagalingam et al, 1996), which is essentially the same interval that the JP gene has been mapped to herein. As JP is caused by a tumor suppressor gene as described herein, then LOH studies (comparing the genotypes found in normal cells (lymphocytes) with those of tumors from JP patients) should provide another means of identifying a role for DPC4 in the development of these tumors.

DNA Extraction

This technique begins with careful pathologic review of specimens removed at endoscopy or surgery from family members to confirm the presence of juvenile polyps, adenomatous polyps, or adenocarcinoma. Paraffin sections 10 microns in thickness are cut from the corresponding blocks, and tissue from the critical histologic regions of each slide is microdissected. Multiple microdissected sections are pooled for each paraffin block, then DNA extracted using the method described (Howe et al, 1997). Briefly, samples are deparaffinated by adding 1 ml. of xylene to tubes containing pooled sections, then gently vortexed for 5 minutes at room temperature. Tubes are then centrifuged at 14000 rpm for 5 minutes, and the supernatant removed. This step is repeated, then 1 ml. of room temperature, 100% ethanol is added, samples mixed for 2–3 minutes, then centrifuged at 14000 rpm for 5 minutes. Residual ethanol is removed by pipetting followed by centrifugation in a vacuum-concentrator for 10 minutes. 200 ull of proteinase K digestion buffer are added to each tube (50 mM Tris-HCl pH 8.5, 1 mM EDTA pH 8.0. 0.5% Tween 20), then Proteinase K added to a final concentration of 400 μg/ml. Samples are incubated at 50° C. for 4–6 hours, then heated to 94° C. for 10 minutes to inactivate the proteinase K. 50 μl of a saturated NaCl solution (approximately 6M) is added to each tube, tubes are shaken, then centrifuged at 4000 rpm at room temperature for 15 minutes, and the supernatant removed to a fresh tube. One-tenth volume of 3M sodium acetate, 2.5 volumes of 100% ethanol, and 5 μl of mussel glycogen (2 mg/ml) are added, and samples are placed at −20° C. overnight. Tubes are centrifuged at 4° C. and 14000 rpm for 30 minutes, then the supernatant is removed. DNA pellets are washed with 1 ml of 70% ethanol, resuspended in 50 μl of sterile water, and their absorbance measured at 260 and 280 nm in a UV spectrophotometer. This technique yields quality DNA for PCR and sequencing. DNA has been extracted from 14 tumors from 8 members of the Iowa FJP kindred by this method thus far, as listed in Table 3.

Testing for LOH

LOH studies will be performed by the amplification of chromosome, 8q21 STRPs (Table 7) for which these family members have been found to be heterozygous. DNA extracted from peripheral lymphocytes and from these tumors will be used as template in separate PCR reactions using a fluorescent-labeled prime. These products will be run through the Applied Biosystems Model 310 Genetic Analyzer for the flubrimetric detection of signal intensities for each allele. Intensity data for normal and tumor alleles will be analyzed using a computer algorithm developed for deletion studies (Newton et al., 1994).

TABLE 4

Tumor samples from members of the Iowa FJP kindred which have been microdissected and DNA extracted.

| Patient Number | Accession Number | Diagnosis |
|---|---|---|
| III-18 | 3166-73 | rectal juvenile polyp with adenomatous regions |
| IV-9 | S82-639-3 | gastric juvenile polyp |
| | S83--8202-2 | colonic juvenile polyp with atypia |
| | S84-1709 C | colonic juvenile polyp with atypia |
| IV-17 | S74-10886 A3 | colonic adenoma |
| | S74-10886 B | colonic adenoma, low grade dysplasia |
| | S80-5859-1 | colonic juvenile polyp with atypia |
| | S96-5977 C1 | rectal juvenile polyps |
| IV-21 | SL944970 | colonic juvenile polyps |
| IV-22 | S96-6100 A3 | colonic juvenile polyps |
| IV-23 | S93-18596 A1 | colonic juvenile polyp |
| IV-24 | S-604-92 | colonic juvenile polyp with atypia |
| | S-2215-95 | colonic juvenile polyp with atypia |
| V-4 | S89-3519 A9 | colonic juvenile polyp |

Example 2

Previous Genetic Mapping Studies of 18q21

The present invention is drawn to the identification of the genetic locus for and mutation that result in juvenile polyposis. The present Example provides a background for selecting candidate genes from the region of 12q21 ultimately chosen by the inventor. The linkage strategy involved genotyping of single tandem repeat polymorphisms (STPPs) near loci known to play an important role in colorectal polyposis or cancer; after testing of 10 loci, linkage was found to markers 18q21.

A large number of genes and/or genetic disorders have been mapped to chromosome 18q21, including DCC, DPC4, MADR2, FECH (ferrochelatase), NARS (asparaginyl-tRNA synthetase), CORD (cone rod dystrophy 1), F5F8D (coagulation factor V-factor VIII deficiency), BRIC (benign recurrent intrahepatic cholestasis), IDDM6 (insulin dependent diabetes mellitus 6), FEO (familial expansile osteomyelitis), SCCAJ (squamous cell carcinoma antigen 1), SSCA2 (squamous cell carcinoma antigen 2), MC4R (melanocortin 4 receptor), FVT1 (follicular lymphonma variant translocation I), BCL2 (B cell lymphoma 2), PA12 (plasminogen activator inhibitor type 2), and GRP (gastrin-releasing polypeptide). The STS-based map of the human genorne from the Whitehead Institute for Biomedical Research/MIT Center for Genome Research has helped to define the physical map of this region, and was constructed by screening 10,000 STSs in the CEPH YAC library and radiation hybrid mapping of 14665 markers (Hudson et al., 1995). Several independent groups have also significantly contributed to the mapping of this region, as summarized in the 4th international workshop on chromosome 18 mapping (Silverman et al., 1996). These data suggest that the FJP gene lies on the subregion 18q21.1, which would allow for the exclusion of the BRIC, SCCA1, SCCA2, FVTI, PA12, BCL2, FECH, and GRP genes. A number of ESTs have been mapped to this interval, including R01897, Ht3498, W46404, R43753, H83795, T02923, R44040, N64773, AA035555, H85419, H38158, D16294, N29319, H02272, X52839, U55777, T62080, T16783. All of the markers used in the linkage studies from the Iowa FJP kindred were contained within the YAC contig WC18.4, which spans from 297 cR/ 63 cM to 511 cR/114 cM on chromosome 18. Critical recombinants in the Iowa FJP kindred define the FJP gene interval between 344 cR/68 cM and 378 cR/77 cM.

The finding of linkage with no recombinants to an intragenic polymorphism within the DCC gene (lod 4.79 at q=0.001), plus the possibility that DCC plays an important role in the genesis of sporadic colorectal tumors led us to look for mutations within the DCC gene. The coding sequence of DCC was retrieved from Genbank (Accession #X76132), the intron-exon boundaries from Cho et al. (1994), and then separate files were created for each of the 29 exons. Primers for each exon were chosen using the Primer3 program [(http://www-genome.wi.mit.edu/cgi-bin/primer/primer3.cgi)], and were synthesized by Research Genetics (Huntsville, Ala.). PCR amplification of five individuals (corresponding to individuals III-18, IV-20, IV-22, IV-24, and the spouse of III13 in FIG. 1) was performed for each exon. Single-strand conformational polymorphism (SSCP) analysis was performed by running these products at room temperature or 4° on non-denaturing acrylamide gels (with or without 10% glycerol). Although gel shifts were noted in exons 1, 8, and 16, these shifts did not segregate with the disease phenotype. Since SSCP may only identify up to 70% of mutations, direct sequencing of each exon from a single affected individual was begun. PCR primers were used to sequence both sense and anti-sense strands for each exon by dye terminator cycle sequencing, and run on an ABI Model 373A Sequencer (Foster City, Calif.). The wild-type sequences for each exon were analyzed for differences relative to the sequences obtained for sense and anti-sense strands using the Sequencher software (Gene Codes Corporation, Ann Arbor, Mich.). To date, exons 8, 11, 12, 13, 14, 15, 16, 18, 20, 22, 24, 26, 27, and 29 have been sequenced with good results and no discernible mutations. Sequencing of the remaining exons is ongoing.

The other strong candidate gene from this interval is the DPC 4 gene, which has 11 exons (Hahn et al., 1996). The primers for each exon were obtained from Research Genetics (Huntsville, Ala.), as described by Moskaluk et al.(1997) Direct sequencing of PCR products from individual IV-22 was carried out as discussed for DCC above. A frameshift mutation was detected in exon 9 of DPC4 as described herein, which segregated with the disease phenotype in the Iowa kindred. Subsequent studies revealed the same mutation in JP kindreds from Mississippi and Finland. Two additional nonsense mutations were detected in JP patients within exon 8 and exon 5 of the DPC4 gene.

Example 3

The Gene for Familial Juvenile Polyposis Mapping to Chromosome 18q21.1

Methods

Patients

Informed consent was obtained from family members with the approval of the Institutional Review Board at the University of Iowa. Pathology slides and medical records were reviewed at the University of Iowa to confirm the diagnosis of JP. Individuals were considered to be affected if they had histologic evidence of upper gastrointestinal or colorectal juvenile polyps. Deceased individuals with a history of gastrointestinal cancer and/or affected offspring were also designated as affected. Living kindred members without a definitive histologic diagnosis of FJP were classified as having unknown affection status. Table 4 shows exemplary primers used in sequencing and SSCP analyses.

reaction conditions included 25 ng of DNA; 200 µM each of dGTP, dATP, dTTP, and dCTP; 1 µl of 10×buffer (100 mM Tris-HCl, pH 8.3, 500 mM KCl, 15 mM $MgCl_2$, 0.01% w/v gelatin); 2 pmol of each primer; and 0.375 U Taq DNA polymerase. Samples were incubated in a thermocycler for 1 min at 94° C., 1 min at 55° C. (or optimal annealing temperature), and 1 min at 72° C., for a total of 35 cycles. After amplification, 5 µl of stop solution (95% formamide,

TABLE 5

DPC4 Exon Primers and Annealing Conditions

|  |  |  | Primer types |
|---|---|---|---|
| DCP4 exon 1: | DPC4S1.1 | 5'-AAC GTT AGC TGT TGT TTT TCA C-3' | Initial Primers |
|  | DPC4AS1 | 5'-AGA GTA TGT GAA GAG ATG GAG-3' |  |
|  | DPC41a | 5'-TTG CTT CAG AAA TTG GAG ACA-3' | SSCP and Sequencing |
|  | DPC41b | 5'-GCT TGA AAG GAA ACG TAG CAA-3' | Primers |
| DPC4 exon 2: | DPC4S2 | 5'-TGT ATG ACA TGG CCA AGT TAG-3' | SSCP and Sequencing |
|  | DPC44AS2 | 5'-CAA TAC TCG GTT TTA GCA GTC-3' | Primers |
|  | 2a(SSCP)s | 5'-TGA CAC ATG AAT AAA TGG TCG TT-3' | SSCP and Sequencing |
|  | 2b(SSCP)as | 5'-TTG AGA TCC TTT TCC CTT TAT GTT-3' | Primers |
| DPC4 exon 3: | DPC4S3.1 | 5'-CTG ATT TGA AAT GGT TCA TGA AC-3' | SSCP and Sequencing |
|  | DPC4AS3 | 5'-GCC CCT AAC CTC AAA ATC TAC-3' | Primers |
| DPC4 exon 4: | DPC4S4 | 5'-TTT TGC TGG TAA AGT AGT ATG C-3' | Original combination of |
|  | DPC4AS4.1 | 5'-AAC GTT AGC TGT TGT TTT TCA C-3' | sense and antisense primers |
|  | DPC4S4 | 5'-TTT TGC TGG TAA AGT AGT ATG C-3' | SSCP and Sequencing |
|  | DPC4ex4 | 5'-GGA GTT TCC CCC CAA GTG ACT AC-3' | Primers |
| DPC4 exon 5/6: | DPC4AS5/6.1 | 5'-CAC TAT TTA ATG AAA CAA AAT CAC-3' | Initial Amplification and |
|  | DPC4S5/6 | 5'-CAT CTT TAT AGT TGT GCA TTA -3' | sequencing primers |
|  | 5a(SSCP)s | 5'-GAT GAC ATC TAT GAA TGT ACC ATG T-3' | SSCP |
|  | 5b(SSCP)as | 5'-CCC ACA TGG GTT AAT TTG CT-3' |  |
|  | 6a(SSCP)s | 5'-CTT TTA TAA AAG CAA ATT AAC CCA-3' | SSCP |
|  | 6b(SSCP)as | 5'-AAA AAT AGC CCT TAC AAC AAA AAC A-3' |  |
| DPC4 exon 7: | DPC4S7 | 5'-TGA AAG TTT TAG CAT TAG ACA AC-3' | SSCP and sequencing |
|  | DPC4AS7 | 5'-TGT ACT CAT CTG AGA AGT GAC-3' |  |
| DPC4 exon 8: | DPC4S8 | 5'-TGT TTT GGG TGC ATT ACA TTT C-3' | Initial and Sequencing |
|  | DPC4AS8 | 5'-CAA TTT TTT AAA GTA ACT ATC TGA-3' | primers |
|  | 8a(SSCP)s | 5'-CCT TAT ATC TTT CTC ATG GGA GG-3' | SSCP primers |
|  | DPC4AS8 | 5'-CAA TTT TTT AAA GTA ACT ATC TGA-3' |  |
| DPC4 exon 9: | DPC4S9 | 5'-TAT TAA GCA TGC TAT ACA ATC TG-3' |  |
|  | DPC4AS9 | 5'-CTT CCA CCC AGA TTT CAA TTC-3' |  |
| DPC4 exon 10: | DPC4S10 | 5'-AGG CAT TGG TTT TTA ATG TAT G-3' | SSCP and Sequencing |
|  | DPC4AS10 | 5'-CTG CTC AAA GAA ACT AAT CAA C-3' |  |
| DPC4 exon 11: | DPC4S11 | 5'-CCA AAA GTG TGC AGC TTG TTG-3' | Sequencing primers |
|  | DPC4AS11P2 | 5'-ATT GTA TTT TGT AGT CCA CC-3' |  |
|  | 11a(SSCP)s | 5'-ATC ACC CTG TCC CTC TGA TG-3' | SSCP primers |
|  | 11b(SSCP)as | 5'-TTT TGT AGT CCA CCA TCC TGA-3' |  |

Genotyping Studies

Peripheral blood was drawn and DNA extracted using a salting-out procedure (Miller et al., 1988). Simple-tandem-repeat polymorphism (STRP) markers were selected from different candidate regions according to the relevant literature, contig maps were obtained from the human physical mapping project at the Whitehead Institute for Biomedical Research/MIT Center for Genome Research, and genetic maps were obtained from the Center for Medical Genetics. Of fad Primers were obtained from Research Genetics and were amplified by PCR in a total volume of 10 µl. PCR 10 mM NaOH, 0.05% bromophenol blue, 0.05% xylene cyanol) was added. Samples were heated to 95° C. and were then electrophoresed through 6% denaturing polyacrylamide gels for 2–4 h at 60 W. Gels were silver stained (Bassam et al., 1991), and genotypes were determined from the gels.

Linkage Analysis

Genotype data were entered into a Macintosh computer using a Hypercard-based program (Nichols et al., 1993). Marker data were exported to a DOS-compatible computer, where linkage analysis was performed using the LOD-SCORE and MLINK subroutines of the FASTLINK (2.3)

version (Cottingham et al., 1993) of the LINKAGE program package (Lathrop et al., 1985). Although the gene frequency for FJP is not known, for this study it was estimated to be 1/100,000. This was based on Burt's estimate that FJP is less common than PJS, which is approximately one-tenth as common as familial adenomatous polyposis (which has an incidence of 1 in 8,000) (Burt et al., 1993). Complete dominance of the disease allele (A) was assumed, and penetrance was set at AA=0.95, Aa=0.95, and aa=0.00. For chromosome 18q markers, linkage was also calculated with penetrance values as described for HMPS (AA=0.95, Aa=0.95, and aa=0.075) (Thomas et al., 1996). No age-specific liability classes were used to further estimate penetrance. Since allele frequencies could not be reliably established in this one kindred with few spouses, initial linkage analyses were performed using equal allele frequencies. For markers from 18q, analyses were performed using equal frequencies as well as those from the CEPH database.

Results

FJP Kindred

Linkage Analysis

Genotyping was performed on 43 individuals, of whom 13 were affected (all with a histologic diagnosis of gastrointestinal juvenile polyps), 24 were considered to be at risk, and 6 were spouses. The linkage strategy involved the typing of markers at loci known to play an important role in colorectal polyposis or cancer. This included the regions of MSH2 (2p16), MLHI (3p21), MCC, APC (5q21-22), HMPS (6q21), PTEN (10q22-24), KRAS2 (12p12), TP53 (17p13), DCC (18q21), and LKB1 (19p). Markers in the region of CDKN2A (9q21) were also studied.

Table 6 summarizes the findings of linkage analysis with most of these markers. There was no evidence to suggest linkage to loci predisposing to hereditary nonpolyposis colorectal cancer (MSH2 and MLH1) or familial adenomatous polyposis (APC), or to several loci known to play an important role in the genesis of sporadic colorectal cancer (MCC, KRAS2, and TP53). There was also no evidence for linkage to loci involved in other hamartomatous polyposis syndromes, including HMPS, PTEN, and LKB1. Linkage of JP to a putative tumor-suppressor gene on 10q22-24 (JP1) was also not suggested by these data.

In contrast, strong evidence for linkage to markers on 18q21.1 was found. The two-point maximum likelihood data for 27 18q markers are summarized in Table 7. Seven markers had LOD scores exceeding 3.0, with a maximum LOD (Zmax) of 5.00 at D18S1099 ($\theta$=0.001). All of these markers have been mapped to the YAC contig WC18.4. Five affected individuals had recombination events detected with these 18q21 markers: IV-11 with D18S548; IV-7 with D18S460, D18S970, and D18S118; 111–13 with D18S970 and D18S1118; IV-2 with D18S487, D18S858, D18S849, and D18S/147; and II4 with D18S862 and D18S!147.

Analysis of these critical recombinants places the FJP gene between D18S1118 and D18S487 (FIG. 2), an interval of ~1.9 cM and 34 cR (Center for Medical Genetics, Whitehead Institute for Biomedical Research/MIT Center for Genome Research). The DCC gene was placed within this interval by means of the GeneBridge 4 radiation-hybrid panel (Walter et al., 1994), between WI-5257 and WI-4115.

TABLE 6

Pairwise LOD Scores for FJP versus Candidate-Region STRPs

| STRP | Recombination Fractions | | | | | | |
|---|---|---|---|---|---|---|---|
| | 0.00 | 0.01 | 0.05 | 0.10 | 0.20 | 0.30 | 0.40 |
| D2S123 | −10.41 | −3.69 | −1.63 | −0.81 | −0.18 | 0.02 | 0.06 |
| D2S1352 | −26.24 | −7.21 | −5.46 | −1.75 | −0.56 | −0.12 | 0.03 |
| D2S1364 | −9.02 | −1.41 | −0.10 | 0.31 | 0.45 | 0.33 | 0.15 |
| D3S1611 | −15.40 | −4.66 | −2.07 | −1.10 | −0.37 | −0.10 | 0.00 |
| D3S1768 | −4.15 | −1.77 | −0.43 | 0.02 | 0.24 | 0.18 | 0.06 |
| D5S1453 | −26.68 | −10.41 | −5.23 | −3.07 | −1.22 | −0.43 | −0.10 |
| D5S1467 | −14.96 | −4.43 | −1.83 | −0.88 | −0.20 | −0.03 | −0.02 |
| D5S346 | −7.48 | −1.53 | −0.31 | 0.08 | 0.22 | 0.12 | 0.00 |
| D6S1028 | −9.01 | −1.26 | −0.08 | 0.26 | 0.34 | 0.23 | 0.10 |
| D6S283 | −7.91 | −1.39 | 0.38 | 0.86 | 0.91 | 0.61 | 0.26 |
| D6S301 | −8.43 | −1.35 | −0.17 | 0.16 | 0.21 | 0.09 | 0.01 |
| D6S434 | −18.77 | −3.78 | −1.21 | −0.34 | 0.16 | 0.16 | 0.08 |
| D6S475 | −18.98 | −6.78 | −3.29 | −1.87 | −0.70 | −0.24 | −0.06 |
| D9S259 | −14.28 | −4.55 | −1.96 | −1.00 | −0.30 | −0.07 | −0.01 |
| D9S304 | −14.15 | −4.36 | −2.00 | −1.01 | −0.22 | 0.03 | 0.07 |
| D9S319 | −13.91 | −4.46 | −1.53 | −0.34 | 0.51 | 0.63 | 0.41 |
| D10S1242 | −17.49 | −6.51 | −3.08 | −1.72 | −0.59 | −0.17 | −0.03 |
| D10S1427 | −3.53 | 0.45 | 0.93 | 0.95 | 0.71 | 0.42 | 0.17 |
| D10S215 | −13.31 | −3.03 | −1.13 | −0.47 | −0.05 | −0.01 | −0.06 |
| D10S219 | −5.44 | −1.55 | −0.32 | 0.12 | 0.39 | 0.35 | 0.19 |
| D10S1753 | −5.04 | −0.72 | 0.42 | 0.71 | 0.68 | 0.42 | 0.14 |
| D10S573 | −9.77 | −5.29 | −2.49 | −1.36 | −0.43 | −0.11 | −0.02 |
| D12S372 | −9.68 | −3.52 | −1.54 | −0.79 | −0.22 | −0.04 | 0.01 |
| D12S389 | −9.71 | −4.94 | −2.25 | −1.21 | −0.40 | −0.12 | −0.03 |
| D17S922 | −9.04 | −1.72 | −0.53 | −0.17 | 0.02 | 0.03 | 0.01 |
| D17S953 | −9.63 | −3.94 | −1.67 | −0.76 | −0.09 | 0.09 | 0.08 |
| D17S960 | −9.97 | −2.18 | −0.78 | −0.28 | 0.01 | 0.04 | 0.02 |
| D17S969 | −9.45 | −2.45 | −0.61 | −0.03 | 0.26 | 0.23 | 0.12 |
| D19S565 | −24.77 | −9.27 | −4.61 | −2.77 | −1.17 | −0.49 | −0.20 |
| D19S886 | −3.57 | −1.36 | −0.16 | 0.19 | 0.29 | 0.18 | 0.05 |
| D19S894 | −7.20 | −0.82 | 0.93 | 1.39 | 1.36 | 0.95 | 0.45 |

TABLE 7

Pairwise Linkage Results of FJP versus Chromosome 18 STRPs

| STRP | $\theta$ at Zmax | Zmax |
|---|---|---|
| D18S978 | 0.140 | 0.84 |
| D18S548 | 0.080 | 1.03 |
| D18S460 | 0.157 | 0.37 |
| D18S970 | 0.500 | 0.00 |
| D18S1118 | 0.152 | 0.57 |
| D18S473 | 0.001 | 2.14 |
| D18S470 | 0.001 | 2.59 |
| D18S1110 | 0.001 | 2.47 |
| D18S474 | 0.001 | 4.24 |
| D18S1099 | 0.001 | 5.00 |
| D18S46 | 0.001 | 4.41 |
| D18S363 | 0.001 | 4.46 |
| DCC | 0.001 | 4.79 |
| GATA06 | 0.001 | 2.36 |
| D18S1156 | 0.001 | 1.37 |
| D18S851 | 0.016 | 1.60 |
| D18S484 | 0.025 | 3.31 |
| D18S539 | 0.013 | 2.10 |
| D18S487 | 0.111 | 1.22 |
| D18S69 | 0.065 | 1.42 |
| D18S846 | 0.001 | 1.46 |
| D18S858 | 0.048 | 3.20 |
| D18S977 | 0.001 | 2.69 |
| D18S849 | 0.105 | 2.58 |
| D18S862 | 0.229 | 0.32 |
| D18S1147 | 0.174 | 1.51 |
| D18S979 | 0.420 | 0.03 |

Linkage analysis was performed under several different assumptions, without changing the overall results. First, clinically unaffected individuals were scored as unknown, with a penetrance of 95% for genotype AA, 95% for Aa, and 0% for aa. Next, four individuals >50 years of age, with negative colonoscopy or barium enema results, were classified as unaffected, and the same penetrance values were used as described for HMPS (AA=95%, Aa=95%, aa=7.5%) (Thomas et al., 1996). LOD scores of >3.0 were found with the same seven markers (D18S474, D18S1099, D18S46, D18S363, DCC, D18S484, and D18S858) with assumptions, using the allele frequencies in the CEPH database, without significant differences in recombination fraction (θ). Linkage analysis was also performed using equal allele frequencies, which resulted in LOD scores of >3.0 with 10 different markers (D18S470, D18S1110, D18S474, D18S099, D18S46, D18S363, DCC, D18S484, D18S846, and D18S977). The data reported in Table 7 were derived by means of the first method described, which appeared to use the most conservative assumptions for linkage analysis. Linkage analysis was also performed by classifying deceased individuals with a history of GI cancer and/or affected offspring (but without histologic confirmation of juvenile polyposis) as having unknown affection status, which did not change these results.

Discussion

FJP is the last of the hamartomatous polyposis syndromes to be localized by genetic linkage analysis. The focused genome screen used here identified a locus on chromosome 18q21.1, which is at variance with the previous suggestion of a tumor-suppressor gene (JP1) for FJP on 10q22-24 (Jacoby et al., 1997a). There was no evidence of linkage to the 10q markers used here, which spanned the 10q22-24 region containing the PI-EN gene.

It is worth noting that identification of JP1 was based on loss-of-heterozygosity studies and not on genetic linkage. Jacoby et al., (1997a) found deletion of one allele of D10S219 in 39 (83%) of 47 juvenile polyps, and fluorescent in situ hybridization demonstrated that 10q deletions occurred within the lymphocytes and macrophages of the lamina propria, but not in epithelial cells. These results supported the theory that overgrowth of the lamina propria is the determining event in juvenile polyp formation (Jass 1990). Recent reports that four individuals with juvenile polyposis had PTEN germline mutations would appear to confirm that PTEN is the predisposing gene on 10q22-24 in some families with juvenile polyposis (Lynch et al., 1997; Olschwang et al., 1998). However, one of these patients was described as having both CD and juvenile polyposis (Lynch et al., 1997), whereas the other three had no family history of juvenile polyposis (and one of these had a thyroid nodule) (Olschwang et al., 1998). These reports raise the question whether these patients were truly affected with juvenile polyposis or CD (Eng and Ji 1998).

In 14 JP families, Marsh et al., (1997) found no evidence of linkage to markers on 10q22-24 or mutations in the PTEN gene, which they concluded ruled out PTFN or another gene in this region as the locus for JP, at least in a subset of these families. Similar results were found by Riggins et al., (1997) and are in agreement with the findings of the present study, which would rule out germline mutations on 10q22-24 as the predisposing event leading to JP in this large family. It is likely that there is genetic heterogeneity for the juvenile polyposis syndromes, and perhaps mutations at HMPS and PTEN represent the changes seen in some families, whereas a locus for generalized polyposis predisposing to gastrointestinal carcinoma resides on 18q21.1.

The findings of the present invention should help to establish JP as a distinct entity rather than a variant of one of the other hamartomatous polyposis syndromes, such as PJS on 19p13 or CD on 10q23. Genetic methods will ultimately prove to be more useful for the classification of different families with hamartomatous polyposis than current methods based on clinical phenotype.

Analysis of critical recombinants places the FJP gene in an 11.9-cM interval between the markers D18S1118 and D18S487 (Center for Medical Genetics). Linkage analysis revealed no recombinants with the markers D18S473, D18S470, D18S110, D18S474, D18S1099, D18S46, D18S363, DCC, GATA06, D18S1156, D18S846, or D18S977 (the latter two markers being telomeric to the interval defined by critical recombinants). The finding of genetic linkage with markers on 18q21.1 makes presymptomatic testing of at-risk individuals in this family possible. This would allow those who have not inherited the affected parental allele to potentially be spared from repetitive endoscopic screening for GI neoplasms, whereas those predicted to be gene carriers would benefit from close surveillance for the development of these tumors. Although prophylactic surgery has been proposed (Scott-Conner et al., 1995), this may not be necessary if periodic screening and endoscopic polypectomy are carried out.

One candidate gene from 18q21.1 that can be excluded from consideration as the FJP gene is MADR2, which has been physically mapped to between D18S460 and D18S970 (Eppert et al., 1996), centromeric to the recombination events seen in individuals III-13 and IV-7. This interval on 18q-21.1 does contain DCC, a tumor-suppressor gene lost in many sporadic colorectal carcinomas (Vogelstein et al., 1988; Fearon et al., 1990).

DCC spans ~1.4 Mb in genomic DNA (Cho et al., 1994) and has been shown to encode for a netrin receptor (Keino-Masu et al., 1996). Its role in the genesis of colorectal carcinoma is uncertain, since transgenic mice lacking a functional DCC gene manifest not an increased rate of intestinal tumors, but rather defects in commissural axon projections (Fazeli et al., 1997). The latter study concluded that the loss of DCC expression commonly seen in colorectal and pancreatic cancers may be related to changes in a linked gene.

The simian sarcoma associated virus-1 gene (SAV1) also lies within this interval (Eppert et al., 1996) and contains sequences resembling retrovirus long-terminal repeats (Brack-Werner et al., 1989). Also mapping to this region is DPC4, a member of the Mad gene family, involved in signal transduction of serine threonine kinase receptors (Hahn et al., 1996b). Interestingly, the gene for PJS has just been found to be caused by mutations in the serine threonine kinase gene LKBI (Hemminki et al., 1998).

DPC4 is homozygously deleted in ~30% of pancreatic carcinomas, and gene mutations are seen in 22% of pancreatic tumors without homozygous deletions (Hahn et al., 1996b). DPC4 was also found to be lost or altered in 5 (28%) of 18 colorectal carcinoma cell lines (Thiagalingam et al, 1996). The latter study defined the minimally lost region in 55 colorectal carcinoma cell lines to span the 16-cM interval between D18S535 and D18S858, which contains both the DCC and DPC4 genes. This is roughly the same interval to which the FJP gene has been mapped in this study, except that this interval begins 4 cM telomeric to D18S535 and ends 4 cm centromeric to D18S858 (Center for Medical Genetics). These results suggest that the gene responsible for JP could be the same gene on 18q21 that is involved in the development of sporadic colorectal or pancreatic carcinomas; whether this gene will prove to be DCC or DPC4 awaits direct mutational testing in JP family members.

Example 4

Mutations in DPC4 lead to Juvenile Polyposis

Example 3 describes the mapping of a gene predisposing to JP to chromosome 18q21.1, between markers D18S1118 and D18S487. This is an interval that contains the two putative tumor suppressor genes DCC and kSMAD4 (Eppert et al., 1996). The present method identifies SMAD4 or DPC4 as the gene predisposing to juvenile polyposis.

Methods

Primers were designed for exons 1 to 29 of DCC using the Primer3 server and the published intron-exon boundaries (Schutte et al., 1996). Primers for amplification of the SMAD4 gene have been previously described (Moskaluk et al., 1997). PCR was performed in a 10 μl volume that included 25 ng of DNA, 200 μM each of dGTP, dATP, dTTP, and dCTP, 1 μl of 10×buffer [100 mM Tr's-HCl (pH 8.3), 500 mM KCl, 15 mM $MgCl_2$, 0.01% wt/vol gelatin], 2 pmol of each primer, and 0.25 units of Taq DNA Polymerase. PCR was performed for 1 min at 94°, 1 min at 55° (or optimal annealing temperature), and 1 min at 72° for a total of 30 cycles After amplification, 5 μl of stop solution (95% formamide, 10 mM NaOH, 0.05% bromophenol blue, 0.05% xylene cyanol) was added, samples were heated to 95° C. for 3 min, then loaded onto 6% nondenaturing polyacrylamide gels (with and without 10% glycerol. DNA was detected by silver staining. Informed consent for DNA studies was obtained from family members with the approval of the Institutional Review Board at the University of Iowa.

Exon 9 of DPC4 was PCR amplified and the gel products purified and ligated into the p-GEM-T Easy plasmid vector (Promega, Madison, Wis.). JM109 cells were transformed with the vector and then plated onto LB/Ampicillin plates containing 0.5 mM isopropylthio-β-D-galactoside and 80 μg/ml 5-bromo-4-chloro-3-indolyl-β-D-galactoside. Recombinant clones were grown-overnight at 37° C. in LB/Ampicillin (100 μg/ml) medium. Cells were harvested and lysed and cycle sequencing was performed using DPC4S9 and AS9 primers.

PCR products were subjected to electrophoresis through 2% agarose gels, and stained with ethidium bromide to confirm the presence of a single band of the expected size. The products were isolated using the Qiaquick PCR purification kit (Qiagen, Santa Clarita, Calif.) and then sequenced using the ABI Prism Dye Terminator Cycle Sequencing kit (PE Applied Biosystems, Foster City, Calif.). Cycle sequencing included 1 cycle at 98° C. for 5 min, followed by 30 cycles at 94° C. for 10 s, 50° C. for 5 s, and 60° C. for 4 min. Individual PCR primers were used for sequencing the sense and antisense strands for each exon. Reactions were analyzed with an ABI Model 373XL stretch fluorescent automated sequencer.

Results and Discussion

The high incidence of colorectal cancer (as well as one case of pancreatic cancer) in affected members of the JP kindred displaying 18q21 linkage (the Iowa JP kindred) (Stemper et al., 1975), led to the idea that one of these tumor suppressor genes could be the gene predisposing to JP. Because of the complexity of DCC (29 exons spanning 1.4 megabases (Cho et al., 1994)), the inventors initially searched for germline mutations by SSCP analysis of five family members (three affected, two unaffected). Shifts were detected in exons 1, 8, and 16, but these did not cosegregate with the disease.

The inventors then changed their mutation screening strategy and began sequencing genomic polymerase chain reaction (PCR) products generated from one affected individual for each exon of DCC and SMAD4. After sequencing 14.DCC exons and all 11 SMAD4 exons, the inventors detected a 4 base-pair deletion in exon 9 of SMAD4. The patient's affected brother had the same heterozygous deletion and his unaffected mother had the wild-type sequence for exon 9. To confirm this mutation, the inventors subcloned the exon 9 PCR product from this patient into a plasmid vector and sequenced the individual alleles. One allele was the wild type and the other had a 4 base-pair deletion (FIG. 3) between nucleotides 1372 and 1375 (codons 414 to 416) of the cDNA sequence (GenBank Accession No. U44378 (Hahn et al., 1996)). This deletion causes a frameshift that creates a new stop codon at the end of exon 9 (nts 1432 to 1434 of the wild-type sequence. codon 434).

The inventors next analyzed exon 9 of SMAD4 from all 46 members of the Iowa JP kindred by PCR amplification and denaturing polyacrylamide gel electrophoresis. The altered allele was present in all 13 affected individuals, none of 7 spouses, and 4 of 26 individuals at risk (two-point lod score of 5.79, 0=0.00). This altered allele was also readily observed on SSCP gels (FIG. 4). To exclude the possibility that this alteration represented a polymorphism, the inventors amplified exon 9 from 242 unrelated individuals (484 chromosomes). The altered allele was not observed in this population. DNA extracted from GI polyps was also used to amplify SMAD4 exon 9. This analysis revealed loss of the wild-type allele in 1 of 11 tumors derived from 5 affected individuals (FIG. 5).

Eight additional unrelated JP patients were subsequently analyzed for mutations of all exons of SMAD4 by SSCP and genomic sequencing (Table 6). Two JP kindreds were found which segregated a similar 4-base-pair deletion in exon 9. Due to the nature of the sequence in this region, these deletions can begin at any of four consecutive nucleotides and result in the same mutant. sequence and new stop codon. The three kindreds segregating these deletions were all Caucasian, and originated from Iowa. Mississippi, and Finland. There was no common ancestral haplotype, as assessed by analysis of microsatellite markers close to SMAD4.

Sequencing did not reveal any intragenic polymorphisms that would be useful in evaluating common ancestry, and it is unclear whether this defect is an ancestral founder mutation or a mutational hotspot. A patient with colonic and gastric juvenile polyposis (whose father has a history of GI symptoms but has not been evaluated clinically) was found to have a 2-base-pair deletion in exon 8 of SMAD4, at nts 1170–1171 (codon 348). This deletion causes a frameshift that creates a stop codon at nts 1178–1180 (codon 350). Another patient diagnosed with 30–40 colonic juvenile polyps at age 6 but with no family history of JP (four siblings and both parents unaffected) was found to have a 1-base-pair insertion between nts 815–820 of exon 5; this change added a guanine to a stretch of six sequential guanines in the wild-type sequence, and created a frameshift and a new stop codon at nucleotides 830–832 (codon 235). No SMAD4 mutations were found in four other unrelated JP patients.

SMAD4 is a 552-amino-acid protein (Hahn et al., 1996). Its carboxy terminus appears to be important for the formation of SMAD4 homo-trimers, which then complex with other SMADs. Mutations that disrupt homo-trimer formation lead to loss of TBF-β signaling (Shi et al., 1997). A SMAD4 mutant lacking COOH-terminal amino acids has a dominant negative effect on SMAD2-mediated mesoderm induction in Xenopus embrvos, and forms oligomers with wild-type SMAD4 that may be responsible for this loss of activity (Lagna et al., 1996). The majority of somatic mutations described in SMAD4 map to the carboxy terminus between codons 330 and 526 (Hahn et al., 1996; Schutte et al., 1996; Takagi et al., 1996; Kim et al. 1996), within several highly conserved domains. The 4-base-pair deletion detected in three JP families is predicted to produce a COOH-terminally truncated protein of 433 amino acids, with loss of regions critical for normal function. The 1-base-pair insertion and 2-base-pair deletion seen in two other patients are predicted to result in truncated proteins of 234 and 349 amino acids, respectively. Although deletion of the wild-type allele was only seen in one of 11 polyps, some of these may have been contaminated with normal cells during microdissection. Alternatively, other somatic SMAD4 mutations may have been present in these samples, or germline mutation of SMAD4 may induce tumors through a dominant negative effect.

One of the interesting features of the GI polyps seen in compound APC/SMAD4 inmutant heterozygote mice is the increased proliferation of stromal cells (Takaku et al, 1998), which is one of the characteristic features of juvenile polyps seen in humans. It has also been shown in Xenopus embryos that wild-type SMAD4 induces mesodermal markers, and that mixtures of mutant and wild-type SMAD4 inhibit this-response (Lagna et al., 1996). In JP patients, it would appear that germline SMAD4 mutations predispose to focal abnormalities of mesenchymal development (hamartomas) and cancer through disruption of the TGF-β signaling pathway. JP may be a genetically heterogeneous condition, as evidenced by the fact that not all families are linked to 18q markers and not all families studied had germline SMAD4 mutations. It is possible that germline mutations in genes encoding different components of the TGF-β signaling pathway may be present in these other JP kindreds. The roles of the CD gene (PTEN) and Peutz-Jeghers syndrome gene (LKBI (Hemminki et al, 1998)) in cell growth control remain unclear, although PTEN may be down-regulated by TGF-β (Li and Sun, 1997). Further studies on components of the TGF-β pathway may add to our understanding of these hamartomatous polyposis syndromes.

Example 5

Studies in Sporadic Colorectal Tumors

Family members with JP are at significant risk for colorectal cancer and other GI tumors, and since the DPC4 gene maps to the same region commonly deleted in sporadic GI tumors, it is therefore likely that the same gene may play a role in the development of these familial and sporadic tumors. As DPC4 is a known tumor suppressor gene, and it likely plays a role in the genesis of sporadic colorectal cancers, there are three different patterns expected in these tumors. First, GI tumors will likely have homozygous deletions of the gene. Second, there is likely to be deletion of one copy of the gene and mutation of the other copy of the gene and thirdly there will be tumors with mutations in both copies of the gene. The present Example provides details for the investigation of the role of DPC4 in the development of sporadic colorectal cancer.

DNA will be extracted from colorectal tumors and from corresponding normal DNA (blood or adjacent normal colon cells) from patients as described above. If sporadic tumors commonly have large deletions involving both copies of the DPC4 gene, then it will be difficult to prove that the tumors result from this loss. However, suspicions that such a gene is involved could be further studied by transfecting a colorectal cancer cell line with homozygous deletions with an expression vector containing the wild-type gene and looking for loss of tumorigenicity. This could involve reduced growth characteristics in cell culture monolayers, soft agar or reduced malignant potential when tumors are implanted into nude mice. The finding of deletion of one copy of the gene with mutation of the other will provide more direct evidence that the DPC4 gene is involved in the development of sporadic tumors.

If mutations of the DPC4 gene are frequently observed in sporadic colorectal tumors, then statistical analysis of the impact of DPC4 mutations upon various clinicopathologic factors, including tumor location, pathologic stage, presence of vascular or lymphatic invasion, nodal metastases, distant metastases, and patient survival will be performed in order to evaluate prognostic significance (Howe et al., 1997). If these mutations are of prognostic siginificance then this analysis could become a standard pathologic procedure for these specimens, and the potential basis of new screening methods for colorectal tumors.

Having identified the gene for JP as DPC4, it will now be possible to study new families by linkage or by mutational analysis for the 18q21 gene to determine whether this is the predisposing gene in each family. Finding the gene should facilitate the correlation between genotype and phenotype in JP families and the development of an improved classification scheme for the hamartomatous polyposis syndromes. Finally, identification of this gene now allows investigators to progress from linkage-based presymptomatic testing of at-risk family members to direct screening for gene mutations.

Example 6

Loss of SMAD4/DPC4 Protein During Colorectal Tumor Progression

Methods

Sixty unselected archival sporadic colorectal carcinoma specimens were picked from the files of the Department of Pathology, Haartman Institute, University of Helsinki. The tissue samples had been fixed in 10% neutral buffered formalin, and parffin-embedded. Thirty-two blocks representing tumors which were known to be MSI were a derived from the Department of Pathology, as well as from other hospitals around Finland. Al tumors were evaluated and graded by two pathologists. All samples consisted of non-neoplastic (normal and/or hyperplastic) colonic mucosa and adjacent carcinoma tissue. In 27 unselected cases and 9 MSI cases dysplastic/adenomatous areas were also present. Some of these lesions were polyp-like, others consisted merely of few dysplastic crypts.

Immunohistochemical staining to detect Smad4

The presence of Smad4 protein was analyzed from 92 paraffin embedded colorectal carcinoma specimens utilizing a Smad4 polyclonal antibody, raised against a peptide corresponding to amino acids at the carboxyterminal end of the Smad4 protein (Smad4 (C-20); cat.sc-1909, Santa Cruz Biotechnology Inc., U.S.). After deparaffinization, the sections were microwave pretreated. Avidin-biotin complex immunoperoxidase technique was performed by using Elite ABC kit (Vectastain, Vector Laboratories, Burlingame, U.S.). The immunostaining results were analyzed by two pathologists. The percentage of positive cells was evaluated, and scored as follows: <5%, +5% to 9%, ++10% to 24%, +++25% or more.

Deletion Analysis

Deletion analysis was performed to evaluate the Smad4-DCC region deletion status in replication error positive as well as unselected colon cancers. The genomic fragments tested were Smad4 exon 7, DCC exon E and Nebulin exon 168. DCC is reported to be deleted in approximately 50% of all colorectal cancers and it is located close to Smad4 in chromosome 18q21. Nebulin gene (GenBank accession X83957) is located in chromosome 2q and was chosen as a reference gene to confirm the PCR™ amplification strength because this region is usually not deleted in colorectal cancer. The three fragments representing the three genes were amplified in one reaction utilizing fluorescent-labeled primers. Primers for Smad4 amplification were as indicated below (Smad4 exon 7, primers 7F and 7R) and primers for DCC exon E (GenBank accession M63718) and Nebulin exon 168 (GenBank accession AF117665) were:

DCC F: 5'-TCTCCTTAGCAATCCCAAGC (SEQ ID NO:5)

DCC R: 5'-CCTGTTGTCACCTTCTCTGGA (SEQ ID NO:6)

Nebulin F: 5'-TTTTCTTCCTGAGATGGAGAGA (SEQ ID NO:7)

Nebulin R: 5'AAGAAAAGACCAAGTGGGCA (SEQ ID NO:8)

The PCR™-reactions were carried out in 25 µl reaction volume including 100 ng genomic DNA, 1×PCR™ reaction buffer (Perkin Elmer Applied Biosystems Division, Foster City, Calif., USA), 200 µM of each dNTP (Finnzymes, Espoo, Finland), 0.8 µM of each primer and 2 units of AmpliTaqGOLD polymerase (Perkin Elmer Applied Biosystems Division, Foster City Calif., USA). The MgCl$_2$ concentration was 2.5 mM in all reactions. The following PCR™ cycles were used for amplification: 10 min at 95° C., 28 cycles of 30 sec at 95° C., 45 sec at 57° C., 1 min at 72° C. Final extension was 20 min at 72° C.

1.2 µl of PCR™ product were added to 3 µl formamide and 0.5 µl TAMRA 500 size standard (PE/ABI), loaded on a 60% polyacrylamide 8-M urea gel and run in a ABI PRISM™ 377DNA Sequencer (PE/ABI) according to the manufacturer's instructions. The data were collected automatically and analyzed by the GeneScan 3.1 software. The peak area of each fragment (one representing Nebulin, one DCC, and one DPC4) was calculated by Genotyper 2.0 software and the values derived from normal and tumor DNA were compared with each other.

TGFβIIR Mutation Analysis

The polyA tract in the coding region of the TGF-B type II receptor gene was scrutinized for deletions by PCR™ amplification utilizing fluorescent-labeled primers and subsequent fragment analysis by an automated sequencer. The PCR™ reactions were carried out in 10 µl reaction volume including 100 ng genomic DNA, 1×PCR™ reaction buffer (Perkin Elmer Applied Biosystems Division, Foster City, Calif., USA), 200 µM of each dNTP (Finnzymes), 0.3 µM of each primer, and 1.5 units of AmplitaqGOLD polymerase (Perkin Elmer Applied Biosystems Division, Foster City, Calif., USA). The MgCl$_2$ concentration was 1.5 mM. The following PCR™ cycles were used for amplification: 10 min at 94° C., 28 cycles of 30 sec at 94° C., 75 sec at 55 30 sec at 72° C. Final extension was 10 min at 72° C. The forward (F) and reverse R primers were:

F: CTT TAT TCT GGA AGA TGC TG (SEQ ID NO:9)

R: GAA GAA AGT CTC ACC AGG C (SEQ ID NO:10)

Mutation Analysis for Smad4

Smad4 exons were amplified from genomic DNA by using previously published primers except primers for exons 4, 7 and 8 which were designed using the Primer3 server. The forward (F) and reverse (R) primers for exons 4, 7 and 8 were (each primer 5' to 3').

4F: TCAAGTATGATGGTGAAGGATGA (SEQ ID NO:11)

4R: ACTTACTTGGAGTTTCCCCCA (SEQ ID NO:12)

7F: TTTACTGAAAGTTTTAGCATTAGACAA (SEQ ID NO:13)

7R: GCCTGTGTTTGTCGTTTCAA (SEQ ID NO: 14)

8F: GGGAGGATGTTCTTTCCCAT (SEQ ID NO: 15)

8R: TCAATGGCTTCTGTCCTCCTGTG (SEQ ID NO:16)

The PCR™-reactions were carried out in 50 µl reaction volume including 100 ng genomic DNA, 1×PCR™ reaction buffer (Perkin Elmer Applied Biosystems Division, Foster City, Calif., USA), 200 µM of each dNTP (Finnzymes, Espoo, Finland), 0.8 µM of each primer and 2 units of AmpliTaqGOLD polymerase (Perkin Elmer Applied Biosystems Division, Foster City, Calif., USA). The MgCl$_2$ concentration was 1.5 mM in all reactions. The following PCR™ cycles were used for amplification: exons 1, 2, 11—10 min at 95° C., 40 cycles of 45 sec at 95° C., 45 sec at 57° C., 1 min at 72° C.; for exons 3 and 5/6 (one fragment)—10 min at 95° C., 40 cycles of 45 sec at 95° C. 45 sec at 58min at 72° C.; for exons 4, 7, 8, 9 and 10—10 min at 95° C., 40 cycles of 45 sec at 95° C., 45 sec at 56° C., 1 min at 72° C. Final extension 10 min at 72° C. was used for all exons. After PCR™, 5 of PCR™ product was run in 3% agarose (NuSieve, FMC Bioproducts, Rockland, Me., USA) gel to verify the specificity of the PCR™ reaction. The remaining PCR™-product was purified using QIAquick PCR™ purification Kit (QIAGEN). Direct sequencing of PCR™ products was performed using the ABI PRISM Dye Terminator or ABI PRISM dRhodamine cycle sequencing kits (Perkin Elmer Applied Biosystems Division, Foster City, Calif., USA). Cycle sequencing products were electrophoresed on 6% Long Ranger gels (FMC Bioproducts, Rockland, Me.) and analvzed on an Applied Biosystems model 373A or 377 DNA sequencer (Perkin Elmer Applied Biosystems Division, Foster City, Calif., USA).

Statistical Analyses

The independence of staining intensity on histologic classification of tissue samples was tested using Chi-square test with conventional R×C contingency tables. Due to small expected numbers the classes of highest staining intensities of 2+ to 3+ were combined as were also the classes of grading for colon carcinomas. All tests represent two-sided p-values.

Results and Discussion

The inventors performed Smad4 immunostaining on sixty randomly chosen archival colorectal cancer samples utilizing an antibody recognizing the carboxy terminal end of the protein (Table 8A). The only criteria for sample selection was the presence of nonneoplastic (normal and/or hyperplastic) mucosa in the sections, to serve as a positive control in Smad4 immunostaining. Of the 60 tissue blocks 59, 44 and 27 contained areas of normal tissue, hyperplastic tissue, and dysplastic/adenomatous tissue, respectively, in addition to the carcinomatous part. Normal colonic or hyperplastic inucosa displayed in all but two cases positive staining. The staining often appeared to be stronger in hyperplastic mucosal crypts adjacent to carcinomatous areas, than in normal mucosa. Positive staining was observed in 14 out of 27 (52%) dysplastic/adenomatous lesions, while 13 (48%) displayed no staining. Most colorectal adenocarcinomas, 46 out of 60 (77%) were Smad4 negative. In 14 out of 60 carcinomas (23%) detectable Smad4 expression was observed. These tumors were mostly well differentiated. In some of the grade 11 and III cases positive staining was observed in well differentiated areas but not in moderately or poorly differentiated areas of the same carcinoma, in part explaining positivity observed in carcinomas with general grade of II or III (Table 8A). In ten carcinomas extracellular mucin displayed prominent staining. The study thus demonstrates a highly significant tendency of loss of Smad4 expression during colorectal tumorigenesis (Table 8A).

While these results indicate that Smad4 expression is frequently lost in colorectal tumorigenesis, the study does not exclude the possibility that the loss is unspecific, and due to economic deletions commonly seen in the area were Smad4 resides. To investigate this possibility the inventors examined Smad4 immunostaining in 32 colorectal cancer specimens displaying microsatellite instability (MSI) (also known as mutator or replication error phenotype tumors). Unlike most colorectal cancers, these tumors are typically diploid, and rarely display gross chromosomal rearrangements, such as deletions. This series of tumors confirms the results obtained from the first carcinoma set; 29 of the 32 cancers (91%) had lost Smad4 expression, while three (9%) displayed some positive staining. However, only one out of nine dysplastic tumor areas was negative for Smad4. As one of the unselected samples with dysplastic area was a known MSI case displaying Smad4 immunostaining, altogether 9 out of ten MSI dysplastic areas were positive for Smad4 staining, suggesting a difference between MSI and microsatellite stabile (MSS) early tumorogenesis regarding Smad4 loss (p=0.05, Fisher's exact test). Normal tissue in all 32 lesions displayed Smad4 staining (Table 8B).

Though MSI tumors typically do not display large deletions, a possibility remained that 18q21 would be a hotspot for such defects in this tumor type. To exclude this possibility the frequencies of Smad4 (exon 7) and DCC (exon E) deletions in a series o f45 MSI tumors were evaluated. This series of samples included DNA from 23 of the 32 tumors utilized in immunostaining. Nebulin gene exon 168 in chromosome 2q was utilized as a reference fragment for PCR amplification strength. Six out of 45 (13%) MSI cancers displayed deletions of the Smad4-DCC region demonstrating that the region is not commonly deleted in these tumors. One of the deletions affected DCC only. The power of the present approach to detect the Smad4-DCC region deletions in a series of 95 microsatellite stabile (MSS) colorectal cancer samples was confirmed, including 30 that were analyzed for immunostaining. The typical pattern that was observed was one displaying loss of both DCC and Smad4 material (41 out of 95, 43%). 44 samples displayed no loss, and 8 and 2 samples displayed Smad4 and DCC losses only, respectively. As expected, the frequency of Smad4 deletions in MSI samples (5 out of 45, 11%) was highly significantly lower than in MSS samples (49 out of 95, 52%) (p=0.000002. Fisher's exact test). As almost all MSI samples were negative for Smad4 immunostaining, the inactivation of Smad4 is not merely a consequence of 18q deletions.

MSI tumors frequently display inactivating mutation of the TGFβ type II receptor (TGFβIIR) gene; especially deletions in a poly A tract in the coding region of the TGFβIIR. In agreement with previous observations, 28 out of 31 tumors (one tumor DNA failed in PCR) in the present series displayed a protein truncating mutation in the TGFβIIR poly A tract. This is of interest, as both Smad4 and TGFβIIR have been thought to contribute their tumor suppressive effects as members of the TGFβ signalling pathway (Heldin et al., 1997; Whitman, 1998). However, Smad4 mediates also signals from the BMP and activin pathways, that do not require TGFβIIR (Heldin et al., 1997; Whitman, 1998; Zhou et al., 1998) and a recent report has connected TGFβIIR directly to signalling through cyclin B (Liu et al., 1999). The present data suggest that growth control pathways other than TGFβ are highly relevant in colorectal tumorogenesis promoted by loss of TGFβIIR and/or Simad4. The difference of the effects of TGFβIIR and Smad4 mutations can be seen in the cancer phenotype associated with the respective germline mutations. Smad4 mutations predispose to juvenile hamartornatous polyposis (Howe et al., 1998), while a germline TGFβIIR defect appears to be associated with hereditary nonpolyposis colorectal cancer of late onset (Lu et al., 1998). The inventors' observation that both Smad4 and TGFβIIR are inactivated in most MSI colon cancers emphasizes the importance of a network-like structure of signalling through these molecules. The findings reported in this work are in good agreement with a recent study showing the TAFT pathway is inactivated in 70% of MSS tumors. Interestingly, the same study also reports one tumor cell line with inactivating mutations in TGFβIIR as well as Smad4 (Grady et al., 1999), a finding compatible with the present MSI tumor data. Smad4 mutation status was evaluated by genomic sequencing in a pilot series of seven MSI tumors. As no defects were found, somatic Smad4 mutations appear to be uncommon in this tumor type. The immunostaining results indicate that Smad4 expression is frequently lost during colorectal tumorigenesis, regardless of the type of genomic instability driving the neoplastic process. While genomic deletions and somatic mutations explain in good part the loss of Smad4 in MSS colon cancers, the mechanism of Smad4 loss remains obscure in cases with the MSI phenotype. Possible mechanisms include promotor area mutations, and epigenetic changes such as hypermethylation which appears to play a major role in MLH1 inactivation (Dietmaier et al., 1997; Kane et al., 1997; Thihodeau et al., 1998; Herman et al., 1998; Cunningham et al., 1998). Down-regulated expression through transcription factors secondary to genetic events elsewhere, similar to recent findings of the background of c-MYC overexpression in colorectal cancer due to APC mutations (He et al., 1998), is also an option.

TABLE 8A

Smad4 immunostaining results utilizing 60 primary colorectal carcinoma paraffin embedded tissue blocks.

| Smad4 staining | Normal tissue | Hyperplasia | Dyplasia | Colorectal carcinoma, grade | | |
|---|---|---|---|---|---|---|
| | | | | I | II | III |
| − | 2 (3%) | 0 (0%) | 13 (48%) | 7 (50%) | 33 (85%) | 6 (86%) |
| + | 16 (27%) | 8 (18%) | 5 (19%) | 6 (43%) | 5 (13%) | 1 (14%) |
| ++ | 35 (59%) | 25 (57%) | 7 (26%) | 1 (7%) | 0 (0%) | 0 (0%) |
| +++ | 6 (10%) | 11 (25%) | 2 (7%) | 0 (0%) | 1 (3%) | 0 (0%) |
| Number | 59 | 44 | 27 | 14 | 39 | 7 |

Of the 60 specimen blocks 59, 44 and 27 cases contained areas of normal tissue, hyperplastic tissue, and dysplastic tissue, respectively, in addition to the carcinomatous part. There was no significant difference between the staining of normal and hyperplastic tissue samples ($p=0.24$), while both deviated significantly from dysplastic and carcinomatous tissue sample staining ($p<0.0001$ for each comparison). Furthermore, the staining of dysplastic and carcinomatous tissue samples also deviated significantly ($p=0.0004$). The results show highly significant loss of Smad4 immunostaining during tumor progression (C, contingency coefficient=0.61).

TABLE 8B

Smad4 immunostaining results utilizing 32 primary MSI (mutator) phenotype colorectal carcinoma paraffin embedded tissue blocks.

| Smad4 staining | Normal tissue | Hyperplasia | Dyplasia | Colorectal carcinoma, grade | | |
|---|---|---|---|---|---|---|
| | | | | I | II | III |
| − | 0 (0%) | 0 (0%) | 1 (11%) | 4 (80%) | 18 (95%) | 7 (88%) |
| + | 14 (44%) | 7 (25%) | 3 (33%) | 1 (20%) | 1 (5%) | 1 (13%) |
| ++ | 15 (47%) | 17 (61%) | 5 (56%) | 0 (0%) | 0 (0%) | 0 (0%) |
| +++ | 3 (9%) | 4 (14%) | 0 (%) | 0 (0%) | 0 (0%) | 0 (0%) |
| Number | 32 | 28 | 9 | 5 | 19 | 8 |

Of the 32 blocks 32, 28 and 9 cases contained areas of normal tissue, hyperplastic tissue, and dysplastic tissue, respectively, in addition to the carcinomatous part. There was no significant difference between the staining of normal and hyperplastic tissue samples ($p=0.13$). while both deviated significantly from carcinomatous tissue sample staining ($p<0.0001$). Furthermore the staining of dysplastic and carcinomatous tissue samples also deviate significantly ($p<0.0001$), though the expected numbers in dysplastic group were too small. Similar to results in the unselected tumor series, these data show highly significant loss of Smad4 immunostaining in colorectal carcinogenesis (C, contingency coefficient=0.68). (N.B. Here again, the expected numbers for dysplastic lesions were too small but their contribution to Chi-value was non-significant)

All of the composition and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

"Manipulating the Mouse Embryo; A Laboratory Manual" 2nd edition eds., Hogan, Beddington, Costantimi and Long, Cold Spring Harbor Laboratory Press, 1994;

"Remington's Pharmaceutical Sciences" 15th Edition, pages 1035–1038 and 1570–1580

Arap et al., Cancer Res., 55:1351–1354, 1995.
Arcone, et al., Nucl. Acids Res., 16(8): 3195–3207, 1988.
Jarvinen and Franssila, Gut 25, 792–800, 1984.
Baichwal and Sugden, In: Gene Transfer, Kucherlapati R, ed., New York, Plenum Press, pp. 17–148,1986.
Baptist and Sabatini, Hum Pathol 16:1061–1063, 1985.
Bartlett et al., Proc. Nat'l Acad. Sci. USA, 93:8852–8857, 1996.
Bassam et al., Analytical Biochemistry 196, 80–83, 1991.
Bedzyk et al., J. Biol. Chem., 265:18615, 1990
Bellus, J. Macromol. Sci. Pure Appl. Chem, A311: 1355–1376, 1994.
Bentley et al., Am J Gastroenterol 84:1456–1459, 1989.
Benvenisty and Neshif, Proc. Nat'l Acad. Sci. USA, 83:9551–9555,1986.
Brack-Wemer et al., Genomics 4:68–75, 1989.
Brinster et al., Proc. Nat'l Acad. Sci. USA, 82: 4438–4442, 1985.
Burt et al., Bulletin of the World Health Organization 68, 655–664, 1993.
Bussemakers et al., Cancer Res., 52:2916–2922, 1992.
Caldas et al., Nat'l Genet., 8:27–32, 1994.
Carle and Olson Nucleic Acids Research 12, 5647–5664, 1984.
Carter and Flotte, Ann. N.Y. Acad. Sci., 770:79–90, 1995.
Carter et al., Proc. Nat'l Acad. Sci. USA, 87:8751–8755, 1990.
Chatterjee, et al., Ann. N.Y. Acad. Sci., 770:79–90, 1995.
Chaudhary et al., Proc. Nat'l Acad Sci., 87:9491,1990
Chen and Faller, J. Biol. Chem., 271:2376, 1996.
Chen and Okayama, Mol. Cell Biol., 7:2745–2752, 1987.
Cheng et al., Cancer Res., 54:5547–5551, 1994.
Cheng et al., Nature, 379:554, 1996.
Cho et al., Genomics 19:525–531, 1994
Coffin, In. Virology, ed., New York: Raven Press, pp. 1437–1500, 1990.
Cottingham et al., American Journal of Human Genetics 53, 252–263, 1993.
Coupar et al., Gene, 68:1–10, 1988
Culver et al., Science, 256:1550–1552, 1992.
Dani, et al., J. Biol. Chem., 264:10119–10125, 1989.
Davey et al., EPO No. 329 822.
Devereux et al., Carcinogenesis; 18(9): 1751–1755. 1997
Dubensky et al., PROc. Nat'l Acad Sci. USA, 81:7529–7533, 1984.
Edelman and Crossin. Annu. Rev. Biochem., 60:155–190, 1991.
Eng and Ji, Am J Hum Genet 62:1020–1022, 1998.
EPO No. 320.308,
Eppert et al., Cell 86, 543–552, 1996.

Fazeli et al., *Nature* 386, 796–804, 1997.
Fearon and Vogelstein, *Cell*, 61:759–767, 1990.
Fearon et al., *Science* 247, 49–247, 1990.
Fechheimer et at., *PROc. Nat'l Acad Sci. USA*, 84:8463–8467,1987.
Feinberg and Vogelstein, *Analytical Biochemistry* 137, 266–267, 1984.
Ferkol et al., *FASEB J.*, 7:1081–1091,1993.
Ferrari et al., *J. Virol.*, 70:3227–3234, 1996.
Fisher et al., *J. Virol.*, 70:520–532, 1996.
Flotte et al., *PROC: Nat'l Acad Sci. USA*, 90:10613–10617, 1993.
Fodor et al., *SCIENce*, 251:767–773, 1991.
Fraley et al., *PROC. Nat'l Acad. Sci. USA*, 76:3348–3352, 1979.
Freifelder, *Physical Biochemistry Applications to Biochemistry and Molecular Biology*, 2nd ed. Wm. Freeman and Co., New York, N.Y., 1982.
Frixen etal., *J. Cell Biol.*, 113:173–185, 1991.
Frohman, In: *PCR Protocols. A Guide To Methods And Applications*, Academic Press, N.Y., 1990.
GB Application 2 202 328
Ghosh-Choudhury et al., *EMBO J.*, 6:1733–1739, 1987.
Ghosh and Bachhawat, In: *Liver Diseases, Targeted Diagnosis and Therapy Using Specific Receptors and Ligands*. Wu et al., eds., Marcel Dekker, New York, pp. 87–104, 1991.
Gingeras et al., PCT Application WO 88/10315,
Goodman et al., *Blood*, 84:1492–1500, 1994.
Goodman et al., *Cancer* 43, 1906–1913, 1979.
Gopal., *Mol. Cell Biol.*, 5:1188–1190,1985.
Gossen and Bujard, *Proc. Nat'l Acad. Sci. USA*, 89:5547–5551, 1992.
Gossen et al., *Science*, 268:1766–1769. 1995.
Grady et al., *Cancer Res.*, 59, 320–324, 1999.
Graham and Prevec, In: *Methods in Molecular Biology. Gene Transfer and Expression Protocol*, E. J. Murray, ed., Hurnana Press, Clifton, N.J., 7:109–128, 1991.
Graham and van der Eb, *Virology*, 52:456–467,1973.
Grau et al., *Cancer Res.*, 57:3929, 1997.
Grotsky et al., *Gastroenterology* 82:494–501, 1982.
Hacia et al., *Nature Genetics*, 14:441–447, 1996.
Hahn et al., *Cancer Res*; 58(6):1124–1126 1998
Hahn et al., *Cancer Research* 56, 490–494, 1996b.
Hahn et al., *Science* 271, 350–353, 1996a.
Harland and Weintraub, *J. Cell Biol.*, 101: 1094–1099,1985.
Hay etal., *J. Mol. Biol.*, 175:493–510, 1984.
Hearing and Shenk, *J. Mol. Biol.* 67:809–822, 1983.
Hearing et al., *J. Virol.*, 67:2555–2558, 1987.
Heldin et al., *Nature*, 390, 465471, 1997.
Hemnmninki et al., *Nat Genet* 15:87–90, 1997.
Hemminki et al., *Nature* 391:184–187, 1998.
Hollstein et al., *Science*, 253:49–53, 1991.
Howe and Conlon, *Surgical Oncology* 6, 1–18, 1997.
Howe and Guillem, *Surgical Clinics of North America* 77, 175–195, 1997.
Howe et al., *American Journal of Human Genetics* 51, 1430–1442, 1992a.
Howe et al., *Annals of Surgery (in press)*, 1998.
Howe et al., *Clinical Cancer Research* 3, 129–133, 1997.
Howe et al., *Histology and Histopathology* 12, 595–601, 1997.
Howe et al., *Human Genetics* 91, 199–204, 1993.
Howe et al., *Nucleic Acids Research* 19, 2518, 1991.
Howe et al., *Nucleic Acids Research* 20, 1168, 1992.
Howe et al., *Science* 280, 1086–1088, 1998.
Howe et al., *Surgery* 112, 219–226, 1992b.
Howe et al., *Surgical Forum* 41, 447–450, 1990.
Howe et al., *Am. J. Hum. Genet.* (in press).
Howe et al., *Histol. Histopathol.* 12:595, 1997
Hudson et al., *Science* 270, 1945–1954, 1995.
Hunt et al., *Proc. Nat'l Acad. Sci. USA*, 83:3786–3790. 1986.
Hursh, et al., *Development*, 117:1211, 1993
Hussussian et al., *Nature Genetics*, 5–21, 1994.
Innis et al., *PCR Protocols*, Academic Press, Inc. San Diego Calif., 1990.
Jacoby et al., *American Journal of Human Genetics* 70, 361–364, 1997a.
Jacoby et al., *Gastroenterology* 112, 1398–1403, 1997b.
Jarvinen, *Problems in General Surgery* 10, 749–757, 1993.
Jass et al., *Histopathology* 13:619–630, 1988.
Jass, In: Utsunomiya J. Lynch HT (eds) "Hereditary colorectal cancer." Springer, Tokyo, pp 343–350, 1990.
Jenne et al., *Nature Genetics* 18, 38–43, 1998.
Joki et al., *Human Gene Ther.*, 6:1507–1513, 1995.
Jones et al., *Arch Pathol Lab Med* 111:200–201, 1987.
Kageyama et al., *J. Biol. Chem.*, 262(5).2345–2351, 1987.
Kamb et al., *Nature Genetics*, 8:22–26, 1994.
Kamb et al. *Science*, 264:436–440, 1984.
Kaneda et al., *Science*, 243:375–378,1989.
Kaplitt et al., *Arm. Thor. Surg.*, 62:1669–1676, 1996.
Kaplitt et al., *Nat'l Genet.*, 8:148–153, 1994.
Kato et al., *J. Biol. Chem.*, 266:3361–3364, 1991.
Keino-Masu et al., *Cell* 87, 175–185, 1996.
Kessler et al., *Proc. Nat'l Acad Sci. USA*, 93: 14082–14087, 1996.
Kim et al., *Cancer Res.*, 56:2519, 1996.
Klein et al., *Nature*, 327:70–73,1987.
Knudson, et al., *Proc. Nat'Acad Sci. USA.* 72, 5116–5120, 1975.
Knudsonn et al., *Science*, 270:96, 1995.
Koeberl et al., *Proc. Nat'l Acad Sci. USA*, 94:1426–1431, 1997.
Korhonen, et al., *Blood*, 86(5):1828–1835, 1995.
Kwoh et al., *Proc. Nat'l Acad. Sci. USA*, 86: 1173, 1989.
Lagna et al., *Nature*, 383:832, 1996.
Landis et al., *CA-A Cancer Journal for Clinicians* 48, 6–30, 1998.
Lathrop et al., *Am J. Hum Genet* 37:482–498, 1985.
Lathrop, et al., *Proc. Nat'l Acad Sci. USA*, 81:3443–3446, 1984.
Leggett et al., *Gastroenterology* 105, 1313–1316, 1993.
Levrero et al., *Gene*, 101 195–202, 1991.
Li and Sun, *Cancer Res.*, 57:2124–2129, 1997.
Liaw et al., *Nat Genet* 16:64–67, 1997.
Liu et al., *Chin Med J* (Engl) 4:434–439, 1978.
Lynch et al., *Cancer* 56, 939–951, 1985.
Lynch, *Am J Hum Genet* 61:1254–1260, 1997.
Macejak and Samow, *Nature*, 353:90–94, 1991.
MacGorgan et al., *Oncogene*; 15(9): 1111–1114, 1997
Mann et al., *Cell*, 33:153–159,1983.
Marsh et al., *Cancer Research* 57, 5017–5021, 1997.
Marsh et al., *Nature Genet.*, 16:333, 1997.
Matsura et al., *Brit. J. Cancer*, 66:1122–1130, 1992
McCown et al., *Brain Res.*, 713:99–107, 1996.
Mehenni et al., *Am Hum Genet* 61: 1327–1334, 1997.
Miller et al., *Nucleic Acids Research* 16, 1215, 1988.
Miller et al., PCI Application WO 89/06700
Mizukami et al., *Virology*, 217:124–130, 1996.
Mori et al., *Cancer Res.*, 54:3396–3397,1994.
Morson, *Dis Colon Rectum* 5:337–344 1962.
Moskaluk et al., *Diagnostic Molecular Pathology* 6, 85–90, 1997.

Myers, EPO 0273085
Nakamura et al. In: Handbook of Experimental Immunology (4th Ed.), Weir. E., Herzenberg, L. A. Blackwell, C., Herzenberg, L. (eds). Vol. 1. Chapter 27, Blackwell Scientific Publ., Oxford, 1987.
Nelen et al., *Nature Genetics* 13, 114–116, 1996.
Newton et al., *Statistical Medicine* 13, 839–858, 1994.
Nichols et al., *Computer Applications in the Biosciences* 9, 757–759, 1993.
Nicolas and Rubenstein, In. *Vectors. A survey of molecular cloning vectors and their uses*, Rodriguez and Denhardt (eds.), Stoneham: Butterworth, pp. 493–513. 1988.
Nicolau and Sene, *Biochim. Biophys. Acta*, 721:185–190, 1982.
Nicolau et al., Method Enzymol., 149:157–176, 1987.
Nishizuka et al., *Jpn J Cancer Res*; 88(4): 335–339, 1997
Nobori et al., *Nature*, 368:753–756, 1995.
Ohara et al., *Proc. Nat'l Acad. Sci. USA*, 86: 5673–5677, 1989.
Okamoto et al., *Proc. Nat'l Acad Sci. USA*, 91:11045–11049, 1994.
Olivierio et al., *EMBO J.*, 6(7):1905–1912, 1987.
Olschwang et al., *Nat Genet* 18:12–14, 1998.
Orlow et al., *Cancer Res.*, 54:2848–2851, 1994.
Pape and Kim, *Mol. Cell. Biol.*, 974–982, 1989.
Paskind et al., *Virology*, 67:242–248,1975.
PCT/US87/00880
PCT/US89/01025
Pease et al., *Proc. Nat'l Acad Sci. USA*, 91 :5022–5026, 1994.
Pelletier and Sonenberg, *Nature*, 334:320–325, 1988.
Perales et al., *Proc. Nat'l Acad Sci.* 91:4086–4090,1994.
Pignon et al., *Hum. Mutat.*, 3:126–132, 1994.
ing et al., *Microcirculation*, 3:225–228, 1996.
Poli and Cortese, *Proc. Nat'l Acad. Sci. USA*, 86:8202–8206, 1989.
Potter et al., *Proc. Nat'l Acad. Sci. USA*, 81:7161–7165, 1984.
Prowse and Baumann, *Mol Cell Biol*, 8(1):42–51,1988.
Radler et al., *Science*, 275:810–814, 1997.
Ramaswamy et al., *Diseases of the Colon and Rectum* 27, 393–398, 1984.
Reiss et al., *Cell Growth Differ*; 8(4): 407–415. 1997.
Remington's Pharmaceutical Sciences, 15th ed., pp. 1035–1038 and 1570–1580.
Renan, Radiother. *Oncol.*, 19:197–218, 1990.
Ridgeway, In. *Vectors: A survey of molecular cloning vectors and their uses*, Rodriguez R L, Denhardt D T, ed., Stoneham: Butterworth, pp. 467–492,1988.
Riggins et al., "Normal PTEN gene in juvenile polyposis." *NOGO* 1:1 (http://pathologyjhu.edu/nogo/), 1997.
Rippe et al., *Mol. Cell Biol.*, 10:689–695, 1990.
Risinger and Boyd, *Hum Mol Genet* 1:657, 1992.
Ron, et al., *Mol. Cell. Biol.*, 2887–2895, 1991.
Roux et al., *Proc. Nat'l Acad Sci. USA*, 86:9079–9083,1989.
Rozen and Baratz, *Cancer* 49:1500–1503, 1982.
Rustgi, *New England Journal of Medicine* 331, 1694–1702, 1994.
Sachatello et al., *Gastroenterology* 58:699–708, 1970.
Sambrook et al., In: *Molecular Cloning. A Laboratory Manual.*, 2d Ed., Cold Spring Harbor Laboratory Press, Cold Spring Harbor, N.Y., 1989.
Samulski et al., *EMBO J.*, 10:3941–3950, 1991.
Samulski et al., *J. Virol.*, 61(10):3096–3101, 1987.
Schutte et al., *Cancer Res.*, 56:2527, 1996.
Scott-Conner et al., *Journal of the American College of Surgeons* 181, 407–413, 1995.
Sekelsky, et al., *Genetics*, 139:1347, 1995.
Shi et al., *Nature*, 388:87, 1997.
Shoemaker et al., *Nature Genetics* 14:450–456, 1996.
Silverman et al., *Cytogenetics and Cell Genetics* 75, 111–131, 1996.
Speigelman, et al.,*J. Biol. Chem.*, 264(3), 1811–1815, 1989.
Stemper et al., *Ann Intern Med* 83:639–646, 1975.
Takagi et al., *Gastroenterology*, 111:1369, 1996.
Takaku et al., *Cell*, 92:645, 1998.
Temin, In: *Gene Transfer*, Kucherlapati (ed.), New York: Plenum Press, pp. 149–188, 1986.
Thiagalingam et al., *Nature Genetics* 13, 343–346, 1996.
Thomas et al., *Am J Hum Genet* 58:770–776, 1996.
Tibbetts *Cell*, 12:243–249, 1977.
Tur-Kaspa et al., *Mol. Cell Biol.*, 6:716–718,1986.
U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,340,535,
U.S. Pat. No. 4,366,241,
U.S. Pat. No. 4,683,195
U.S. Pat. No. 4,683,202
U.S. Pat. No. 4,786,600,
U.S. Pat. No. 4,800,159,
U.S. Pat. No. 4,873,191;
U.S. Pat. No. 4,883,750
U.S. Pat. No. 4,988,617,
U.S. Pat. No. 5,712,097
U.S. Pat. No. 5,712,097
U.S. Pat. No. 5,712,097,
U.S. Pat. No. 5,190,856
U.S. Pat. No. 5,270,184
U.S. Pat. No. 5,279,721,
U.S. Pat. No. 5,324,631
U.S. Pat. No. 5,359,046,
U.S. Pat. No. 5,484,699,
U.S. Pat. No. 5,494,810,
U.S. Pat. No. 5,496,699,
U.S. Pat. No. 5,633,365
U.S. Pat. No. 5,639,611
U.S. Pat. No. 5,665,549,
U.S. Pat. No. 5,712,124
U.S. Pat. No. 5,733,733;
U.S. Pat. No. 5,733,752;
U.S. Pat. No. 5,744,311;
U.S. Pat. No. 5,747,255
U.S. Pat. No. 5,747,469,
Umbas et al., 1992
Umbas et al., *Cancer Res.*, 52:5104–5109, 1992.
Veale et al., *J Med Genet* 3:5–16, 1966.
Vogelstein et al., *New England Journal of Medicine* 319, 525–532, 1988.
Vogelstein, et al., *Genes Chromosomes Cancer*, 2:2, 159–162, 1990.
Wagner et al., *Proc. Nat'l Acad Sci.* 87, 9:3410–3414, 1990.
Wagner et al., *Science*, 260:1510–1513,1993.
Walker et al., *Proc. Nat'l Acad Sci. USA*, 89:392–396 1992.
Walpole et al., *Am J W4ed Genet* 32:1–8, 1989.
Walter et al., *Nature Genetics* 7, 22–28, 1994.
Walther and Stein, *J. Mol. Med.*, 74:379–392, 1996.
Watanabe et al., *Gastroenterology* 77:148–151, 1979.
Watt et al., *Proc. Nat'l Acad Sci.*, 83(2): 3166–3170, 1986.
Whitelaw et al., *Gastroenterology* 112, 327–334, 1997.
Whitman, *Gene Dev.*, 12, 2445–2462, 1998.

Wilson et al., *Mol. Cell. Biol.*, 6181–6191, 1990.
WO 84/03564.
WO 90/07641
Wong et al., *Gene*, 10:87–94, 1980.
Wrana and Attisano, *Trends Genet.*, 12:493, 1996.
Wrana and Pawson, *Nature*, 388:28, 1997.
Wu and Wu, *Adv. Drug Delivery Rev.*, 12:159–167, 1993.

Wu and Wu, *J. Biol. Chem.*, 262:4429–4432, 1987.
Wu and Wu, *Biochem.*, 27:887–892, 1988.
Wu et al., *Genomics*, 4:560, 1989.
Yang et al., *Proc. Nat'l Acad. Sci. USA*, 87:9568–9572, 1990.
Yoshida et al., *Endoscopy* 20, 33–35, 1988.
Zechner et al., *Mol. Cell. Biol.* 2394–2401, 1988.

What is claimed is:

1. A method of diagnosing juvenile polyposis comprising the steps of:
   (i) obtaining a sample from a subject that either (a) has been diagnosed with at least one gastrointestinal polyp or (b) is related to an individual that has been diagnosed with juvenile polyposis (JP) or gastrointestinal (GI) cancer; and
   (ii) determining the loss or mutation of a SMAD4 gene in cells of said sample,
   wherein the loss or mutation of a SMAD4 gene, in combination with at least one gastrointestinal polyp, familial history of JP or GI cancer, or both, is diagnostic of JP.

2. The method of claim 1, wherein said sample is selected from the group consisting of blood, buccal smear, and an amniocentesis sample.

3. The method of claim 1 said sample is a tissue or fluid sample.

4. The method of claim 1, wherein said determining comprises assaying for a SMAD4 nucleic acid from said sample.

5. The method of claim 4, turther comprising subjecting said sample to conditions suitable to amplify said nucleic acid.

6. The method of claim 1, further comprising the step of comparing the expression of SMAD4 in said sample with the expression of SMAD4 in non-JP samples.

7. The method of claim 6, wherein the comparison involves evaluating the level of SMAD4 expression.

8. The method of claim 6, wherein the comparison involves evaluating the structure of the SMAD4 gene, protein or transcript.

9. The method of claim 8, wherein said evaluating is an assay selected from the group consisting of sequencing, wild-type oligonucleotide hybridization, mutant oligonucleotide hybridization, SSCP, PCR, denaturing gradient gel electrophoresis and RNase protection.

10. The method of claim 9, wherein said evaluating is wild-type or mutant oligonucleotide hybridization and said oligonucleotide is configured in an array on a chip or wafer.

11. The method of claim 1, wherein said JP sample comprises a mutation in the coding sequence of SMAD4.

12. The method of claim 11, wherein said mutation produces a deletion mutant, an insertion mutant, a frameshift mutant, a nonsense mutant, a missense mutant or splice mutant.

13. The method of claim 11, wherein said mutation is a frameshift mutation.

14. The method of claim 13, wherein said mutation results in a premature termination of the SMAD4 gene product.

15. The method of claim 13, wherein said mutation is in exon 9.

16. The method of claim 13, wherein said frarneshift results from a deletion in codons 414 through to 416.

17. The method of claim 16, wherein said frameshift results in a STOP at codon 434 of wild-type SMAD4.

18. The method of claim 13, wherein said mutation is in exon 8.

19. The method of claim 13, wherein said mutation is a deletion in codon 348.

20. The method of claim 19, wherein said mutation results in a frameshift and a new STOP at codon 350 of wild-type SMAD4.

21. The method of claim 18, wherein said mutation is a deletion in codon 345.

22. The method of claim 21, wherein said mutation results in a frameshift and a new STOP at codon 382 to 383 of wild-type SMAD4.

23. The method of claim 17, wherein said mutation is in exon 5.

24. The method of claim 23, wherein said frameshift resulits from an insertion in codon 229 through to 231.

25. The method of claim 24, wherein said frameshift results in a STOP at codon 235 of wild-type SMAD4.

26. The method of claim 12, wherein said mutation is a missense mutation.

27. The method of claim 26, wherein said missense mutation is an A to C substitution at codon 352, converting a tyrosine to a serine.

28. The method of claim 12, wherein said mutation is a nonsense mutation.

29. The method of claim 28, wherein nonsense mutation wherein said nonsense mutation is a G to C substitution at codon 177, converting a serine to a stop codon.

30. The method of claim 1, wherein the subject has been diagnosed with a gastrointestinal polyp and is related to an individual that has been diagnosed with JP or GI cancer.

* * * * *

UNITED STATES PATENT AND TRADEMARK OFFICE
CERTIFICATE OF CORRECTION

PATENT NO.   : 6,423,491 B1
DATED        : July 23, 2002
INVENTOR(S)  : Howe et al.

It is certified that error appears in the above-identified patent and that said Letters Patent is hereby corrected as shown below:

Column 84,
Line 17, please delete "frarneshift" and insert -- frameshift -- therefor.
Line 34, please delete "17" and insert -- 13 -- therefor.
Line 37, please delete "resulits" and insert -- results -- therefor.
Line 48, please delete "wherein nonsense mutation wherein said nonsense mutation" and insert -- wherein said nonsense mutation -- therefor.

Signed and Sealed this

Fifth Day of November, 2002

Attest:

JAMES E. ROGAN
Attesting Officer     Director of the United States Patent and Trademark Office

SEQUENCE LISTING

<160> NUMBER OF SEQ ID NOS: 16

<210> SEQ ID NO 1
<211> LENGTH: 20
<212> TYPE: DNA
<213> ORGANISM: Homo sapiens

<400> SEQUENCE: 1
taggcaaagg tgtgcagttg                                           20

<210> SEQ ID NO 2
<211> LENGTH: 23
<212> TYPE: DNA
<213> ORGANISM: Homo sapiens

<400> SEQUENCE: 2
tgcacttggg tagatcttat gaa                                       23

<210> SEQ ID NO 3
<211> LENGTH: 2680
<212> TYPE: DNA
<213> ORGANISM: Homo sapiens

<400> SEQUENCE: 3
ggttatcctg aatacatgtc taacaatttt ccttgcaacg ttagctgttg tttttcactg      60
tttccaaagg atcaaaattg cttcagaaat tggagacata tttgatttaa aaggaaaaac    120
ttgaacaaat ggacaatatg tctattacga atacaccaac aagtaatgat gcctgtctga    180
gcattgtgca tagtttgatg tgccatagac aaggtggaga gagtgaaaca tttgcaaaaa    240
gagcaattga agtttggta aagaagctga aggagaaaaa agatgaattg gattctttaa     300
taacagctat aactacaaat ggagctcatc ctagtaaatg tgttaccata cagagaacat    360
tggatgggag gcttcaggtg gctggtcgga aaggatttcc tcatgtgatc tatgcccgtc    420
tctggaggtg gcctgatctt cacaaaaatg aactaaaaca tgttaaatat tgtcagtatg    480
cgtttgactt aaaatgtgat agtgtctgtg tgaatccata tcactacgaa cgagttgtat    540
cacctggaat tgatctctca ggattaacac tgcagagtaa tgctccatca agtatgatgg    600
tgaaggatga atatgtgcat gactttgagg gacagccatc gttgtccact gaaggacatt    660
caattcaaac catccagcat ccaccaagta atcgtgcatc gacagagaca tacagcaccc    720
cagctctgtt agccccatct gagtctaatg ctaccagcac tgccaacttt cccaacattc    780
ctgtggcttc cacaagtcag cctgccagta tactgggggg cagccatagt gaaggactgt    840
tgcagatagc atcagggcct cagccaggac agcagcagaa tggatttact ggtcagccag    900
ctacttacca tcataacagc actaccacct ggactggaag taggactgca ccatacacac    960
ctaatttgcc tcaccaccaa aacggccatc ttcagccacc cgcctatg ccgccccatc     1020 ccggacatta ctggcctgtt cacaatgagc ttgcattcca gcctccatt tccaatcatc    1080 ctgctcctga gtattggtgt tccattgctt actttgaaat ggatgttcag gtaggagaga    1140

```
catttaaggt tccttcaagc tgccctattg ttactgttga tggatacgtg gacccttctg   1200
gaggagatcg cttttgtttg ggtcaactct ccaatgtcca caggacagaa gccattgaga   1260
gagcaaggtt gcacataggc aaaggtgtgc agttggaatg taaaggtgaa ggtgatgttt   1320
gggtcaggtg ccttagtgac cacgcggtct ttgtacagag ttactactta gacagagaag   1380
ctgggcgtgc acctggagat gctgttcata agatctaccc aagtgcatat ataaaggtct   1440
ttgatttgcg tcagtgtcat cgacagatgc agcagcaggc ggctactgca caagctgcag   1500
cagctgccca ggcagcagcc gtggcaggaa acatccctgg cccaggatca gtaggtggaa   1560
tagctccagc tatcagtctg tcagctgctg ctggaattgg tgttgatgac cttcgtcgct   1620
tatgcatact caggatgagt tttgtgaaag ctggggacc ggattaccca agacagagca    1680
tcaaagaaac accttgctgg attgaaattc acttacaccg ggccctccag ctcctagacg   1740
aagtacttca taccatgccg attgcagacc cacaaccttt agactgaggt ctttaccgt    1800 tggggccctt aaccttatca ggatggtgga ctacaaaata caatcctgtt tataatctga   1860
agatatattt cactttcttt ctgctttatc ttttcataaa gggttgaaaa tgtgtttgct   1920
gccttgctcc tagcagacag aaactggatt aaaacaattt ttttttcctc ttcagaactt   1980
gtcaggcatg gctcagagct tgaagattag gagaaacaca ttcttattaa ttcttcacct   2040
gttatgtatg aaggaatcat tccagtgcta gaaatttag ccctttaaaa cgtcttagag     2100 cctttatct gcagaacatc gatatgtata tcattctaca gaataatcca gtattgctga    2160 ttttaaggc agagaagttc tcaaagttaa ttcacctatg ttatttgtg tacaagttgt      2220 tattgttgaa catacttcaa aaataatgtg ccatgtgggt gagttaattt taccaagagt   2280
aactttactc tgtgtttaaa aatgaagtta ataatgtatt gtaatctttc atccaaaata   2340
ttttttgcaa gttatattag tgaagatggt ttcaattcag attgtcttgc aacttcagtt   2400
ttatttttgc caaggcaaaa aactcttaat ctgtgtgtat attgagaatc ccttaaaatt   2460
accagacaaa aaaatttaaa attacgtttt ttattcctag tggatgactg ttgatgaagt   2520
atacttttcc cctgttaaac agtagttgta ttcttctgta tttctaggca caaggttggt   2580
tgctaagaag cctataagag gaatttcttt tccttcattc atagggaaag gttttgtatt   2640
ttttaaaaca ctaaaagcag cgtcactcta cctaatgtct                         2680
```

<210> SEQ ID NO 4
<211> LENGTH: 552
<212> TYPE: PRT
<213> ORGANISM: Homo sapiens
<220> FEATURE:

<400> SEQUENCE: 4

```
Met Asp Asn Met Ser Ile Thr Asn Thr Pro Thr Ser Asn Asp Ala Cys
 1               5                  10                  15

Leu Ser Ile Val His Ser Leu Met Cys His Arg Gln Gly Gly Glu Ser
            20                  25                  30

Glu Thr Phe Ala Lys Arg Ala Ile Glu Ser Leu Val Lys Lys Leu Lys
        35                  40                  45

Glu Lys Lys Asp Glu Leu Asp Ser Leu Ile Thr Ala Ile Thr Thr Asn
    50                  55                  60

Gly Ala His Pro Ser Lys Cys Val Thr Ile Gln Arg Thr Leu Asp Gly
65                  70                  75                  80

Arg Leu Gln Val Ala Gly Arg Lys Gly Phe Pro His Val Ile Tyr Ala
                85                  90                  95
```

```
Arg Leu Trp Arg Trp Pro Asp Leu His Lys Asn Glu Leu Lys His Val
                100                 105                 110
Lys Tyr Cys Gln Tyr Ala Phe Asp Leu Lys Cys Asp Ser Val Cys Val
            115                 120                 125
Asn Pro Tyr His Tyr Glu Arg Val Val Ser Pro Gly Ile Asp Leu Ser
        130                 135                 140
Gly Leu Thr Leu Gln Ser Asn Ala Pro Ser Ser Met Met Val Lys Asp
145                 150                 155                 160
Glu Tyr Val His Asp Phe Glu Gly Gln Pro Ser Leu Ser Thr Glu Gly
                165                 170                 175
His Ser Ile Gln Thr Ile Gln His Pro Pro Ser Asn Arg Ala Ser Thr
            180                 185                 190
Glu Thr Tyr Ser Thr Pro Ala Leu Leu Ala Pro Ser Glu Ser Asn Ala
        195                 200                 205
Thr Ser Thr Ala Asn Phe Pro Asn Ile Pro Val Ala Ser Thr Ser Gln
    210                 215                 220
Pro Ala Ser Ile Leu Gly Gly Ser His Ser Glu Gly Leu Leu Gln Ile
225                 230                 235                 240
Ala Ser Gly Pro Gln Pro Gly Gln Gln Gln Asn Gly Phe Thr Gly Gln
                245                 250                 255
Pro Ala Thr Tyr His His Asn Ser Thr Thr Thr Trp Thr Gly Ser Arg
            260                 265                 270
Thr Ala Pro Tyr Thr Pro Asn Leu Pro His His Gln Asn Gly His Leu
        275                 280                 285
Gln His His Pro Pro Met Pro Pro His Pro Gly His Tyr Trp Pro Val
    290                 295                 300
His Asn Glu Leu Ala Phe Gln Pro Pro Ile Ser Asn His Pro Ala Pro
305                 310                 315                 320
Glu Tyr Trp Cys Ser Ile Ala Tyr Phe Glu Met Asp Val Gln Val Gly
                325                 330                 335
Glu Thr Phe Lys Val Pro Ser Ser Cys Pro Ile Val Thr Val Asp Gly
            340                 345                 350
Tyr Val Asp Pro Ser Gly Gly Asp Arg Phe Cys Leu Gly Gln Leu Ser
        355                 360                 365
Asn Val His Arg Thr Glu Ala Ile Glu Arg Ala Arg Leu His Ile Gly
    370                 375                 380
Lys Gly Val Gln Leu Glu Cys Lys Gly Glu Gly Asp Val Trp Val Arg
385                 390                 395                 400
Cys Leu Ser Asp His Ala Val Phe Val Gln Ser Tyr Tyr Leu Asp Arg
                405                 410                 415
Glu Ala Gly Arg Ala Pro Gly Asp Ala Val His Lys Ile Tyr Pro Ser
            420                 425                 430
Ala Tyr Ile Lys Val Phe Asp Leu Arg Gln Cys His Arg Gln Met Gln
        435                 440                 445
Gln Gln Ala Ala Thr Ala Gln Ala Ala Ala Gln Ala Ala
    450                 455                 460
Val Ala Gly Asn Ile Pro Gly Pro Gly Ser Val Gly Gly Ile Ala Pro
465                 470                 475                 480
Ala Ile Ser Leu Ser Ala Ala Gly Ile Gly Val Asp Asp Leu Arg
                485                 490                 495
Arg Leu Cys Ile Leu Arg Met Ser Phe Val Lys Gly Trp Gly Pro Asp
            500                 505                 510
```

```
Tyr Pro Arg Gln Ser Ile Lys Glu Thr Pro Cys Trp Ile Glu Ile His
        515                 520                 525

Leu His Arg Ala Leu Gln Leu Leu Asp Glu Val Leu His Thr Met Pro
        530                 535                 540

Ile Ala Asp Pro Gln Pro Leu Asp
545                 550
```

```
<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
tctccttagc aatcccaagc                                                   20

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
cctgttgtca ccttctctgg a                                                 21

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
ttttcttcct gagatggaga ga                                                22

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
aagaaaagac caagtgggca                                                   20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
ctttattctg gaagatgctg                                                   20

<210> SEQ ID NO 10
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      Primer

<400> SEQUENCE: 10
gaagaaagtc tcaccaggc                                                19

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
tcaagtatga tggtgaagga tga                                           23

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
acttacttgg agtttccccc a                                             21

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
tttactgaaa gttttagcat tagacaa                                       27

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
gcctgtgttt gtcgtttcaa                                               20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
gggaggatgt tctttcccat                                               20

<210> SEQ ID NO 16
<211> LENGTH: 23
<212> TYPE: DNA
<213> ORGANISM: Artificial Sequence
<220> FEATURE:
```

-continued

```
<223> OTHER INFORMATION: Description of Artificial Sequence:  Synthetic
      Primer

<400> SEQUENCE: 16
tcaatggctt ctgtcctcct gtg                                              23
```